United States Patent
Butts et al.

(10) Patent No.: US 11,702,630 B2
(45) Date of Patent: Jul. 18, 2023

(54) IN VITRO METHODS OF DIFFERENTIATING STEM CELLS INTO NEURONS AND NEURONS GENERATED USING THE SAME

(71) Applicants: The J. David Gladstone Institutes, a testamentary trust established under the Will of J. David Gladstone, San Francisco, CA (US); Georgia Tech Research Corporation, Atlanta, GA (US); The Regents of the University of California, Oakland, CA (US)

(72) Inventors: Jessica Butts, San Francisco, CA (US); Todd C. McDevitt, San Francisco, CA (US)

(73) Assignees: The J. David Gladstone Institutes, a testamentary trust established under the Will of J. David Gladstone, San Francisco, CA (US); The Regents of the University of California, Oakland, CA (US); Georgia Tech Research Corporation, Atlanta, GA (US)

( * ) Notice: Subject to any disclaimer, the term of this patent is extended or adjusted under 35 U.S.C. 154(b) by 583 days.

(21) Appl. No.: 16/303,580

(22) PCT Filed: May 26, 2017

(86) PCT No.: PCT/US2017/034849
§ 371 (c)(1),
(2) Date: Nov. 20, 2018

(87) PCT Pub. No.: WO2017/210138
PCT Pub. Date: Dec. 7, 2017

(65) Prior Publication Data
US 2020/0318065 A1    Oct. 8, 2020

Related U.S. Application Data

(60) Provisional application No. 62/343,747, filed on May 31, 2016.

(51) Int. Cl.
*C12N 5/0793* (2010.01)
*A01K 67/027* (2006.01)

(52) U.S. Cl.
CPC .......... *C12N 5/0619* (2013.01); *A01K 67/027* (2013.01); *A01K 2207/12* (2013.01); *A01K 2227/105* (2013.01); *A01K 2267/03* (2013.01); *C12N 2501/105* (2013.01); *C12N 2501/13* (2013.01); *C12N 2501/15* (2013.01); *C12N 2501/385* (2013.01); *C12N 2501/41* (2013.01); *C12N 2501/415* (2013.01); *C12N 2501/42* (2013.01); *C12N 2501/734* (2013.01); *C12N 2506/02* (2013.01); *C12N 2506/45* (2013.01); *C12N 2533/90* (2013.01)

(58) Field of Classification Search
CPC .................................................. C12N 5/0619
See application file for complete search history.

(56) References Cited

U.S. PATENT DOCUMENTS

| | | |
|---|---|---|
| 2015/0087541 A1 | 3/2015 | Gonzalez et al. |
| 2015/0361393 A1 | 12/2015 | Nicholas et al. |
| 2016/0068806 A1 | 3/2016 | Ashton et al. |

FOREIGN PATENT DOCUMENTS

| | | |
|---|---|---|
| EP | 2334804 | 12/2013 |
| EP | 3464569 | 4/2019 |
| WO | WO 2015124725 | 8/2015 |
| WO | 2016012570 | 1/2016 |
| WO | 2017210138 | 12/2017 |

OTHER PUBLICATIONS

Brown et al. (2014, Stem Cells Dev., vol. 23(15), pp. 1765-1776) (Year: 2014).*
Brown et al. (2014, Stem Cells and Development, vol. 23(15), pp. 1765-1776) (Year: 2014).*
Iyer et al. (ePub Jan. 16, 2016, Experimental Neurology, vol. 277, pp. 305-316). (Year: 2016).*
Wilson et al. (2015, Fluids Barriers CNS, vol. 12(13), pp. 1-12). (Year: 2015).*
Van der Sanden et al. (2010, J. Cellular Biochem., vol. 111, pp. 801-807) (Year: 2010).*
Ashburner M, et al. (2000) "Gene ontology: tool for the unification of biology"; *The Gene Ontology Consortium. Nat Genet* 25(1):25-29.
Al-Mosawie, A., et al. (2007) "Heterogeneity of V2-derived interneurons in the adult mouse spinal cord"; *Eur J Neurosci*, 26(11): p. 3003-15.
Amoroso, M.W., et al. (2013) "Accelerated high-yield generation of limb-innervating motor neurons from human stem cells"; *J Neurosci*, 33(2): p. 574-86.

(Continued)

*Primary Examiner* — Anoop K Singh
*Assistant Examiner* — David A Montanari
(74) *Attorney, Agent, or Firm* — Schwegman Lundberg & Woessner, P.A.

(57) ABSTRACT

Methods of generating spinal cord glutamatergic interneurons (V2a interneurons) from human pluripotent stem cells (hPSCs) are provided. A method of the present disclosure may include culturing a first population of hPSCs in vitro in a neural induction medium that includes: a retinoic acid signaling pathway activator; a sonic hedgehog (Shh) signaling pathway activator; and a Notch signaling pathway inhibitor, wherein the culturing results in generation of a second population of cultured cells containing CHX10+ V2a interneurons. Also provided are non-human animal models that include the hPSC-derived spinal cord glutamatergic interneurons, and methods of producing the non-human animal models.

22 Claims, 24 Drawing Sheets

Specification includes a Sequence Listing.

(56) References Cited

OTHER PUBLICATIONS

Azim, E., et al. (2014) "Skilled reaching relies on a V2a propriospinal internal copy circuit"; *Nature* 508(7496); p. 357-63.
Bardy C, et al. (2016) "Predicting the functional states of human iPSC-derived neurons with singlecell RNA-seq and electrophysiology"; *Mol Psychiatry* 21(11):1573-1588.
Batista, M.F., et al. (2008) "Zebrafish V2 cells develop into excitatory CiD and Notch signalling dependent inhibitory VeLD interneurons"; *Dev Biol*,. 322(2): p. 263-75.
Ben-Shushan E, et al (2015) "Notch signaling regulates motor neuron differentiation of human embryonic stem cells"; *Stem Cells.* 33(2):403-15.
Borghese, L., et al. (2010) "Inhibition of notch signaling in human embryonic stem cell-derived neural stem cells delays G1/S phase transition and accelerates neuronal differentiation in vitro and in vivo"; *Stem Cells.* 28(5): p. 955-64.
Bretzner and. Brownstone (2013) "Lhx3-Chx10 reticulospinal neurons in locomotor circuits"; *J Neurosci*, 33(37): p. 14681-92.
Brown, C.R., et al. (2014) "Generation of v2a interneurons from mouse embryonic stem cells"; *Stem Cells Dev.* 23(15): p. 1765-76.
Butt, S.J., et al. (2002) "Firing properties of identified interneuron populations in the mammalian hindlimb central pattern generator"; *J Neurosci*,. 22(22): p. 9961-71.
Butt, S. J. and. Kiehn, O. (2003) "Functional identification of interneurons responsible for left-right coordination of hindlimbs in mammals"; *Neuron.* 38(6): p. 953-63.
Butts, et al. (2017) "Differentiation of V2a interneurons from human pluripotent stem cells"; *Proc Natl Acad Sci U S A.* 114(19):4969-4974.
Cizkova D, et al. (2007) "Functional recovery in rats with ischemic paraplegia after spinal grafting of human spinal stem cells"; *Neuroscience* 147:546-560.
Cornacchia, D. and. Studer, L (2015) "Back and forth in time: Directing age in iPSC-derived lineages"; *Brain Res.* 1656:14-26.
Crawford TQ, Roelink H (2007) "The notch response inhibitor DAPT enhances neuronal differentiation in embryonic stem cell-derived embryoid bodies independently of sonic hedgehog signaling"; *Dev Dyn* 236:886-892.
Crone, S.A., et al., (2008) "Genetic ablation of V2a ipsilateral interneurons disrupts left-right locomotor coordination in mammalian spinal cord"; *Neuron* 60(1): p. 70-83.
Crone, S.A., et al., (2012) "Irregular Breathing in Mice following Genetic Ablation of V2a Neurons"; *J Neurosci.* 32(23): p. 7895-906.
Cummings BJ, et al. (2005) "Human neural stem cells differentiate and promote locomotor recovery in spinal cord-injured mice"; *Proc Natl Acad Sci USA* 102:14069-14074.
Del Barrio, M.G., et al. (2007) "A regulatory network involving Foxn4, Mash1 and delta-like 4/Notch1 generates V2a and V2b spinal interneurons from a common progenitor pool"; *Development*, 134(19): p. 3427-36.
Dobin A, et al. (2013) "STAR: ultrafast universal RNA-seq aligner"; *Bioinformatics* 29(1):15-21.
Dougherty, K.J. and Kiehn, O. (2010) "Firing and cellular properties of V2a interneurons in the rodent spinal cord"; *J Neurosci.* 30(1): p. 24-37.
Eden E, et al. (2007) Discovering motifs in ranked lists of DNA sequences. *PLoS Comput Biol* 3(3):e39.
Eden E, et al. (2009) "GOrilla: a tool for discovery and visualization of enriched GO terms in ranked gene lists"; *BMC Bioinformatics* 10:1-7.
Ericson, J., et al. (1997) "Pax6 controls progenitor cell identity and neuronal fate in response to graded Shh signaling"; *Cell* 90(1): p. 169-80.
Guest J, et al. 2013) "Clinical translation of autologous Schwann cell transplantation for the treatment of spinal cord injury"; *Curr Opin Organ Transplant* 78:682-689.
Iyer, N.R., et al. (2016) "Generation of highly enriched V2a interneurons from mouse embryonic stem cells"; *Exp Neurol.* 277: p. 305-16.
Karunaratne A, et al. (2002) "GATA proteins identify a novel ventral interneuron subclass in the developing chick spinal cord"; *Dev Biol* 249:30-43.
Keirstead HS, et al. (2005) "Human embryonic stem cell-derived oligodendrocyte progenitor cell transplants remyelinate and restore locomotion after spinal cord injury"; *J Neurosci* 25:4694-4705.
Kessel M (1992) "Respecification of vertebral identities by retinoic acid"; *Development* 115:487-501.
Li, X.J., et al. (2005) "Specification of motoneurons from human embryonic stem cells"; *Nat Biotechnol*, 23(2): p. 215-21.
Li S, et al. (2005) "Foxn4 acts synergistically with Mash1 to specify subtype identity of V2 interneurons in the spinal cord"; *Proc Natl Acad Sci USA* 102:10688-10693.
Lian, X., et al. (2013) "Directed cardiomyocyte differentiation from human pluripotent stem cells by modulating Wnt/β-catenin signaling under fully defined conditions"; *Nat Protoc*,. 8(1): p. 162-75.
Livak, K.J. and Schmittgen T.D. (2001) "Analysis of relative gene expression data using real-time quantitative PCR and the 2(-Delta Delta C(T)) Method"; *Methods.* 25(4): p. 402-8.
Louvi, A. and S. Artavanis-Tsakonas (2006) "Notch signalling invertebrate neural development"; *Nat Rev Neurosci*,. 7(2): p. 93-102.
Lu P, et al. (2012) "Long-distance growth and connectivity of neural stem cells after severe spinal cord injury"; *Cell* 150:1264-1273.
Lundfald, L. et al. (2007) "Phenotype of V2-derived interneurons and their relationship to the axon guidance molecule EphA4 in the developing mouse spinal cord"; *Eur J Neurosci*,. 26(11): p. 2989-3002.
Macosko EZ, et al. (2015) "Highly Parallel Genome-wide Expression Profiling of Individual Cells Using Nanoliter Droplets"; *Cell* 161(5):1202-1214.
Marklund, U., et al. (2014) "Detailed expression analysis of regulatory genes in the early developing human neural tube"; *Stem Cells Dev.* 23(1): p. 5-15.
Maroof, A.M., et al. (2013) "Directed differentiation and functional maturation of cortical interneurons from human embryonic stem cells"; *Cell Stem Cell.* 12(5): p. 559-72.
Müller HW, Seifert W (1982) "A neurotrophic factor (NTF) released from primary glial cultures supports survival and fiber outgrowth of cultured hippocampal neurons"; *J Neurosci Res* 8:195-204.
Ni, Y., et al. (2014) "Characterization of long descending premotor propriospinal neurons in the spinal cord"; *J Neurosci*, 34(28): p. 9404-17.
Nicholas, C.R., et al. (2013) "Functional maturation of hPSC-derived forebrain interneurons requires an extended timeline and mimics human neural development"; *Cell Stem Cell*, 12(5): p. 573-86.
Okada, Y., et al. (2004) "Retinoic-acid-concentration-dependent acquisition of neural cell identity during in vitro differentiation of mouse embryonic stem cells"; *Dev Biol*,. 275(1): p. 124-42.
Perrier, A.L., et al. (2004) "Derivation of midbrain dopamine neurons from human embryonic stem cells"; *Proc Natl Acad Sci U S A* 101(34): p. 12543-8.
Pierani A, et al. (1999) "A sonic hedgehog-independent, retinoid-activated pathway of neurogenesis in the ventral spinal cord"; *Cell* 97:903-915.
Roskams, A.J., et al. (1998) "Expression of neuron-specific beta-III tubulin during olfactory neurogenesis in the embryonic and adult rat"; *Neuroscience*,. 83(1): p. 191-200.
Satija R, et al. (2015) "Spatial reconstruction of single-cell gene expression data"; *Nat Biotechnol* 33(5):495-502.
Shi, Y. et al. (2012) "Directed differentiation of human pluripotent stem cells to cerebral cortex neurons and neural networks"; *Nat Protoc.* 7(10): p. 1836-46.
Skaggs, K., et al. (2011) "Regulation of spinal interneuron development by the Olig-related protein Bhlhb5 and Notch signaling"; *Development.* 138(15): p. 3199-211.
Van Der Maaten and Hinton (2008) "Visualizing Data Using t-SNE"; *Journal of Machine Learning Research* 9:2579-2605.
Wichterle H, et al. (2002) "Directed differentiation of embryonic stem cells into motor neurons"; *Cell* 110:385-397.
Wilson L, et al. (2004) "Retinoic acid and the control of dorsoventral patterning in the avian spinal cord"; *Dev Biol* 269:433-446.

(56) References Cited

OTHER PUBLICATIONS

Zhong, G., et al. (2010) "Electrophysiological characterization of V2a interneurons and their locomotor-related activity in the neonatal mouse spinal cord"; *J Neurosci.* 30(1): p. 170-82.
"European Application Serial No. 17807300.3, Extended European Search Report dated Feb. 11, 2020", 7 pgs.
"International Application Serial No. PCT US2017 034849, International Search Report dated Aug. 23, 2017", 4 pgs.
"International Application Serial No. PCT US2017 034849, Written Opinion dated Aug. 23, 2017", 5 pgs.
"International Application Serial No. PCT US2017 034849, International Preliminary Report on Patentability dated Dec. 13, 2018", 7 pgs.
"European Application Serial No. 17807300.3, Response to Communication pursuant to Rules 161(1) and 162 EPC filed Jul. 18, 2019", 15 pgs.
Brown, "Generation of v2a interneurons from mouse embryonic stem cells", Stem Cells Dev, vol. 23, No. 15, (Jan. 8, 2014), 1765-1776.
Butts, "Differentiation of V2a Interneurons from Human Pluripotent Stem Cells", Proc. Natl. Acad. Sci. USA, vol. 114, No. 19, (May 9, 2017), 4969-4974.
Butts, Jessica C, "V2a interneuron differentiation from mouse and human pluripotent stem cells", Nature Protocols, Nature Publishing Group, GB, vol. 14, No. 11, (Oct. 18, 2019), 3033-3058.
Hevner, R F, "Transcription factors in glutamatergic neurogenesis: Conserved programs in neocortex, cerebellum, and adult hippocampus", Neuroscience Research, Elsevier, Shannon, IR, vol. 55, No. 3, (Jul. 1, 2006), 223-233.
Hynek, Wichterle, "Differentiation of Mouse Embryonic Stem Cells to Spinal Motor Neurons", Current Protocols in Stem Cell Biology, vol. 5, No. 1, (May 1, 2008), 9 pgs.
Iyer, "Generation of highly enriched V2a interneurons from mouse embryonic stem cells", Exp Neurol. March, vol. 277, (2016), 305-316.
Iyer, Nisha, "Developing High Purity Embryonic Stem Cell Derived V2a Interneurons for In Vitro Investigation and Transplantation Following Spinal Cord Injury", Thesis, Washington University Open Scholarship, [Online] Retrieved from the Internet : https: openscholarship.wustl.edu cgi viewcontent.cgi ?article=1205andcontext=eng_etds, (Dec. 15, 2016), 1-197.
Mccreedy, Dylan A, "A New Method for Generating High Purity Motoneurons From Mouse Embryonic Stem Cells", Biotechnology and Bioengineering, vol. 111, No. 10, (Oct. 2014), 2041-2055.
Tandis, Vazin, "Efficient derivation of cortical glutamatergic neurons from human pluripotent stem cells: A model system to study neurotoxicity in Alzheimer's disease", Neurobiology of Disease, vol. 62, (Sep. 18, 2013), 62-72.
"European Application Serial No. 17807300.3, Response filed Dec. 22, 2020 to Extended European Search Report dated Feb. 11, 2020", 13 pgs.
"European Application Serial No. 17807300.3, Communication Pursuant to Article 94(3) EPC dated Aug. 10, 2022", 4 pgs.
"European Application Serial No. 17807300.3, Response filed Dec. 9, 2022 to Communication Pursuant to Article 94(3) EPC dated Aug. 10, 2022", 22 pgs.

\* cited by examiner

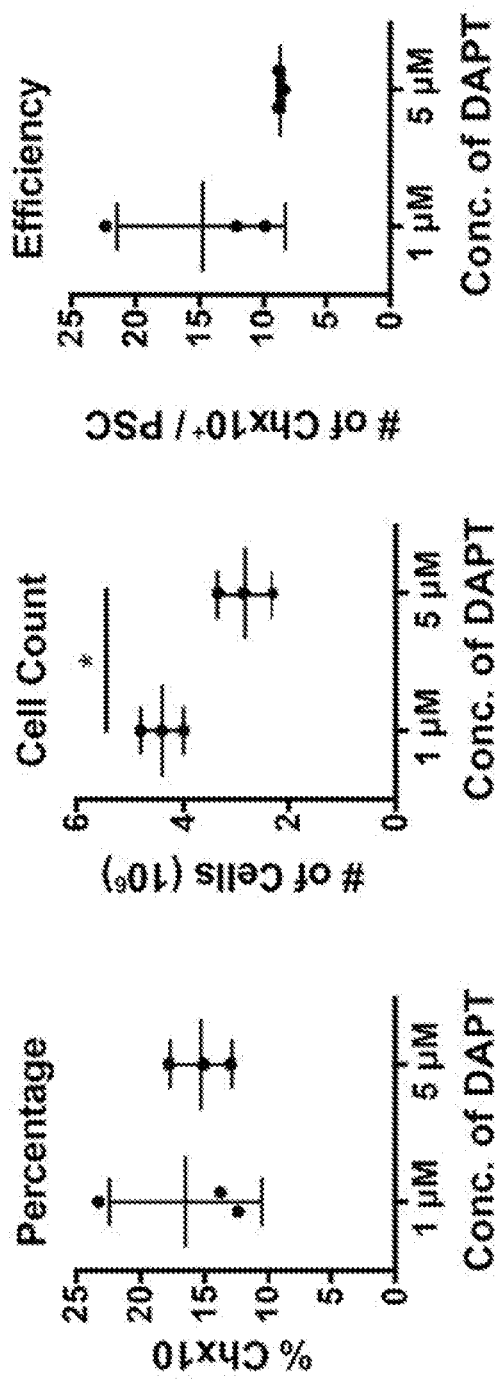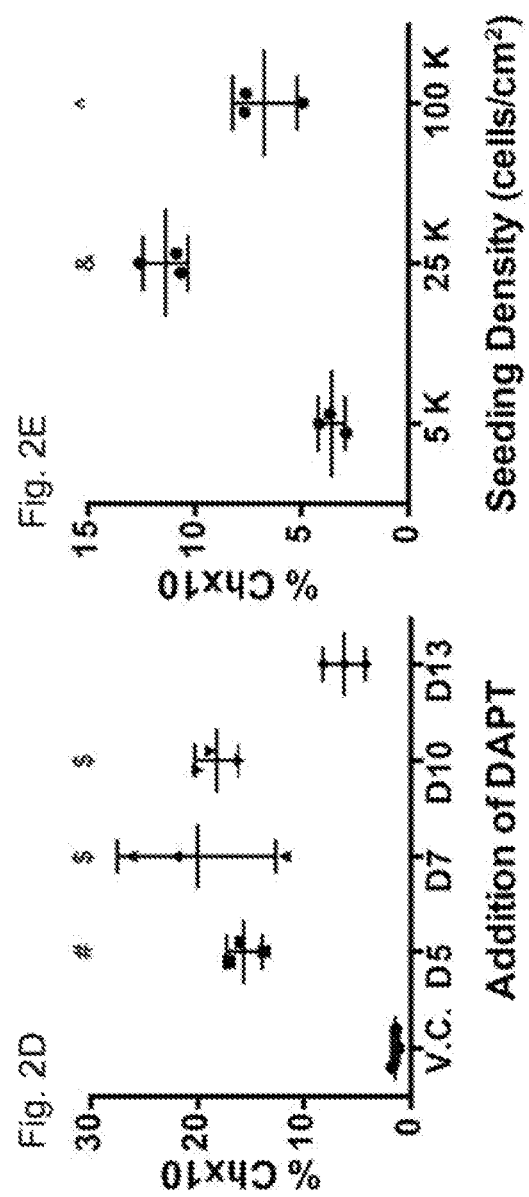

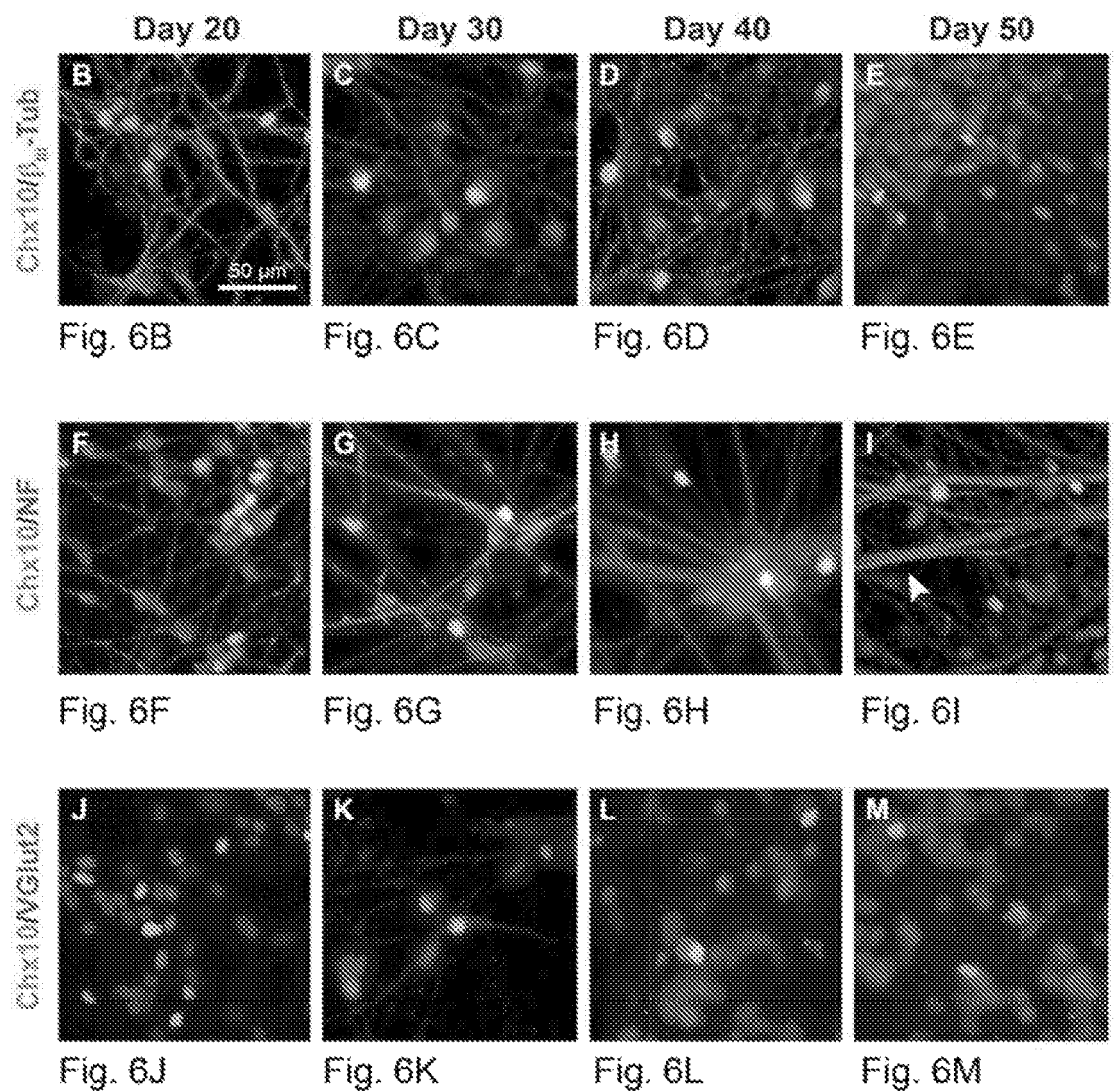

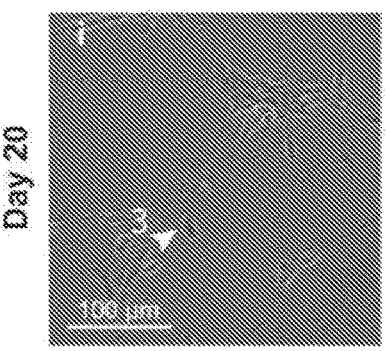 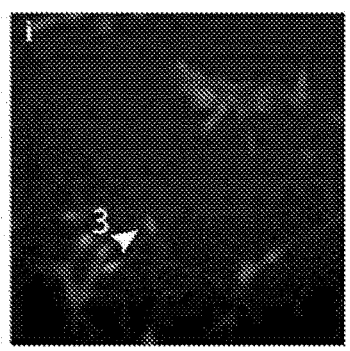 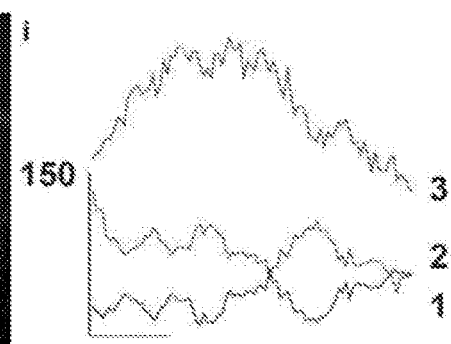
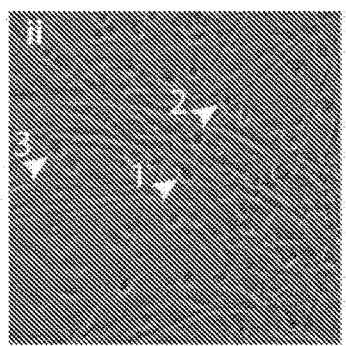 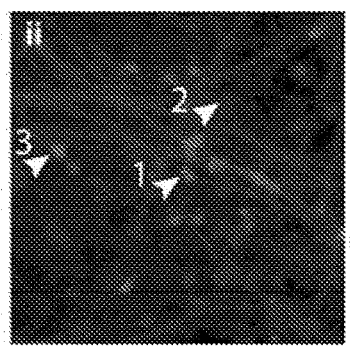 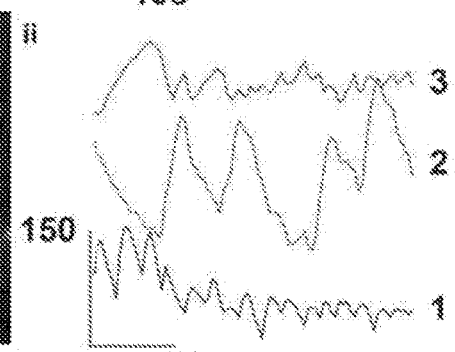

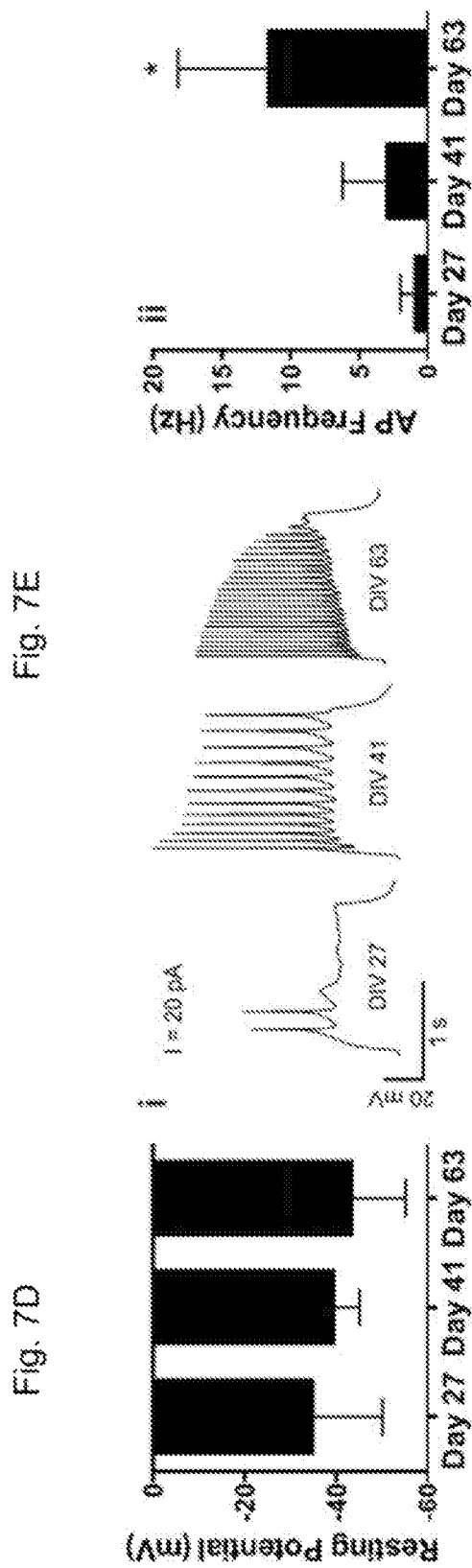

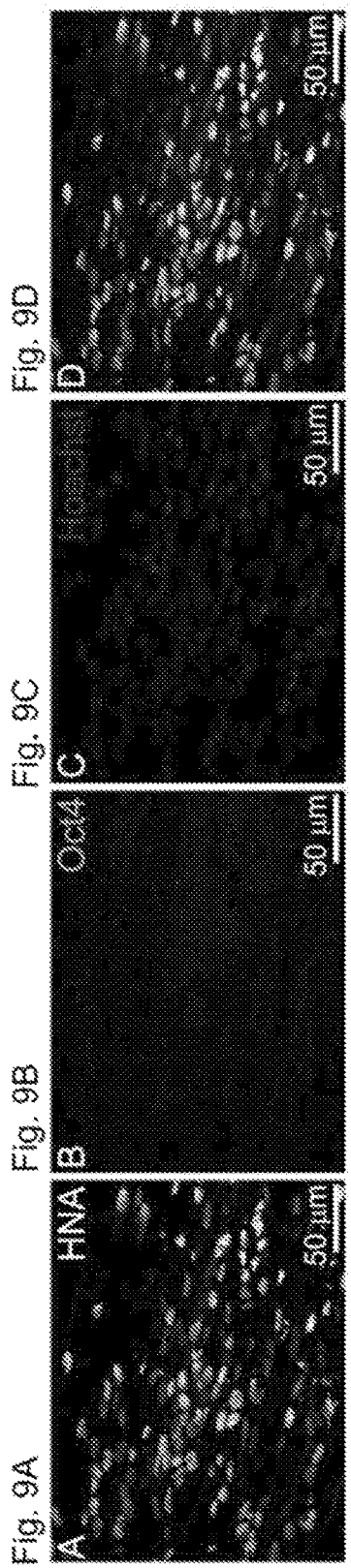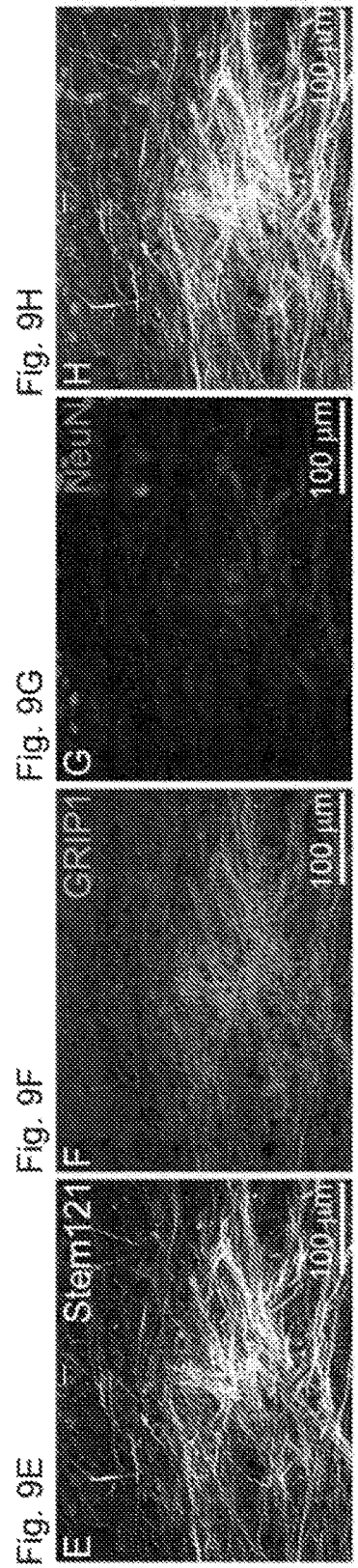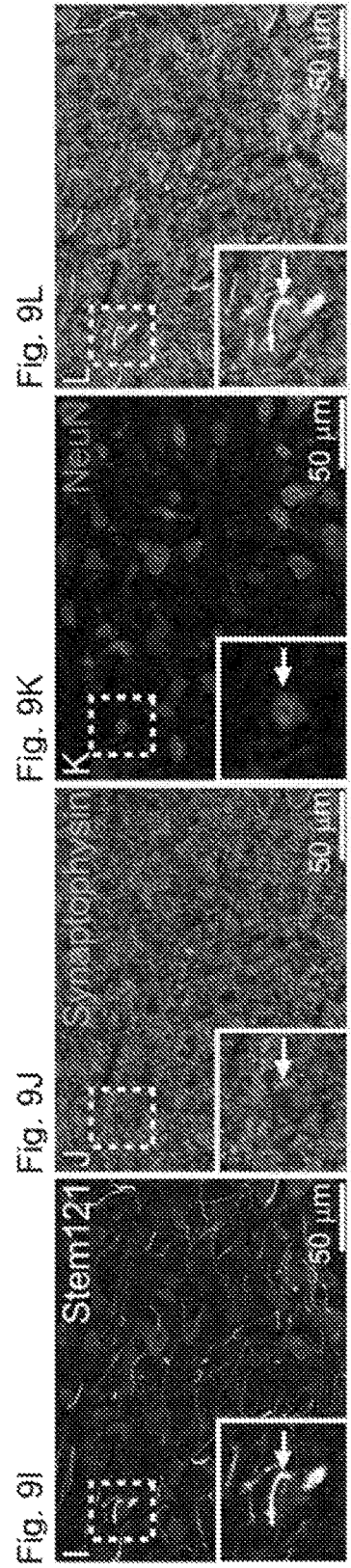

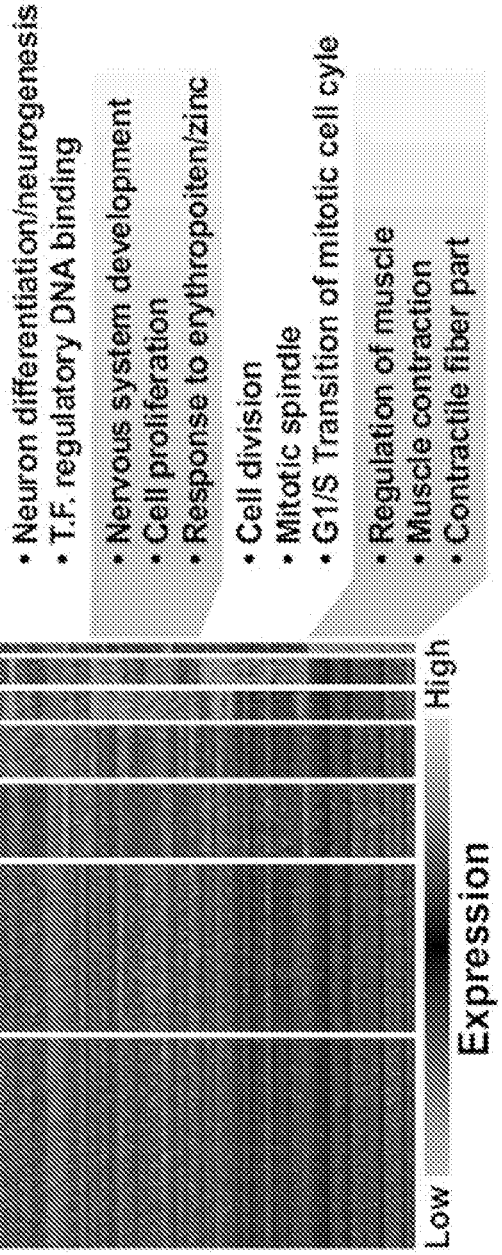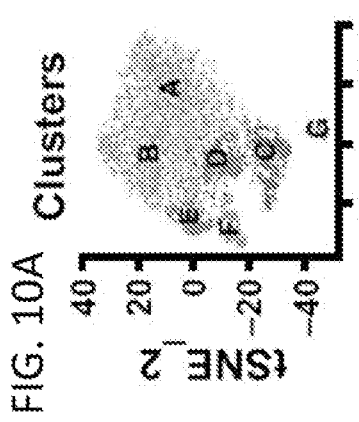
FIG. 10A, FIG. 10B, FIG. 10C

Cluster Interpretation

SEQUENCE LISTING

<160> NUMBER OF SEQ ID NOS: 42

<210> SEQ ID NO 1
<211> LENGTH: 20
<212> TYPE: DNA
<213> ORGANISM: Artificial Sequence
<220> FEATURE:
<223> OTHER INFORMATION: Synthetic sequence

<400> SEQUENCE: 1
cttccacagg aggcctacac                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic sequence

<400> SEQUENCE: 2
cggcgacaca ggacaatctt                                            20

<210> SEQ ID NO 3
<211> LENGTH: 20
<212> TYPE: DNA
<213> ORGANISM: Artificial Sequence
<220> FEATURE:
<223> OTHER INFORMATION: Synthetic sequence

<400> SEQUENCE: 3
cgtacagctg tctgatcgcc                                            20

<210> SEQ ID NO 4
<211> LENGTH: 20
<212> TYPE: DNA
<213> ORGANISM: Artificial Sequence
<220> FEATURE:
<223> OTHER INFORMATION: Synthetic sequence

<400> SEQUENCE: 4
ttgtgctcgg agggtttctt                                            20

<210> SEQ ID NO 5
<211> LENGTH: 20
<212> TYPE: DNA
<213> ORGANISM: Artificial Sequence
<220> FEATURE:
<223> OTHER INFORMATION: Synthetic sequence

<400> SEQUENCE: 5
cgcatccaga ttttcgggtc                                            20

<210> SEQ ID NO 6
<211> LENGTH: 20
<212> TYPE: DNA
<213> ORGANISM: Artificial Sequence
<220> FEATURE:
<223> OTHER INFORMATION: Synthetic sequence

<400> SEQUENCE: 6
tctcttaacg ggaaggggca                                            20

<210> SEQ ID NO 7
<211> LENGTH: 18
<212> TYPE: DNA
<213> ORGANISM: Artificial Sequence
<220> FEATURE:
<223> OTHER INFORMATION: Synthetic sequence

<400> SEQUENCE: 7
gagcgagcgg tgcatttg                                              18

<210> SEQ ID NO 8
<211> LENGTH: 19
<212> TYPE: DNA
<213> ORGANISM: Artificial Sequence
<220> FEATURE:

<223> OTHER INFORMATION: Synthetic sequence

<400> SEQUENCE: 8
gaaccccagg cagctagac                                             19

<210> SEQ ID NO 9
<211> LENGTH: 22
<212> TYPE: DNA
<213> ORGANISM: Artificial Sequence
<220> FEATURE:
<223> OTHER INFORMATION: Synthetic sequence

<400> SEQUENCE: 9
atgcattcaa actgaggtgc ct                                         22

<210> SEQ ID NO 10
<211> LENGTH: 20
<212> TYPE: DNA
<213> ORGANISM: Artificial Sequence
<220> FEATURE:
<223> OTHER INFORMATION: Synthetic sequence

<400> SEQUENCE: 10
ccaccctgca aagggaatct                                            20

<210> SEQ ID NO 11
<211> LENGTH: 20
<212> TYPE: DNA
<213> ORGANISM: Artificial Sequence
<220> FEATURE:
<223> OTHER INFORMATION: Synthetic sequence

<400> SEQUENCE: 11
gaacccttgc actccctacc                                            20

<210> SEQ ID NO 12
<211> LENGTH: 20
<212> TYPE: DNA
<213> ORGANISM: Artificial Sequence
<220> FEATURE:
<223> OTHER INFORMATION: Synthetic sequence

<400> SEQUENCE: 12
ggctctcacc ggcagtattt                                            20

<210> SEQ ID NO 13
<211> LENGTH: 20
<212> TYPE: DNA
<213> ORGANISM: Artificial Sequence
<220> FEATURE:
<223> OTHER INFORMATION: Synthetic sequence

<400> SEQUENCE: 13
acgatcgtag agggacggaa                                            20

<210> SEQ ID NO 14
<211> LENGTH: 20
<212> TYPE: DNA
<213> ORGANISM: Artificial Sequence
<220> FEATURE:
<223> OTHER INFORMATION: Synthetic sequence

<400> SEQUENCE: 14
catcagcgct atgcaggaca                                            20

```
<210> SEQ ID NO 15
<211> LENGTH: 20
<212> TYPE: DNA
<213> ORGANISM: Artificial Sequence
<220> FEATURE:
<223> OTHER INFORMATION: Synthetic sequence

<400> SEQUENCE: 15
ctggacactg ggagattcgg                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic sequence

<400> SEQUENCE: 16
cactcaggac gaaggaaccc                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic sequence

<400> SEQUENCE: 17
cacaagaaag accacccgga                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic sequence

<400> SEQUENCE: 18
cagttatcag gaggcgctgg                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic sequence

<400> SEQUENCE: 19
tggattaagg atgaggcccg                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic sequence

<400> SEQUENCE: 20
tatctacaac cgcccctcca                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic sequence
```

<400> SEQUENCE: 21
ccttctgaca gctcggtgtt                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic sequence

<400> SEQUENCE: 22
cttcggccca caccct taat                                                   20

<210> SEQ ID NO 23
<211> LENGTH: 20
<212> TYPE: DNA
<213> ORGANISM: Artificial Sequence
<220> FEATURE:
<223> OTHER INFORMATION: Synthetic sequence

<400> SEQUENCE: 23
cctgtatcct gtcttccggc                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic sequence

<400> SEQUENCE: 24
ggagccgctc atcttgttct                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic sequence

<400> SEQUENCE: 25
cagcacaggc tgcaggaata                                                    20

<210> SEQ ID NO 26
<211> LENGTH: 20
<212> TYPE: DNA
<213> ORGANISM: Artificial Sequence
<220> FEATURE:
<223> OTHER INFORMATION: Synthetic sequence

<400> SEQUENCE: 26
aaaaggtcat cgggctctgg                                                    20

<210> SEQ ID NO 27
<211> LENGTH: 20
<212> TYPE: DNA
<213> ORGANISM: Artificial Sequence
<220> FEATURE:
<223> OTHER INFORMATION: Synthetic sequence

<400> SEQUENCE: 27
ctaattcagg gcgctctcgg                                                    20

<210> SEQ ID NO 28
<211> LENGTH: 25

```
<212> TYPE: DNA
<213> ORGANISM: Artificial Sequence
<220> FEATURE:
<223> OTHER INFORMATION: Synthetic sequence

<400> SEQUENCE: 28
tcagattcct atgctgattg gtgat                                           25

<210> SEQ ID NO 29
<211> LENGTH: 22
<212> TYPE: DNA
<213> ORGANISM: Artificial Sequence
<220> FEATURE:
<223> OTHER INFORMATION: Synthetic sequence

<400> SEQUENCE: 29
actgatgact tcccagaact gt                                              22

<210> SEQ ID NO 30
<211> LENGTH: 22
<212> TYPE: DNA
<213> ORGANISM: Artificial Sequence
<220> FEATURE:
<223> OTHER INFORMATION: Synthetic sequence

<400> SEQUENCE: 30
aacttcacct tccctccaac ca                                              22

<210> SEQ ID NO 31
<211> LENGTH: 20
<212> TYPE: DNA
<213> ORGANISM: Artificial Sequence
<220> FEATURE:
<223> OTHER INFORMATION: Synthetic sequence

<400> SEQUENCE: 31
ggtgagcttg ggcacaaaag                                                 20

<210> SEQ ID NO 32
<211> LENGTH: 20
<212> TYPE: DNA
<213> ORGANISM: Artificial Sequence
<220> FEATURE:
<223> OTHER INFORMATION: Synthetic sequence

<400> SEQUENCE: 32
tcgatgtatg gccgcttctc                                                 20

<210> SEQ ID NO 33
<211> LENGTH: 20
<212> TYPE: DNA
<213> ORGANISM: Artificial Sequence
<220> FEATURE:
<223> OTHER INFORMATION: Synthetic sequence

<400> SEQUENCE: 33
tgagccatta cagcccaagg                                                 20

<210> SEQ ID NO 34
<211> LENGTH: 20
<212> TYPE: DNA
<213> ORGANISM: Artificial Sequence
<220> FEATURE:
<223> OTHER INFORMATION: Synthetic sequence

<400> SEQUENCE: 34
```

```
aattcaggcc cgtagactgc                                                    20

<210> SEQ ID NO 35
<211> LENGTH: 20
<212> TYPE: DNA
<213> ORGANISM: Artificial Sequence
<220> FEATURE:
<223> OTHER INFORMATION: Synthetic sequence

<400> SEQUENCE: 35
gtctcctcgc cttccaagag                                                    20

<210> SEQ ID NO 36
<211> LENGTH: 20
<212> TYPE: DNA
<213> ORGANISM: Artificial Sequence
<220> FEATURE:
<223> OTHER INFORMATION: Synthetic sequence

<400> SEQUENCE: 36
cacggcctcc aatgatctct                                                    20

<210> SEQ ID NO 37
<211> LENGTH: 20
<212> TYPE: DNA
<213> ORGANISM: Artificial Sequence
<220> FEATURE:
<223> OTHER INFORMATION: Synthetic sequence

<400> SEQUENCE: 37
ggagcaatac ggtaccctgg                                                    20

<210> SEQ ID NO 38
<211> LENGTH: 20
<212> TYPE: DNA
<213> ORGANISM: Artificial Sequence
<220> FEATURE:
<223> OTHER INFORMATION: Synthetic sequence

<400> SEQUENCE: 38
aagtgggcgc tcttgtagtg                                                    20

<210> SEQ ID NO 39
<211> LENGTH: 19
<212> TYPE: DNA
<213> ORGANISM: Artificial Sequence
<220> FEATURE:
<223> OTHER INFORMATION: Synthetic sequence

<400> SEQUENCE: 39
tttgccccct cgaatctgc                                                     19

<210> SEQ ID NO 40
<211> LENGTH: 20
<212> TYPE: DNA
<213> ORGANISM: Artificial Sequence
<220> FEATURE:
<223> OTHER INFORMATION: Synthetic sequence

<400> SEQUENCE: 40
tggggaggtg cagtctgtat                                                    20

<210> SEQ ID NO 41
<211> LENGTH: 20
<212> TYPE: DNA
<213> ORGANISM: Artificial Sequence
```

```
<220> FEATURE:
<223> OTHER INFORMATION: Synthetic sequence

<400> SEQUENCE: 41
ctggtgagga ccaccacatc                                                    20

<210> SEQ ID NO 42
<211> LENGTH: 20
<212> TYPE: DNA
<213> ORGANISM: Artificial Sequence
<220> FEATURE:
<223> OTHER INFORMATION: Synthetic sequence

<400> SEQUENCE: 42
tggtgtactt cagcggtcac                                                    20
```

IN VITRO METHODS OF DIFFERENTIATING STEM CELLS INTO NEURONS AND NEURONS GENERATED USING THE SAME

CROSS-REFERENCE

This application claims the benefit of U.S. Provisional Patent Application No. 62/343,747, filed May 31, 2016, which application is incorporated herein by reference in its entirety.

INTRODUCTION

The spinal cord includes multiple neuronal species that are important in the context of motor control and arise from distinct progenitor domains in the neural tube during development. Excitatory V2a interneurons, in particular, are an important component of central pattern generators because of their contribution to locomotion and respiratory activity. However, the lack of a robust source of human V2a interneurons limits molecular profiling and the ability to examine the therapeutic potential of V2a interneurons following injury to the central nervous system.

SUMMARY

Methods of generating spinal cord glutamatergic interneurons (V2a interneurons) from human pluripotent stem cells (hPSCs) are provided. A method of the present disclosure may include culturing a first population of hPSCs in vitro in a neural induction medium that includes: a retinoic acid signaling pathway activator; a sonic hedgehog (Shh) signaling pathway activator; and a Notch signaling pathway inhibitor, wherein the culturing results in generation of a second population of cultured cells containing CHX10+ V2a interneurons.

BRIEF DESCRIPTION OF THE DRAWINGS

FIGS. 2A-2E are a collection of graphs showing that DAPT concentration affects V2a interneuron yield, according to embodiments of the present disclosure.

FIGS. 6A-6M are a collection of schematic diagrams and images showing in vitro maturation of in vitro hPSC-derived V2a interneurons, according to embodiments of the present disclosure.

FIGS. 7A-7E are a collection of graphs and images showing electrophysiological properties of maturing in vitro hPSC-derived V2a interneurons, according to embodiments of the present disclosure.

FIGS. 9A-9L are a collection of images showing maturation of in vitro hPSC-derived V2a interneurons that are transplanted into the ventral horns of mice spinal cords, according to embodiments of the present disclosure.

FIGS. 10A-10F provide results for single-cell RNAseq analysis of V2a interneuron cultures. (FIG. 10A) tSNE plot of V2a interneuron cultures indicating seven clusters. (FIG. 10B) CHX10 expression (black dots) overlaid on cluster B (gold dots). Open circles represent the rest of the population. (FIG. 10C) Heatmap of the top 20 globally differentially expressed genes for each cluster. Expression values are normalized for each individual gene, with blue indicating low expression and yellow indicating high expression. GO terms for each cluster were determined through global and pairwise comparisons. (FIG. 10D) Percentage of cells found in each cluster. (FIG. 10E) Dendrogram of the relationships between clusters. (FIG. 10F) Interpretation of the different cell types comprising V2a interneuron cultures based on cluster analysis.

DEFINITIONS

Figure 1A:
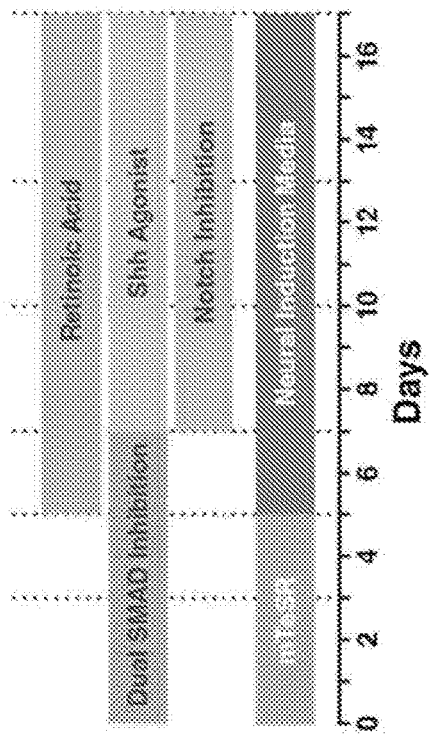
FIGS. 1A-1H are a collection of schematic diagrams, graphs and images showing in vitro differentiation of human pluripotent stem cells (hPSCs) into a V2a interneuron population by modulating morphogen signaling pathways, according to embodiments of the present disclosure.

The term "about" as used herein when referring to a measurable value such as an amount, a length, and the like, is meant to encompass variations of ±20% or ±10%, more preferably ±5%, even more preferably ±1%, and still more preferably ±0.1% from the specified value.

"in vitro" as used herein describes an environment outside of a living body. The environment may be a tissue culture medium inside a flask, dish, or any other suitable container, or may be a body part, tissue, or tissue slice that is in the tissue culture medium.

"Differentiation" refers to a physiological and/or morphological change (e.g., change in gene and/or protein expression pattern, and/or morphology) that occurs in a cell that results in the cell assuming certain specialized functions, also called a cell fate. The change may be an irreversible change, where the differentiated cell loses the ability to assume a different cell fate. The change may be partial or substantially complete with respect to mature adult (e.g., somatic) cells. A partially changed cell may exhibit some of the physiological and/or morphological characteristics of the somatic cell, but may be missing others. A cell may be "committed" to a somatic cell fate when the cell shows at least a partial, substantially irreversible change toward the cell fate, and in some cases, may further develop more of the missing physiological and/or morphological characteristics of the somatic cell without having to provide any differentiation cues. In the case of neurons, in some instances, differentiation may not include axon guidance or other asymmetric developmental changes at the cellular level due to spatial cues acting on a single neuron. Thus, a mature neuron in vitro may not necessarily have neurite branching patterns that resemble the same neuron differentiated and developed in its in vivo context.

"Marker" as used herein, refers to a gene whose expression (RNA transcript expression or protein expression) level is specific to a cell fate, or to a progenitor cell for one or more cell fates.

"Morphogen" as used herein, refers to biological signaling molecules that provide spatial and/or temporal cues within a developing organism to direct appropriate differentiation and/or movement of cells for proper development.

As used herein, the term "stem cell" refers to an undifferentiated cell that can be induced to proliferate. The stem cell is capable of self-maintenance or self-renewal, meaning that with each cell division, at least one daughter cell will also be a stem cell. Stem cells can be obtained from embryonic, post-natal, juvenile, or adult tissue. Stem cells can be pluripotent or multipotent. The term "progenitor cell," as used herein, refers to an undifferentiated cell derived from a stem cell, and is not itself a stem cell. Some progenitor cells can produce progeny that are capable of differentiating into more than one cell type.

Stem cells include pluripotent stem cells, which can form cells of any of the body's tissue lineages: mesoderm, endoderm and ectoderm. Therefore, for example, stem cells can be selected from a human embryonic stem (ES) cell; a human inner cell mass (ICM)/epiblast cell; a human primitive ectoderm cell, a human primitive endoderm cell; a human primitive mesoderm cell; and a human primordial germ (EG) cell. Stem cells also include multipotent stem cells, which can form multiple cell lineages that constitute an entire tissue or tissues, such as but not limited to hematopoietic stem cells or neural precursor cells. Stem cells also include totipotent stem cells, which can form an entire organism. In some embodiments, the stem cell is a partially differentiated or differentiating cell. In some embodiments, the stem cell is an induced pluripotent stem cell (iPSC), which has been reprogrammed or de-differentiated.

"Human pluripotent stem cell (hPSC)" refers to a pluripotent stem cell (PSC) that is derived from a human tissue or cell (e.g., a human embryo, a human somatic cell, etc.).

"Expression" refers to detectable production of a gene product by a cell. The gene product may be a transcription product (i.e., RNA), which may be referred to as "gene expression", or the gene product may be a translation product of the transcription product (i.e., a protein), depending on the context.

"V2a interneurons" refer to a subtype of glutamatergic (i.e., excitatory) interneurons that are found in the spinal cord and hindbrain. V2a interneurons may be distinguished from other interneurons and motoneurons in the spinal cord (and share the same progenitor cells) based on higher expression of V2a-specific markers, such as CHX10 or SOX14, relative to these other neurons. Thus, a V2a interneuron generated by methods of the present disclosure may be identified by an elevated protein or gene expression level of CHX10 in a cell (i.e., a CHX10+ cell) differentiated from an hPSC. V2a interneurons may also have higher expression of other markers, such as FOXN4 and LHX3, that are also highly expressed in one or more neuronal subtypes that share the same progenitors.

"Culture" as used herein, refers to growing (i.e., causing to multiply by dividing), maintaining (i.e., keeping the cells alive and/or growing without differentiating) and/or differentiating one or more cells by providing the cells with a suitable environment. The cells may be provided with an in vitro environment (e.g., a suitable cell culture medium) that is conducive for survival, growth, and/or differentiation of the cells. An in vitro environment for growing, maintaining and/or differentiating mammalian cells may include a suitable temperature (e.g., about 37° C.) and a suitable atmosphere (e.g., about 5% CO2, humidified atmosphere) provided by, e.g., an incubator.

"Seed" as used herein, refers to initiating a culture of cells by providing an initial population of cells with a suitable culturing environment (e.g., adding cells to a cell culture medium). In some cases, the cells are initially free-floating and become attached to a cell culture substrate as the cells are cultured.

A "non-human animal model" as used herein may refer to a non-human animal that can be used as a surrogate host for transplanting and developing a cell derived by differentiating a human pluripotent stem cell (hPSC) (e.g., a hPSC-derived cell committed to a V2a interneuron cell fate).

Before the present disclosure is further described, it is to be understood that the disclosed subject matter is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosed subject matter. The upper and lower limits of these smaller ranges may independently be included in the smaller ranges, and are also encompassed within the disclosed subject matter, subject to any specifically excluded limit in the stated range. Where the stated range includes one or both of the limits, ranges excluding either or both of those included limits are also included in the disclosed subject matter.

Unless defined otherwise, all technical and scientific terms used herein have the same meaning as commonly understood by one of ordinary skill in the art to which the disclosed subject matter belongs. Although any methods and materials similar or equivalent to those described herein can also be used in the practice or testing of the disclosed subject matter, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an interneuron" includes a plurality of such interneurons and reference to "the inhibitor" includes reference to one or more inhibitors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the disclosed subject matter, which are, for clarity, described in the context of separate embodiments, may also be provided in combination in a single embodiment. Conversely, various features of the disclosed subject matter, which are, for brevity, described in the context of a single embodiment, may also be provided separately or in any suitable sub-combination. All combinations of the embodiments pertaining to the disclosure are specifically embraced by the disclosed subject matter and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the disclosed subject matter is not entitled to antedate such publication. Further, the dates of publication provided may be different from the actual publication dates which may need to be independently confirmed.

DETAILED DESCRIPTION

As summarized above, methods of generating spinal cord glutamatergic interneurons (V2a interneurons) from human pluripotent stem cells (hPSCs) are provided. A method of the present disclosure includes culturing hPSCs in vitro in a medium, e.g., a neural induction medium, that includes a combination of modulators of developmental signaling pathways in the hPSCs, in a manner sufficient to induce differentiation of the hPSCs into a population of cells that are at least committed to a V2a interneuron cell fate. The V2a interneurons may be matured, in vitro or in vivo, to acquire one or more characteristics of a mature V2a interneuron.

hPSC-Derived V2a Interneurons

The population of cells generated by the present methods includes cells that express at least one marker specific for V2a interneurons, and may be distinguished from other spinal cord interneurons or undifferentiated hPSCs based on the expression levels of one or more genes (i.e., based on one or more markers). The "V2a interneuron" as used in the context of hPSC-derived cells in vitro, is meant to include substantially mature V2a interneurons as well as partially differentiated cells committed to the V2a interneuron cell fate. The expression level of a gene on average across a population of cells may be measured by, e.g., measuring RNA transcript level in a sample containing nucleic acid isolated from the population of cells using, e.g., real time quantitative polymerase chain reaction (RT-qPCR). The expression level of a gene at single cell resolution may be measured by, e.g., measuring the level of the protein encoded by the gene in individual cells, such as by contacting a detectable antibody specific to the protein encoded by the gene (e.g., a primary antibody that is specific to the protein encoded by the gene and that is detectable when bound by a detectably labeled secondary antibody specific to the primary antibody) with permeabilized cells from a population of cells, followed by flow cytometry. Alternatively, the expression level of a gene at single cell resolution in cells of a tissue slice or on a slide may be measured by immunohistochemistry.

CHX10 (also known as VSX2; Gene ID: 338917) may be a marker for cells committed to the V2a interneuron cell fate. Thus in some embodiments, V2a interneurons generated from hPSCs according to methods of the present disclosure express CHX10 at a level higher than the level of expression of CHX10 in undifferentiated hPSCs from which the V2a interneurons were derived, or compared to non-V2a interneuron cells (e.g., motoneurons or other interneurons) that can be derived from the same progenitor cells as the V2a interneurons. Individual V2a interneuron generated from hPSCs may be identified, e.g., using flow cytometry, based on elevated CHX10 expression among the population of cells cultured according to methods of the present disclosure, and may be referred to as a "CHX10+ cell". In some embodiments, the population of cells that include V2a interneurons generated from culturing hPSCs according to methods of the present disclosure may have an at least 10 fold higher, e.g., at least 50 fold higher, at least 100 fold higher, at least 500 fold higher, including at least 1,000 fold higher measured level of CHX10 expression compared to the undifferentiated hPSCs from which the V2a interneurons were derived, or compared to non-V2a interneuron cells (e.g., motoneurons or other interneurons) that can be derived from the same progenitor cells as the V2a interneurons.

SOX14 (Gene ID: 8403) may be a marker for cells committed to the V2a interneuron cell fate. Thus in some embodiments, V2a interneurons generated from hPSCs according to methods of the present disclosure express SOX14 at a level higher than the level of expression of SOX14 in undifferentiated hPSCs from which the V2a interneurons were derived, or compared to non-V2a interneuron cells (e.g., motoneurons or other interneurons) that can be derived from the same progenitor cells as the V2a interneurons. Individual V2a interneuron generated from hPSCs may be identified, e.g., using flow cytometry, based on elevated SOX14 expression among the population of cells cultured according to methods of the present disclosure, and may be referred to as a "SOX14+ cell". In some embodiments, the population of cells that include V2a interneurons generated from culturing hPSCs according to methods of the present disclosure may have an at least 5 fold higher, e.g., at least 10 fold higher, at least 50 fold higher, at least 100 fold higher, including at least 1,000 fold higher measured level of SOX14 protein or RNA transcript compared to a population of undifferentiated hPSCs from which the V2a interneurons were derived, or compared to a population of non-V2a interneuron cells (e.g., motoneurons or other interneurons) that can be derived from the same progenitor cells as the V2a interneurons.

FOXN4 (Gene ID: 121643) may be a marker for spinal progenitor cells that can give rise to cells committed to the V2a interneuron cell fate. Thus in some embodiments, V2a interneurons generated from hPSCs according to methods of the present disclosure express FOXN4 at a level higher than the level of expression of FOXN4 in undifferentiated hPSCs from which the V2a interneurons were derived, or compared to cells that do not share the same spinal progenitor cells. Individual V2a interneuron generated from hPSCs may be identified, e.g., using flow cytometry, based on elevated FOXN4 expression among the population of cells cultured according to methods of the present disclosure, and may be referred to as a "FOXN4+ cell". In some embodiments, the population of cells that include V2a interneurons generated from hPSCs according to methods of the present disclosure may have an at least 5 fold higher, e.g., at least 10 fold higher, at least 50 fold higher, including at least 100 fold higher measured level of FOXN4 expression compared to the undifferentiated hPSCs from which the V2a interneurons were derived.

LHX3 (Gene ID: 8022) may be a marker for spinal progenitor cells that can give rise to cells committed to the V2a interneuron cell fate. Thus in some embodiments, V2a interneurons generated from hPSCs according to methods of the present disclosure express LHX3 at a level higher than the level of expression of LHX3 in undifferentiated hPSCs from which the V2a interneurons were derived, or compared to non-V2a interneuron cells (e.g., motoneurons or other interneurons) that can be derived from the same progenitor cells as the V2a interneurons. Individual V2a interneuron generated from hPSCs may be identified, e.g., using flow cytometry, based on elevated LHX3 expression among the population of cells cultured according to methods of the present disclosure, and may be referred to as a "LHX3+ cell". In some embodiments, the population of cells that include V2a interneurons generated from hPSCs, according to methods of the present disclosure, may have at least 5 fold higher, e.g., at least 10 fold higher, at least 50 fold higher, including at least 100 fold higher measured level of expression of LHX3 protein or RNA transcript compared to the undifferentiated hPSCs from which the V2a interneurons were derived.

GATA3 (Gene ID: 2625) may be a marker for cells differentiated from spinal progenitor cells of V2a interneurons, but that are committed to a non-V2a interneuron cell fate, e.g., committed to a V2b interneuron cell fate. In some cases, the population of cells that include V2a interneurons generated from hPSCs, according to methods of the present disclosure, may have 10 fold or less, e.g., 5 fold or less, 4 fold or less, 3 fold or less, including 2 fold or less increase in the measured level of expression of GATA3 protein or RNA transcript compared to the undifferentiated hPSCs from which the V2a interneurons were derived.

HB9 (also known as MNX1; Gene ID: 3110) may be a marker for cells committed to a non-V2a interneuron cell fate, e.g., committed to a spinal cord motoneuron cell fate. In some cases, the population of cells that include V2a interneurons generated from hPSCs according to methods of the present disclosure may have 10 fold or less, e.g., 5 fold or less, 4 fold or less, 3 fold or less, including 2 fold or less increase in the measured level of expression of HB9 protein or RNA transcript compared to the undifferentiated hPSCs from which the V2a interneurons were derived.

In some cases, the increase in the measured level of expression of V2a interneuron markers in a population of cells including V2a interneurons generated according to methods of the present disclosure, when compared to the undifferentiated hPSCs from which the V2a interneurons are derived, is at least 5 fold higher, e.g., at least 10 fold higher, at least 20 fold higher, at least 50 fold higher, at least 100 fold higher, at least 500 fold higher, including at least 1,000 fold higher than the increase in the measured level of expression of markers that are not specific to V2a interneurons (e.g., makers for spinal progenitor cells of the V2a interneurons, or for non-V2a descendants of the spinal progenitor cells). V2a interneuron-specific markers of interest include, e.g., CHX10. Non-V2a interneuron-specific markers of interest include GATA3, HB9 and PAX6 (Gene ID: 5080).

In some cases, the increase in level of expression of neuronal markers in a population of cells that include V2a interneurons, generated according to methods of the present disclosure, when compared to the undifferentiated hPSCs from which the V2a interneurons are derived, is at least 5 fold higher, e.g., at least 10 fold higher, at least 20 fold higher, including at least 50 fold higher, than the increase in expression of non-neuronal markers (e.g., markers for glial or retinal cell types). Neuronal markers of interest include NF and βIII tubulin. Glial markers of interest include PDFGRA (Gene ID: 5156), CSPG4 (Gene ID: 1464), SOX10 (Gene ID: 6663) and GFAP (Gene ID: 2670).

Retinal markers of interest include THY1 (Gene ID: 7070), IRBP (also known as RBP3; Gene ID: 5949) and CRX (Gene ID: 1406).

The present disclosure provides efficient methods of generating V2a interneurons from hPSCs. Thus, in some embodiments, about 10% or more, e.g., about 20% or more, about 30% or more, about 40% or more, including about 50% or more of the cells after culturing in the neural induction medium (e.g., after culturing in the last of multiple neural induction media, as described further below), according to methods of the present disclosure are CHX10+ cells. In some embodiments, the percentage of CHX10+ cells among the cells after culturing in the neural induction medium (e.g., after culturing in the last of multiple neural induction media, as described further below), according to methods of the present disclosure is from about 10% to about 60%, e.g., from about 20% to about 55%, including from about 25 to about 50%. In some cases, the average number of CHX10+ cells generated per input hPSC cell is about 5 or more, e.g., about 7 or more, about 10 or more, about 12 or more, including about 15 or more. In some embodiments, the average number of CHX10+ cells generated per input hPSC cell is from about 5 to about 25, e.g., from about 7 to about 20, including from about 10 to about 15.

In some embodiments, about 30% or more, e.g., about 35% or more, about 40% or more, including about 45% or more of the cells after culturing in the neural induction medium (e.g., after culturing in the last of multiple neural induction media, as described further below), according to methods of the present disclosure are LHX3+ cells. In some embodiments, the percentage of LHX3+ cells among the cells after culturing in the neural induction medium (e.g., after culturing in the last of multiple neural induction media, as described further below), according to methods of the present disclosure is from about 30% to about 60%, e.g., from about 40% to about 55%, including from about 45 to about 55%.

Also provided herein are V2a interneurons that are CHX10+ cells, e.g., cells committed to the V2a interneuron cell fate, derived from the hPSCs in vitro, and further cultured under suitable conditions, as described below, to exhibit functional properties of mature neurons. The mature V2a interneurons may exhibit any number of properties that are indicative of neurons. The neuronal properties include, e.g., electrophysiological activity, expression of neuron-related genes, extension of neurites, and localization of synaptic markers to neurites. Electrophysiologically active cells may be electrically excitable, and may include spontaneous electrophysiological activity, e.g., as measured by calcium imaging using a calcium indicator, or induced electrophysiological activity, e.g., as measured by action potential firing induced by injection of current through the cell using an electrode.

V2a interneurons may further reduce expression of CHX10 over time while being cultured in a neural maturation medium. Thus in some embodiments, a population of cells containing mature V2a interneurons has lower expression of CHX10 (e.g., lower percentage of CHX10+ cells) than a population of cells containing V2a interneurons derived from hPSCs at the end of culturing in a neural induction medium.

In some cases, mature V2a interneurons fire action potentials in response to a current injection (e.g., a current injection of 20 pA) at a maximum rate of about 1.0/second(s) or more, e.g., about 2.0/s or more, 3.0/s or more, 5.0/s or more, 10/s or more, including 15/s or more.

In some cases, both CHX10 and a gene related to neurons may be expressed by V2a interneurons as they mature. Suitable neuron-related genes may include, e.g., the vesicular glutamate transporter (e.g., VGlut1) and NeuN (also known as Rbfox3). Mature V2a interneurons expressing CHX10 may not express genes related to GABA release.

Synaptic markers of interest may include, e.g., a postsynaptic marker, such as GRIP1, or a presynaptic marker, such as synaptophysin.

Methods

Methods of Generating V2a Interneurons from hPSC Cells

A method of the present disclosure may include culturing hPSCs in vitro in a neural induction medium that includes a retinoic acid signaling pathway activator (e.g., a retinoic acid receptor agonist, such as retinoic acid), a sonic hedgehog (Shh) signaling pathway activator (e.g., a Smoothened agonist, such as purmorphamine); and a Notch signaling pathway inhibitor (e.g., a γ secretase inhibitor, such as N-[(3,5-difluorophenyl)acetyl]-L-alanyl-2-phenyl]glycine-1,1-dimethylethyl ester (DAPT)), in a manner sufficient to induce differentiation of the hPSCs into CHX10-expressing (CHX10+) cells (e.g., CHX10+ V2a interneurons). As V2a interneurons are derived from neural ectoderm progenitor cells, for the purpose of this disclosure, "hPSCs" is meant to include, unless indicated otherwise, hPSCs that have at least partially differentiated into neural ectoderm progenitor cells, e.g., by culturing the population of hPSCs in an early differentiation medium that includes Small Mothers Against Decapentaplegic (SMAD) inhibitors, as described further below.

The retinoic acid signaling pathway activator may be any suitable molecule (polypeptide, small molecule, nucleic acid, etc.) that activates the retinoic acid signaling pathway. The retinoic acid signaling pathway may be activated by using agonists of the retinoic acid receptor (RAR) such as retinoic acid. Retinoic acid acts by binding to the retinoic acid receptor (RAR), which is bound to DNA as a heterodimer with the retinoid X receptor (RXR) in regions called retinoic acid response elements (RAREs). Binding of the retinoic acid ligand to RAR alters the conformation of the RAR, which affects the binding of other proteins that either induce or repress transcription of nearby genes, for example of Hox genes. Retinoic acid signaling pathway activators include retinoic acid receptor agonists, such as retinoic acid, and derivatives thereof. Suitable retinoic acid signaling pathway activators include, without limitation, all-trans retinoic acid, synthetic retinoid ec23, Ch55, TTNPB, fenretinide, AC261066, adapalene, AC55649, AM80, AM580, BMS 753, and tazarotene.

The Shh signaling pathway activator may be any suitable molecule (polypeptide, small molecule, nucleic acid, etc.) that activates the Shh signaling pathway. Shh signals by interacting with a plasma membrane complex of Patched (Ptc) and Smoothened (Smo) that transduce the Shh signal into the cell. Ptc is considered to repress Shh signaling by binding to Smo in the cell membrane. In the presence of Shh ligand, this repression is relieved and Smo is able to signal. In vertebrates, the zinc finger proteins GN1, GN2 and GN3 are downstream mediators of Shh signaling and are involved in controlling the transcriptional response of target genes in a Shh dependent manner. Shh signaling pathway activators include Smoothened agonists. Suitable Smoothened agonists include, without limitation, SAG (9-Cyclohexyl-N-[4-(4-morpholinyl)phenyl]-2-(1-naphthalenyloxy)-9H-purin-6-amine); purmorphamine (9-Cyclohexyl-N-[4-(4-morpholinyl)phenyl]-2-(1-naphthalenyloxy)-9H-purin-6-amine); and 20(S)-hydroxycholesterol.

The Notch signaling pathway inhibitor may be any suitable molecule (polypeptide, small molecule, nucleic acid, etc.) that inhibits signaling mediated by activation of a Notch receptor. Ligand-induced activation of Notch results in cleavage at the S2 site by proteases of the ADAM family, releasing the extracellular domain. The remaining truncated transmembrane form of Notch is then subject to cleavage at two sites within the membrane S3 and S4, the targets of γ-secretase. Notch intracellular domain (ICD) translocates to the nucleus where it regulates transcription of Notch target genes. Notch signaling pathway inhibitors include inhibitors of Notch receptor activation, e.g., Notch receptor antagonists. In some cases, the inhibitor of Notch receptor activation is a γ-secretase inhibitor, including, but not limited to, N-[(3,5-difluorophenyl)acetyl]-L-alanyl-2-phenyl]glycine-1,1-dimethylethyl ester (DAPT); N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-L-alaninamide (LY411575); L-685,458; BMS-299897; MK0752; and MRK-003. Other inhibitors of the Notch signaling pathway include, without limitation, anti-Notch antibodies and antigen-binding fragments thereof as well as inhibitory nucleic acids (e.g., small interfering RNAs, antisense oligonucleotides, and morpholino oligos).

The neural induction medium may be any suitable media that promotes differentiation of hPSCs into neuronal cell types. The neural induction medium may include a base medium and one or more supplements. Suitable base media include, without limitation, Dulbecco's Modified Eagle's Medium (DMEM), Ham's F12, KODMEM medium (Knockout Dulbecco's Modified Eagle's Medium), RPMI 1640 and MEM. Suitable supplements include, without limitation, N2 supplement, L-glutamine, heparin, non-essential amino acids, antibiotics (e.g., penicillin-streptoycin, ascorbic acid, and brain derived neurotrophic factor (BDNF). Other suitable media include Neurobasal™ medium and NSC™ from Life Technologies, PNGM™ from Lonza, Neural Stem Cell basal medium from Millipore and Stemdiff™ from StemCell Technologies.

In this paragraph, and throughout the specification, unless the context clearly indicates otherwise, reference to "a" or "the" retinoic acid signaling pathway activator is considered to include as an example thereof a retinoic acid receptor agonist, e.g., retinoic acid. The amount of the retinoic acid signaling pathway activator present in the neural induction medium may be an amount suitable to differentiate hPSCs into V2a interneurons. In some cases, the retinoic acid signaling pathway activator is added to the neural induction medium at a known concentration. In some cases, the retinoic acid signaling pathway activator is present in the neural induction medium at a concentration of about 20 nM or more, e.g., about 30 nM or more, about 40 nM or more, including about 50 nM or more, and in some cases of about 500 nM or less, e.g., about 400 nM or less, about 300 nM or less, including about 200 nM or less. In some cases, the retinoic acid signaling pathway activator is present in the neural induction medium at a concentration of from about 20 nM to about 500 nM, e.g., from about 30 nM to about 400 nM, from about 40 nM to about 300 nM, including from about 50 nM to about 200 nM. In some embodiments, the retinoic acid signaling pathway activator is present in the neural induction medium at a concentration of about 100 nM. In some embodiments, the concentration of the retinoic acid signaling pathway activator in the neural induction medium may be different at different times during the culturing.

In this paragraph, and throughout the specification, unless the context clearly indicates otherwise, reference to "a" or "the" Shh signaling pathway activator is considered to include as an example thereof a Smoothened agonist, e.g., purmorphamine. The amount of the Shh signaling pathway activator present in the neural induction medium may be an amount suitable to differentiate hPSCs into V2a interneurons. In some cases, the Shh signaling pathway activator is added to the neural induction medium at a known concentration. In some cases, the Shh signaling pathway activator is present in the neural induction medium at a concentration of about 20 nM or more, e.g., about 30 nM or more, about 40 nM or more, including about 50 nM or more, and in some cases of about 500 nM or less, e.g., about 400 nM or less, about 300 nM or less, about 250 nM or less, about 225 nM or less, about 200 nM or less, about 175 nM or less, including about 150 nM or less. In some cases, the Shh signaling pathway activator is present in the neural induction medium at a concentration of from about 20 nM to about 500 nM, e.g., from about 30 nM to about 400 nM, from about 30 nM to about 300 nM, from about 40 nM to about 250 nM, from about 40 nM to about 225 nM, from about 40 nM to about 200 nM, from about 50 nM to about 175 nM, including from about 50 nM to about 150 nM. In some embodiments, the Shh signaling pathway activator is present in the neural induction medium at a concentration of about 100 nM. In some embodiments, the concentration of the Shh signaling pathway activator in the neural induction medium may be different at different times during the culturing In this paragraph, and throughout the specification, unless the context clearly indicates otherwise, reference to "a" or "the" Notch signaling pathway inhibitor is considered to include as an example thereof a γ secretase inhibitor, e.g., DAPT. The amount of the Notch signaling pathway inhibitor present in the neural induction medium may be an amount suitable to differentiate hPSCs into V2a interneurons. In some cases, the Notch signaling pathway inhibitor is added to the neural induction medium at a known concentration. In some cases, the Notch signaling pathway inhibitor is present in the neural induction medium at a concentration of about 250 nM or more, e.g., about 350 nM or more, about 500 nM or more, including about 750 nM or more, and in some cases of about 10 µM or less, e.g., about 5.0 µM or less, about 3.0 µM or less, including about 2.0 µM or less. In some cases, the Notch signaling pathway inhibitor is present in the neural induction medium at a concentration of from about 250 nM to about 10 µM, e.g., from about 350 nM to about 5.0 µM, from about 500 nM to about 5.0 µM, including from about 750 nM to about 3.0 µM. In some embodiments, the Notch signaling pathway inhibitor is present in the neural induction medium at a concentration of about 1 µM. In some embodiments, the concentration of the Notch signaling pathway inhibitor in the neural induction medium may be different at different times during the culturing.

Figure 1B:
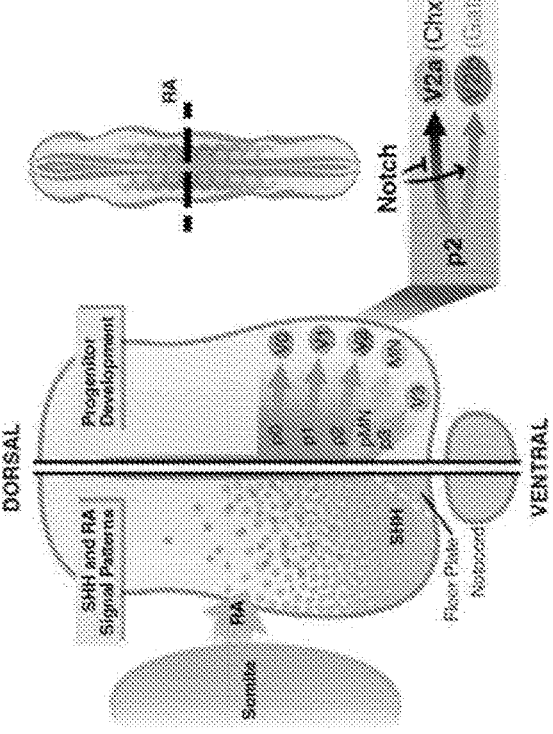

Culturing the hPSCs in a neural induction medium, according to methods of the present disclosure, may include using multiple neural induction media over the time course of differentiating the hPSCs (see, e.g., FIG. 1B). Aspects of the culturing may include contacting a population of hPSCs with a first neural induction medium that includes a retinoic acid signaling pathway activator for a first time period, then contacting the cells with a second neural induction medium that includes the retinoic acid signaling pathway activator, a Shh signaling pathway activator, and a Notch signaling pathway inhibitor for a second time period. Aspects of the culturing may include contacting a population of hPSCs with a first neural induction medium that includes a retinoic acid signaling pathway activator but not a Shh signaling pathway activator for a first time period, then contacting the cells with a second neural induction medium that includes the retinoic acid signaling pathway activator and the Shh signaling pathway activator for a second time period, and then contacting the cells with a third neural induction medium that includes the retinoic acid signaling pathway activator, the Shh signaling pathway activator, and the Notch signaling pathway inhibitor.

In some embodiments, the Notch signaling pathway inhibitor is added to the neural induction medium after initiating the differentiation of hPSCs using the retinoic acid signaling pathway activator. Thus, in some cases, the Notch signaling pathway inhibitor is not added to the first neural induction medium, and is added to the second neural induction medium together with the Shh signaling pathway activator. In other words, in some embodiments, culturing hPSCs includes contacting a population of hPSCs with a first neural induction medium that includes a retinoic acid signaling pathway activator but not a Shh signaling pathway activator or a Notch signaling pathway inhibitor for a first time period, then contacting the cells with a second neural induction medium that includes the retinoic acid signaling pathway activator, the Shh signaling pathway activator, and the Notch signaling pathway inhibitor for a second time period.

One or more of the neural induction media described herein may include a Wnt signaling activator, e.g., a small molecule Wnt signaling activator, such as a GSK3 inhibitor, such as a small molecule GSK3 inhibitor, e.g., CHIR99021 (6-[[2-[[4-(2,4-Dichlorophenyl)-5-(5-methyl-1H-imidazol-2-yl)-2-pyrimidinyl]amino]ethyl]amino]-3-pyridinecarbonitrile). Additional Wnt signaling activators which may be used in connection with the disclosed methods include: CHIR 99021 trihydrochloride (6-[[2-[[4-(2,4-Dichlorophenyl)-5-(5-methyl-1H-imidazol-2-yl)-2-pyrimidinyl]amino]ethyl]amino]-3-pyridinecarbonitrile trihydrochloride), WAY-316606 (5-(Phenylsulfonyl)-N-4-piperidinyl-2-(trifluoromethyl)benzene sulfonamide hydrochloride), (hetero)arylpyrimidines, IQ1 (2-[2-(4-Acetylphenyl)diazenyl]-2-(3,4-dihydro-3,3-dimethyl-1(2H)-isoquinolinylidene)acetamide), QS11 ((2S)-2-[2-(Indan-5-yloxy)-9-(1,1'-biphenyl-4-yl)methyl)-9H-purin-6-ylamino]-3-phenyl-propan-1-ol), SB-216763 (3-(2,4-Dichlorophenyl)-4-(1-methyl-1H-indol-3-yl)-1H-pyrrole-2,5-dione), BIO(6-bromoindirubin-3'-oxime), LY2090314 (3-(9-fluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione), DCA (Sodium dichloroacetate), 2-amino-4-[3,4-(methylenedioxy)benzyl-amino]-6-(3-methoxyphenyl)pyrimidine. The Wnt signaling activator may be present in any suitable concentration in the neural induction medium and may be introduced at any suitable time during the differentiation. For example, the Wnt signaling activator may be present in the neural induction medium at a concentration of from about 0.1 µM to about 10 µM, e.g., from about 1 µM to about 5 µM, such as about 2 µM. Use of a Wnt signaling activator may be of interest, for example, when it is desired to shift the rostral/caudal identity of the cell population, e.g., to increase the percentage of cells exhibiting a caudal phenotype. In addition, the introduction of a Wnt signaling activator appears to increase the percentage of CHX10$^+$ cells in the population.

In some embodiments, the Notch signaling pathway inhibitor is added to the neural induction medium after initiating the differentiation of hPSCs using the retinoic acid signaling pathway activator and the Shh signaling pathway activator. Thus, in some cases, the Notch signaling pathway inhibitor is not added to the first or the second neural induction media, and is added to the third neural induction medium. In some embodiments, the Notch signaling pathway inhibitor is added to the neural induction medium at the same time as the retinoic acid signaling pathway activator is added to the neural induction medium. Thus, in some cases, the Notch signaling pathway inhibitor is added to the first and the second neural induction media.

"Contacting" may refer to any suitable method of immersing and/or exposing a population of cells growing on a substrate, or in suspension, with the medium. In some cases, the contacting includes adding the medium to a compartment that includes the population of cells, and leaving the cells in the medium for the period of time. In some cases, the contacting includes continuously adding the medium to the compartment that includes the population of cells, e.g., as a flow of the medium over the cells.

The first time period, e.g., as set out in any embodiment set forth herein, and specifically those set forth above, may be about one day or more, e.g., about 2 days or more, including about 3 days or more, and in some cases, may be about 1 day, about 2 days, or about 3 days. The second time period, e.g., as set out in any embodiment set forth herein, and specifically those set forth above, may be about one day or more, e.g., about 2 days or more, about 3 days or more, about 4 days or more, about 5 days or more, about 6 days or more, about 7 days or more, about 8 days or more, about 9 days or more, including about 10 days or more, and in some cases, may be about 1 day, about 2 days, about 3 days, about 4 days, about 5 days, about 6 days, about 7 days, about 8 days, about 9 days, or about 10 days. The third time period, e.g., as set out in any embodiment set forth herein, and specifically those set forth above, may be about 5 days or more, e.g., about 6 days or more, including about 7 days or more, and in some cases, may be about 5 days, about 6 days, or about 7 days. In some embodiments, the first time period is about 2 days, the second time period is about 3 days, and the third time period is about 7 days.

The culturing in the neural induction medium (i.e., all of the one or more neural induction media) may take any suitable total number of days to differentiate the hPSCs into the V2a interneurons, according to the methods disclosed herein. In some cases, the hPSCs are cultured in the neural induction medium for about 7 days or more, e.g., about 9 days or more, about 11 days or more, including about 12 days or more, and in some cases, about 13 days or less, e.g., about 12 days or less, including about 11 days or less. In some embodiments, the hPSCs are cultured in the neural induction medium for from about 7 days to about 13 days, e.g., from about 9 days to about 13 days, including about 11 days to about 13 days. In some embodiments, the hPSCs are cultured in the neural induction medium for about 12 days.

Culturing the hPSCs, according to aspects of the present disclosure, may further include any suitable methods for promoting differentiation of a population of hPSCs into neural ectoderm progenitor cells (i.e., progenitor cells that can give rise to neuronal cell types and progenitors thereof; including progenitor cells that can give rise to spinal cord neuron progenitors). In general, this may involve inhibiting signaling of the Small Mothers Against Decapentaplegic (SMAD) signaling pathway in the hPSCs. Thus, the present methods may include, in addition to the steps discussed previously herein, culturing hPSCs in conditions sufficient to promote neural ectoderm differentiation of the hPSCs, by adding one or more, e.g., two or more, SMAD signaling pathway inhibitor to the medium in which the hPSCs are cultured. In some cases, the SMAD signaling pathway inhibitor(s) is/are added to the neural induction medium. In some embodiments, the neural induction medium (e.g., the first neural induction medium) includes the SMAD signaling pathway inhibitor(s) and the retinoic acid signaling pathway activator (e.g., a retinoic acid receptor agonist, such as retinoic acid), but not the Shh signaling pathway activator. In some embodiments, the method include culturing the hPSCs in an early differentiation medium that includes the SMAD signaling pathway inhibitor(s), but does not include the retinoic acid signaling pathway activator, the Shh signaling pathway activator or the Notch signaling pathway inhibitor.

The early differentiation medium may be any suitable medium to promote differentiation of the hPSCs into neural ectoderm progenitor cells. In some cases, the early differentiation medium is a serum-free defined medium for feeder-free culture of stem cells. The early differentiation medium may be mTeSR™ 1, KSR (Invitrogen), or xeno-free KSR (Invitrogen), StemPro® (Invitrogen) and HESc-GRO (Millipore), DMEM based media, and the like. The early differentiation medium may include an inhibitor of p160-Rho-associated coiled kinase (ROCK). The ROCK inhibitor may be any suitable inhibitor of the kinase, such as, but not limited to, Y-27632.

The SMAD signaling pathway inhibitor(s) may be any suitable molecule (polypeptide, small molecule, nucleic acid, etc.) that inhibits SMAD signaling pathways. In some cases, the SMAD signaling pathway inhibitor includes an inhibitor of activin receptor-like kinases (ALKs), such as, but not limited to, LDN193189, SB431542, or a combination thereof. In some embodiments, the SMAD signaling pathway inhibitors comprise LDN193189, dorsomophorine, or noggin, and SB431542.

The early differentiation medium may include a Wnt signaling activator, e.g., a small molecule Wnt signaling activator, such as a GSK3 inhibitor, such as a small molecule GSK3 inhibitor, e.g., CHIR99021 (6-[[2-[[4-(2,4-Dichloro-phenyl)-5-(5-methyl-1H-imidazol-2-yl)-2-pyrimidinyl] amino]ethyl]amino]-3-pyridinecarbonitrile). This may be alternatively or in addition to its inclusion in the neural induction medium as described herein. Additional Wnt signaling activators which may be used in connection with the disclosed methods include: CHIR 99021 trihydrochloride (6-[[2-[[4-(2,4-Dichlorophenyl)-5-(5-methyl-1H-imidazol-2-yl)-2-pyrimidinyl]amino]ethyl]amino]-3-pyridinecarbonitrile trihydrochloride), WAY-316606 (5-(Phenylsulfonyl)-N-4-piperidinyl-2-(trifluoromethyl)benzene sulfonamide hydrochloride), (hetero)arylpyrimidines, IQ 1 (2-[2-(4-Acetylphenyl)diazenyl]-2-(3,4-dihydro-3,3-dimethyl-1 (2H)-isoquinolinylidene)acetamide), QS11 ((2S)-2-[2-(In-dan-5-yloxy)-9-(1,1'-biphenyl-4-yl)methyl)-9H-purin-6-ylamino]-3-phenyl-propan-1-ol), SB-216763 (3-(2,4-Dichlorophenyl)-4-(1-methyl-1H-indol-3-yl)-1H-pyrrole-2, 5-dione), BIO(6-bromoindirubin-3'-oxime), LY2090314 (3-(9-fluoro-2-(piperidine-1-carbonyl)-1,2,3,4-tetrahydro-[1,4] diazepino[6,7,1-hi]indol-7-yl)-4-(imidazo[1,2-a]pyridin-3-yl)-1H-pyrrole-2,5-dione), DCA (Sodium dichloroacetate), 2-amino-4-[3,4-(methylenedioxy)benzyl-amino]-6-(3-methoxyphenyl)pyrimidine. The Wnt signaling activator may be present in any suitable concentration in the early differentiation medium and may be introduced at any suitable time during the differentiation. For example, the Wnt signaling activator may be present in the early differentiation medium at a concentration of from about 0.1 µM to about 10 µM, e.g., from about 1 µM to about 5 µM, such as about 2 µM. Use of a Wnt signaling activator may be of interest, for example, when it is desired to shift the rostral/caudal identity of the cell population, e.g., to increase the percentage of cells exhibiting a caudal phenotype. In addition, the introduction of a Wnt signaling activator appears to increase the percentage of CHX10$^+$ cells in the population.

For example, a suitable early differentiation medium protocol may include seeding hPSCs at a high density, e.g., about 100K cells/cm$^2$ to about 150K cells/cm$^2$, such as about 110K cells/cm$^2$ to about 130K cells/cm$^2$, such as about 120K cells/cm$^2$, in the presence of a Wnt signaling activator, e.g., a Wnt signaling activator as described herein, e.g., at a concentration as described herein. The early differentiation medium protocol may include a step of dissociating and re-plating the cells at a lower density, e.g., about 15K cells/cm$^2$ to about 30K cells/cm$^2$, such as about 25K cells/cm$^2$. The culturing protocol may then proceed as otherwise described herein.

Culturing in the hPSCs in the early differentiation medium may be continued for any suitable amount of time to promote differentiation of a population of hPSCs into neural ectoderm progenitor cells. In some cases, the hPSCs are cultured in the early differentiation medium for about 4 to about 6 days, such as about 5 days.

The total time the hPSCs are cultured in vitro (i.e., the total time in the early differentiation medium and one or more neural induction media) to generate a population of V2a interneurons may vary, depending on the length of time the cells are cultured in each medium. In some embodiments, the total time the hPSCs are cultured in vitro is about 13 days or more, e.g., about 15 days or more, about 16 days or more, including about 17 days or more, and in some cases, about 25 days or less, e.g., about 23 days or less, about 21 days or less, about 19 days or less, about 18 days or less, including about 17 days or less. In some embodiments, the hPSCs are cultured in vitro in the early differentiation medium and one or more neural induction media for a total of from about 13 days to about 25 days, e.g., from about 15 days to about 23 days, from about 15 days to about 21 days, from about 15 days to about 19 days, including from about 16 days to about 18 days, wherein exposure to the early differentiation medium and the one or more neural induction media may be for sequential or co-extensive periods of time. In some embodiments, the hPSCs are cultured in the early differentiation medium and one or more neural induction media for about 17 days, wherein exposure to the early differentiation medium and the one or more neural induction media may be for sequential or co-extensive periods of time.

Culturing the hPSCs, according to any of the methods of the present disclosure, may include seeding the culture (e.g., a cell culture substrate) with an initial population of hPSCs. Thus, once seeded, the culturing of the hPSCs to induce differentiation of V2a interneurons (including promoting differentiation of the neural ectoderm progenitors) may not involve dissociating the cells from the cell culture substrate, once the cells are seeded and attached to the cell culture substrate. The initial population of hPSCs may include any suitable number of hPSCs to obtain a suitable density of hPSCs on the substrate. In some cases, the hPSCs are seeded on the cell culture substrate at a density of 5,000 cells/cm$^2$ or more, e.g., 10,000 cells/cm$^2$ or more, 15,000 cells/cm$^2$ or more, including 20,000 cells/cm$^2$ or more, and in some cases, at a density of 120,000 cells/cm$^2$ or less, e.g., 100,000 cells/cm$^2$ or less, 80,000 cells/cm$^2$ or less, 60,000 cells/cm$^2$ or less, 40,000 cells/cm$^2$ or less, including 30,000 cells/cm$^2$ or less. In some embodiments, the hPSCs are seeded on the cell culture substrate at a density of from 5,000 cells/cm$^2$ to 120,000 cells/cm$^2$, e.g., from 10,000 cells/cm$^2$ to 100,000 cells/cm², from 15,000 cells/cm² to 60,000 cells/cm², including from 20,000 cells/cm² to 30,000 cells/cm², e.g., about 25,000 cells/cm².

A further aspect of the present disclosure includes an in vitro method for inducing maturation of the V2a interneurons generated from hPSCs in the neural induction medium (e.g., the population of CHX10+ V2a interneurons after culturing in the last of multiple neural induction media, as described above), by reseeding cells of the population of cells that includes the V2a interneurons onto another substrate (e.g., a neural maturation substrate), and culturing the seeded cells in a neural maturation medium. The reseeding may include dissociating the cells from the substrate (i.e., the neural induction substrate) on which the hPSCs were differentiated by exposure to the neural induction medium, using any suitable method. The cells may be dissociated, by, without limitation, enzymatic and/or mechanical dissociation methods.

The population of cells that includes the V2a interneurons derived from hPSCs may be reseeded at any suitable density. In some embodiments, the cells are reseeded at a density of about 50,000 cells/cm² to about 150,000 cells/cm², such as at about 100,000 cells/cm².

The maturation process may also include culturing the reseeded cells in the neural induction medium that includes the retinoic acid signaling pathway activator (e.g., a retinoic acid receptor agonist, such as retinoic acid), the Shh signaling pathway activator (e.g., a Smoothened agonist, such as purmorphamine); and the Notch signaling pathway inhibitor (e.g., a γ secretase inhibitor, such as DAPT), as well as a ROCK inhibitor, such as Y-27632, for a time period before culturing in the neural maturation medium. Thus, in some cases, methods of the present disclosure includes, after generating a population of cells that include V2a interneurons from hPSCs in the neural induction medium, reseeding the population of cells onto a substrate, contacting the reseeded cells with a neural induction medium with the retinoic acid signaling pathway activator, the Shh signaling pathway activator, the Notch signaling pathway inhibitor, and the ROCK inhibitor, and followed by contacting with the neural maturation medium. The reseeded cells may be left in the neural induction medium for any suitable length of time, and in some cases may be in the neural induction medium for about 2 to 4 days, such as about 3 days. The cells may be in the neural maturation medium for any suitable length of time to induce maturation of the V2a interneurons, and in some cases may be in the neural induction medium for about 20 days or more, e.g., about 25 days or more, about 30 days or more, about 40 days or more, about 50 days or more, about 60 days or more, including about 100 days or more.

The neural maturation medium may be any suitable medium for promoting maturation of the V2a interneurons. Suitable media include, without limitation, Neurobasal™ medium and NSC™ from Life Technologies, PNGM™ from Lonza, Neural Stem Cell basal medium from Millipore and Stemdiff™ from StemCell Technologies. The neural maturation medium may be supplemented with any suitable supplements, such as, without limitation, B27 supplement, and neuronal growth factors. Suitable growth factors include, without limitation, BDNF, glial cell line-derived neurotrophic factor (GDNF), ciliary neurotrophic factor (CNTF), and insulin-like growth factor (IGF).

The hPSCs may be cultured in vitro using any suitable cell culture substrate for differentiating hPSCs into V2a interneurons. In some cases, the substrate is a substantially flat, two-dimensional substrate, e.g., a surface of a culture flask. The substrate may be of any suitable material for culturing cells, e.g., plastic, such as polystyrene; glass; etc. Alternatively, any suitable three-dimensional substrate, such as a hydrogel, porous scaffold, etc., may be used. In some embodiments, the substrate is coated with a suitable coating material for promoting hPSC differentiation into V2a interneurons. In some cases, the substrate is coated with extracellular matrix components, such as, but not limited to, Matrigel®, fibronectin, laminin. In some cases, the substrate may include a coating of, without limitation, polyornithine, poly-lysine, purified collagen, gelatin, fibronectin, tenascin, vitronectin, entactin, heparin sulfate proteoglycans, poly glycolytic acid (PGA), poly lactic acid (PLA), and poly lactic-glycolic acid (PLGA). The hPSCs may be cultured in adherent or suspension cell culture. For example, in some embodiments the hPSCs may be cultured as an adherent monolayer. The hPSCs may also be cultured as 3-D cell aggregates in a suitable cell culture suspension, e.g., in the absence of a scaffold material.

The hPSCs may be any suitable hPSCs for use in methods of the present disclosure. In some cases, the hPSCs are human embryonic stem cells (ESCs). Suitable human ESCs include, but are not limited to, any of a variety of available human ES lines, e.g., BG01 (hESBGN-01), BG02 (hES-BGN-02), BG03 (hESBGN-03) (BresaGen, Inc.; Athens, Ga.); SA01 (Sahlgrenska 1), SA02 (Sahlgrenska 2) (Cellartis AB; Goeteborg Sweden); ES01 (HES-1), ES01 (HES-2), ES03 (HES-3), ES04 (HES-4), ES05 (HES-5), ES06 (HES-6) (ES Cell International; Singapore); UC01 (HSF-1), UC06 (HSF-6) (University of California, San Francisco; San Francisco, Calif.); WA01 (H1), WA07 (H7), WA09 (H9), WA09/Oct4D10 (H9-hOct4-pGZ), WA13 (H13), WA14 (H14) (Wisconsin Alumni Research Foundation; WARF; Madison, Wis.). Cell line designations are given as the National Institutes of Health (NIH) code, followed in parentheses by the provider code. Embodiments of interest include any method as otherwise described herein for use in connection with H7 ESCs or H1 ESCs.

In some cases, the hPSCs are induced pluripotent stem (iPS) cells, which are a pluripotent stem cell induced from a somatic cell, e.g., a differentiated somatic cell. iPS cells are capable of self-renewal and differentiation into cell fate-committed stem cells, including neural stem cells, as well as various types of mature cells. iPS cells can be generated from somatic cells, including skin fibroblasts, using any suitable method. iPS cells can be generated from somatic cells (e.g., skin fibroblasts) by genetically modifying the somatic cells with one or more expression constructs encoding Oct-3/4 and Sox2. In some embodiments, somatic cells are genetically modified with one or more expression constructs comprising nucleotide sequences encoding Oct-3/4, Sox2, c-myc, and Klf4. In some embodiments, somatic cells are genetically modified with one or more expression constructs comprising nucleotide sequences encoding Oct-4, Sox2, Nanog, and LIN28. Suitable protein transduction methods may also be utilized, e.g., as an alternative to nucleic acid and/or virally based methods. Suitable iPS cells include WTC iPSC and WTB iPSC. Embodiments of interest include any method as otherwise described herein for use in connection with WTC iPSC and WTB iPSC.

Methods of Generating V2a Interneurons from hPSC Cells

Also provided herein is a method of producing a non-human animal model of human V2a interneuron growth and development, i.e., an in vivo model for human V2a interneuron growth and development. The method may include transplanting a population of cells that includes CHX10+ V2a interneurons (i.e., CHX10+ cells that were cultured in the neural induction medium, but not reseeded and cultured in the neural maturation medium) into a non-human animal. The population of cells may be transplanted into any suitable location within the host animal, and in some cases, may be transplanted into one or more spinal segments of the spinal cord. In each spinal segment, the population of cells may be transplanted at one or more different sites. In some cases, the population of cells is transplanted into the ventral horn of the spinal cord, where V2a interneurons from the host animal are normally found. The transplanted CHX10+ cells may develop in the host environment to acquire one or more properties of mature V2a interneurons.

The number of cells transplanted into the spinal cord may be any suitable number, and may be, e.g., $10^2$ cells/transplantation site to $10^6$ cells/transplantation site, such as $5.0 \times 10^2$ cells/transplantation site to $5.0 \times 10^5$ cells/transplantation site, $5.0 \times 10^3$ cells/transplantation site to $5.0 \times 10^5$ cells/transplantation site, or $5.0 \times 10^4$ cells/transplantation site to $5.0 \times 10^5$ cells/transplantation site, including about $1.25 \times 10^5$ cells/transplantation site.

The non-human animal may be any suitable animal, and may be a mammal. The mammal may be any suitable mammal, and may be, but is not limited to, a rodent (e.g., mouse, rat, etc.) a lagomorph (e.g., a rabbit, etc.), a feline (e.g., cat, etc.), a canine (e.g., dog, etc.), an ungulate (e.g., a pig, a cow, a horse, etc.), monkey, or a non-human primate, etc.

Also provided herein are non-human animal models that include the V2a interneurons, or a mature form thereof, derived from hPSCs according to methods of the present disclosure. The non-human animal model may be a host animal chosen from any suitable non-human animal, as described above. In some embodiments, the V2a interneurons, or the mature form thereof, are in the spinal cord, e.g., the ventral horn of the spinal cord, of the host animal.

The mature form of the V2a interneuron in the host animal may exhibit one or more properties associated with a mature V2a interneuron. In some cases, the mature V2a interneuron expresses NeuN and/or VGlut2 at a higher level than a background level of expression, e.g., as assessed by immunohistochemistry. In some embodiments, the mature form the V2a interneuron in the host has neurites (e.g., axons and/or dendrites) that extend along the rostral-caudal axis of the spinal cord. The length of the neurite along the rostral-caudal axis of the spinal cord may vary depending on, e.g., the extent of maturation of the V2a interneuron, the site of transplantation of the V2a interneuron, the time elapsed after transplantation, etc. In some cases, the neurite extends for 3 mm or more, e.g., 4 mm or more, including 5 mm or more, along the rostral-caudal axis of the spinal cord. The neurite may contain one or more functional synapses along its length. In some cases, the neurite includes one or more pre- and/or postsynaptic structures. In some cases, the presynaptic structure is associated with (e.g., juxtaposed with) a host neuron.

Utility

The present methods and animal models find use in many applications where it is desirable to understand aspects of the development and function of human V2a interneurons, and to use human V2a interneurons for regenerative cell therapies to treat central nervous system (CNS) injuries.

In some cases, the non-human animal models may be used to study how to transplant human V2a interneurons into the spinal cord in order to provide mature V2a interneurons that synapse onto postsynaptic host targets and receive synaptic input from presynaptic host neurons, and thereby establish a functional relay between the presynaptic host neuron and the postsynaptic host neuron.

In some cases, the human V2a interneurons derived from hPSCs (e.g., hESCs or iPSCs) according to the present disclosure, may be transplanted into a damaged spinal cord of a patient, where maturation of the V2a interneurons in the patient spinal cord may repair nerve damage and may restore at least some of the neurological defects associated with the damaged spinal cord.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-63 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below.

1. A method of generating spinal cord glutamatergic interneurons from a population of human pluripotent stem cells (hPSCs), comprising culturing a first population of hPSCs in vitro in a neural induction medium comprising:
   a retinoic acid signaling pathway activator;
   a sonic hedgehog (Shh) signaling pathway activator; and
   a Notch signaling pathway inhibitor,
   wherein the culturing results in generation of a second population of cultured cells comprising CHX10$^+$ V2a interneurons.
2. The method of 1, wherein the retinoic acid signaling pathway activator comprises a retinoic acid receptor agonist.
3. The method of 2, wherein the retinoic acid receptor agonist comprises retinoic acid, or a derivative thereof.
4. The method of any one of 1 to 3, wherein the Shh signaling pathway activator comprises a Smoothened agonist.
5. The method of 4, wherein the Smoothened agonist is purmorphamine, or a derivative thereof.
6. The method of any one of 1 to 5, wherein the Notch signaling pathway inhibitor comprises an inhibitor of Notch receptor activation.
7. The method of 6, wherein the inhibitor of Notch receptor activation is a Notch receptor antagonist.
8. The method of 6, wherein the inhibitor of Notch receptor activation comprises a γ-secretase inhibitor.
9. The method of 8, wherein the γ-secretase inhibitor is N-[(3,5-difluorophenyl)acetyl]-L-alanyl-2-phenyl]glycine-1,1-dimethylethyl ester (DAP T).
10. The method of any one of 1 to 9, wherein the retinoic acid signaling pathway activator is present in the neural induction medium at a concentration of from about 20 nM to about 500 nM.
11. The method of 10, wherein the retinoic acid signaling pathway activator is present in the neural induction medium at a concentration of from about 30 nM to about 300 nM.
12. The method of 11, wherein the retinoic acid signaling pathway activator is present in the neural induction medium at a concentration of about 100 nM.

13. The method of any one of 1 to 12, wherein the Shh signaling pathway activator is present in the neural induction medium at a concentration in the range of about 50 nM to about 500 nM.
14. The method of 13, wherein the Shh signaling pathway activator is present in the neural induction medium at a concentration of from about 30 nM to about 300 nM.
15. The method of 14, wherein the Shh signaling pathway activator is present in the neural induction medium at a concentration of about 100 nM.
16. The method of any one of 1 to 15, wherein the Notch signaling pathway inhibitor is present in the neural induction medium at a concentration in the range of about 250 nM to about 10 μM.
17. The method of 16, wherein the Notch signaling pathway inhibitor is present in the neural induction medium at a concentration of from about 500 nM to about 5 μM.
18. The method of 17, wherein the Notch signaling pathway inhibitor is present in the neural induction medium at a concentration of about 1 μM.
19. The method of any one of 1 to 18, wherein the culturing comprises contacting the first population of hPSCs, in order, with:
a first neural induction medium comprising the retinoic acid signaling pathway activator; and
a second neural induction medium comprising the retinoic acid signaling pathway activator, the Shh signaling pathway activator, and the Notch signaling pathway inhibitor,
under conditions sufficient to generate the second population of cultured cells comprising CHX10$^+$ V2a interneurons.
20. The method of any one of 1 to 18, wherein the culturing comprises contacting the first population of hPSCs, in order, with:
a first neural induction medium comprising the retinoic acid signaling pathway activator;
a second neural induction medium comprising the retinoic acid signaling pathway activator and the Shh signaling pathway activator; and
a third neural induction medium comprising the retinoic acid signaling pathway activator, the Shh signaling pathway activator, and the Notch signaling pathway inhibitor,
under conditions sufficient to generate the second population of cultured cells comprising CHX10$^+$ V2a interneurons.
21. The method of 20, wherein the second neural induction medium comprises the Notch signaling pathway inhibitor.
22. The method of 21, wherein the first neural induction medium comprises the Notch signaling pathway inhibitor.
23. The method of 20, wherein the first neural induction medium and the second neural induction medium do not comprise the Notch signaling pathway inhibitor.
24. The method of any one of 19 to 23, wherein contacting the first population of hPSCs with the second neural induction medium is performed about two days after contacting with the first neural induction medium.
25. The method of any one of 19 to 23, wherein the population of hPSCs is cultured for a period of 7 to 13 days after contacting with the first neural induction medium.
26. The method of any one of 19 to 24, wherein the first neural induction medium further comprises one or more SMAD signaling pathway inhibitors.
27. The method of any one of 20 to 26, wherein the second neural induction medium and the third neural induction medium do not comprise the one or more SMAD signaling pathway inhibitors.
28. The method of 26 or 27, wherein the one or more SMAD signaling pathway inhibitors is selected from Noggin, dorsomorphin, LDN193189, SB431542, or a combination thereof.
29. The method of any one of 1 to 28, wherein the first population of hPSCs is cultured on a cell culture substrate comprising a coating of extracellular matrix components.
30. The method of 29, wherein the cell culture substrate comprises a coating of Matrigel®.
31. The method of any one of 1 to 30, wherein the culturing comprises seeding the first population of hPSCs on a cell culture substrate at a density of from about 5,000 to about 120,000 cells/cm$^2$.
32. The method of any one of 1 to 31, wherein the hPSCs comprise embryonic stem cells (ESCs) or induced pluripotent stem cells (iPSCs).
33. The method of 32, wherein the hPSCs are H7 ESCs.
34. The method of 32, wherein the hPSCs are H1 ESCs.
35. The method of 32, wherein the hPSCs are WTC iPSCs.
36. The method of 32, wherein the hPSCs are WTB iPSCs.
37. The method of any one of 1 to 36, wherein 10% to 60% of the second population of cultured cells are CHX10$^+$ V2a interneurons.
38. The method of 37, wherein 20% to 40% of the second population cultured cells are CHX10$^+$ V2a interneurons.
39. The method of any one of 1 to 38, wherein 30% or more of the second population of cultured cells are LHX3$^+$.
40. The method of any one of 1 to 39, wherein gene expression in the second population of cultured cells is enriched, compared to the first population of hPSCs, for one or more genes selected from: FOXN4, CHX10, SOX14, NF Light Chain, and $\beta_{III}$ tubulin.
41. The method of any one of 1 to 40, further comprising:
reseeding at least some of the second population of cultured cells onto a neural maturation substrate; and
culturing the seeded second population of cultured cells in a neural maturation medium, thereby generating a mature population of CHX10$^+$ V2a interneurons.
42. The method of 41, wherein a V2a interneuron of the mature population is electrically excitable.
43. A non-human animal model of human V2a interneuron development, comprising a V2a interneuron produced according to the method of any one of 1 to 40, or a mature form thereof.
44. The non-human animal model of 43, wherein the animal model is a mammal.
45. The non-human animal model of 44, wherein the mammal is a rodent.
46. The non-human animal model of any one of 43 to 45, wherein a spinal cord of the animal model comprises the V2a interneuron, or the mature form thereof.
47. The non-human animal model of 46, wherein spinal cord of the animal model comprises a mature form of the V2a interneuron and the mature form of the V2a interneuron comprises a neurite extending along a rostral-caudal axis of the spinal cord.
48. The non-human animal model of 47, wherein the neurite extends at least 3 mm along the rostral-caudal axis of the spinal cord.
49. The non-human animal model of 47 or 48, wherein the neurite comprise a post- and/or presynaptic structure.
50. The non-human animal model of 49, wherein the neurite comprises a presynaptic structure associated with a host neuron.
51. The non-human animal model of any one of 43 to 50, wherein the V2a interneuron, or the mature form thereof, expresses NeuN and/or VGlut2.

52. A method of producing a non-human animal model of human V2a interneuron growth, comprising transplanting, into a non-human animal, a population of cells comprising CHX10$^+$ V2a interneurons produced according to the method of any one of claims 1 to 40.
53. The method of 52, wherein the population of cells are transplanted into the spinal cord.
54. The method of 53, wherein the population of cells are transplanted into the ventral horn of the spinal cord.
55. The method of any one of 52 to 54, wherein the population of cells is transplanted at a density of from 10$^4$ cells/transplantation site to 10$^6$ cells/transplantation site.
56. The method of any one of 52 to 55, wherein the non-human animal is a mammal.
57. The method of 56, wherein the mammal is a rodent.
58. The method of any one of 52 to 57, wherein at least some of the CHX10$^+$ V2a interneurons express VGlut2.
59. The method of any one of 1 to 42 and 52-58, or the non-human animal model of any one of 43 to 51, wherein the culturing comprises culturing the hPSCs as an adherent monolayer.
60. The method of any one of 1 to 42 and 52-59, or the non-human animal model of any one of 43 to 51, comprising freezing and subsequently thawing the second population of cultured cells comprising CHX10$^+$ V2a interneurons, wherein the freezing and thawing does not significantly affect the % of CHX10$^+$ V2a interneurons.
61. The method of any one of 1 to 42 and 52-60, or the non-human animal model of any one of 43 to 51, comprising reseeding (e.g., re-plating) at least some of the second population of cultured cells into a culture medium comprising a ROCK inhibitor (e.g., any ROCK inhibitor as described herein).
62. The method or non-human animal model of 61, wherein the ROCK inhibitor is present in the neural induction medium at a concentration of from about 0.1 µM to about 10 µM, e.g., from about 1 µM to about 5 µM.
63. The method of any one of 1 to 42 and 52-62, or the non-human animal model of any one of 43 to 51 and 62, comprising culturing the first population of hPSCs in vitro in an early differentiation medium and/or a neural induction medium comprising a Wnt signaling activator as described herein, e.g., a small molecule Wnt signaling activator, such as a small molecule GSK3 inhibitor, e.g., CHIR99021.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Materials and Methods
The following material and methods were used in the Examples.
Human Pluripotent Stem Cell Culture
hPSCs (H7 and H1 hESCs, WTC and WTB iPSCs) were grown to 70% confluency and passaged using Accutase (Accutase, San Diego, Calif.) to dissociate to single cells (incubated at 37° C. for 5 minutes). Dissociated cells were re-plated on Matrigel®-coated cultureware (hESC-qualified for ESCs and growth factor reduced for iPSCs) at a density of 10,000 cells per cm$^2$ with 10 µM ROCK inhibitor (Y-27632, Selleckchem, Houston, Tex.) in mTeSR (Stem-Cell Technologies, location).
V2a Interneuron Differentiation
hPSCs were seeded in mTeSR supplemented with 10 µM ROCK inhibitor and dual SMAD inhibitors 0.2 µM LDN193189 and 10 µM SB431542 (StemGent, Cambridge, Mass.) at 5,000-100,000 cells/cm$^2$ onto 24-well plates coated with Matrigel. On day 3, medium was changed to mTeSR supplemented with dual SMAD inhibitors only. On day 5, the base medium was switched to neural induction medium (DMEM F:12 (Corning), N2 supplement (Life Technologies, Carlsbad, Calif.), L-Glutamine (VWR), 2 µg/ml heparin (Sigma Aldrich, St. Louis, Mo.), non-essential amino acids (VWR), penicillin-streptomycin (VWR) supplemented with fresh 0.4 µg/ml ascorbic acid (Sigma Aldrich) and 10 ng/ml brain derived neurotrophin factor (BDNF, R&D Systems, Minneapolis, Minn.)) supplemented with dual SMAD inhibitors and 10 nM-10 µM retinoic acid (Sigma Aldrich). On day 7, dual SMAD inhibition was ceased and 10 nM-10 µM retinoic acid, 10 nM-10 µM pur (EMD Millipore, Darmstast, Germany) and 100 nM-10 µM N—[N-(3,5-Difluorophenacetyl)-L-alanyl]-S-phenylglycine t-butyl ester (DAPT) were added to the neural induction medium. Medium was changed every 2 to 3 days throughout the differentiation, with fresh supplements added each time for up to 17 days.
Neuronal Maturation (Protocol 1)
On day 17 of differentiation, cultures were dissociated with Accutase (45 minutes at 37° C.; triturated every 15 minutes) and plated at 100,000 cells/cm$^2$ on Matrigel-coated TCPS or glass coverslips (Warner Instruments, Hamden Conn.) in neural induction medium containing the same concentrations as before of RA, pur, and DAPT plus 10 µM ROCK inhibitor. Three days later, the medium was switch to neural maturation media (Neurobasal (Life Technologies) plus B27 supplement (Life Technologies) supplemented with 10 ng/ml of BDNF, GDNF, CNTF, and IGF). Media was completely changed every 3-4 days for the remainder of the culture duration.
Neuronal Maturation (Protocol 2)
On day 17 of differentiation, cultures were dissociated with Accutase (45 minutes at 37° C.; triturated every 15 minutes) and plated at 100,000 cells/cm$^2$ on Matrigel-coated µ-slide 8 wells (ibidi, Martinsreid, Germany) or glass coverslips (Warner Instruments, Hamden Conn.) in neural induction medium containing 100 nM RA, 100 nM pur, and 1 µM DAPT plus 10 µM ROCK inhibitor. Three days later, the medium was switched to neural maturation medium (BrainPhys plus SM1 supplement (Stemcell Technologies) supplemented with 10 ng/ml of BDNF, GDNF, CNTF, and IGF, R&D Systems). Medium was completely changed every 3-4 days for the remainder of the culture duration.
Real Time Quantitative Polymerase Chain Reaction
Samples were lysed and RNA was extracted using the E.Z.N.A. Total RNA Kit (Omega Biotek, Norcross, Ga.). RNA (500 ng) was reverse-transcribed into cDNA using the iScript cDNA synthesis kit (BioRad, Hercules, Calif.). RTqPCR was performed using Fast SYBR Green Master Mix (Life Technologies) and the primers listed in Table 1 below were annealed at 61° C. on the Step One Plus Real-Time PCR System (Life Technologies). Fold changes were calculated using the $\Delta\Delta C_t$ method. For high throughput gene expression analysis, Fluidigm was used. Preamplified cDNA samples and primers were mixed with Sso Fast EvaGreen Supermix (BioRad) then loaded onto a 96.96 Dynamic Array integrated fluidic circuit (IFC) and ran on a BioMark HD system.

TABLE 1

| Gene Symbol | Gene Description | Forward Primer Sequence | Reverse Primer Sequence |
|---|---|---|---|
| RPS18 (18s) | Ribosomal Protein S18 | CTTCCACAGGAGGCCTACAC (SEQ ID NO: 1) | CTTCGGCCCACACCCTTAAT (SEQ ID NO: 22) |
| CHX10 | Ceh-10 Homeodomain-Containing Homolog | CGGCGACACAGGACAATCTT (SEQ ID NO: 2) | CCTGTATCCTGTCTTCCGGC (SEQ ID NO: 23) |
| FOXN4 | Forkhead Box N4 | CGTACAGCTGTCTGATCGCC (SEQ ID NO: 3) | GGAGCCGCTCATCTTGTTCT (SEQ ID NO: 24) |
| GATA3 | GATA Binding Protein3 | TTGTGCTCGGAGGGTTTCTT (SEQ ID NO: 4) | CAGCACAGGCTGCAGGAATA (SEQ ID NO: 25) |
| OLIG2 | Oligodendrocyte Lineage Transcription Factor 2 | CGCATCCAGATTTTCGGGTC (SEQ ID NO: 5) | AAAAGGTCATCGGGCTCTGG (SEQ ID NO: 26) |
| HB9 | Homeobox Protein HB9 | TCTCTTAACGGGAAGGGGCA (SEQ ID NO: 6) | CTAATTCAGGGCGCTCTCGG (SEQ ID NQ.27) |
| PAX6 | Paired Box 6 | GAGCGAGCGGTGCATTTG (SEQ ID NO: 7) | TCAGATTCCTATGCTGATTGGT GAT (SEQ ID NO: 28) |
| TUBB3 ($\beta_{III}$ tubulin) | Beta 3 Class III Tubulin | GAACCCCAGGCAGCTAGAC (SEQ ID NO: 8) | ACTGATGACTTCCCAGAACTGT (SEQ ID NO: 29) |
| POU5F1 | POU Class 5 Homeobox 1 | ATGCATTCAAACTGAGGTGC CT (SEQ ID NO: 9) | AACTTCACCTTCCCTCCAACCA (SEQ ID NO: 30) |
| NES (Nestin) | Nestin | CCACCCTGCAAAGGGAATCT (SEQ ID NO: 10) | GGTGAGCTTGGGCACAAAAG (SEQ ID NO: 31) |
| SOX14 | SRY (Sex Determining Region Y)-Box 14 | GAACCCTTGCACTCCCTACC (SEQ ID NO: 11) | TCGATGTATGGCCGCTTCTC (SEQ ID NO: 32) |
| SIM1 | Single-Minded Family BHLH Transcription Factor 1 | GGCTCTCACCGGCAGTATTT (SEQ ID NO: 12) | TGAGCCATTACAGCCCAAGG (SEQ ID NO: 33) |
| RBFOX3 (NeuN) | Hexaribonucleotide Binding Protein 3 Neuronal Nuclei (NeuN) | ACGATCGTAGAGGGACGGAA (SEQ ID NO: 13) | AATTCAGGCCCGTAGACTGC (SEQ ID NO: 34) |
| NEFL (Neuro filament (NF) Light Chain) | Neurofilament (NF) Light Chain | CATCAGCGCTATGCAGGACA (SEQ ID NO: 14) | GTCTCCTCGCCTTCCAAGAG (SEQ ID NO: 35) |
| PDFGRA | Platelet-derived growth factor receptor, alpha peptide | CTGGACACTGGGAGATTCGG (SEQ ID NO: 15) | CACGGCCTCCAATGATCTCT (SEQ ID NO: 36) |
| CSPG4 | Chondroitin Sulfate Proteoglycan 4 | CACTCAGGACGAAGGAACCC (SEQ ID NO: 16) | GGAGCAATACGGTACCCTGG (SEQ ID NO: 37) |
| SOX10 | SRY (Sex Determining Region Y)-Box 10 | CACAAGAAAGACCACCCGGA (SEQ ID NO: 17) | AAGTGGGCGCTCTTGTAGTG (SEQ ID NO: 38) |
| GFAP | Glial Fibrillary Acidic Protein | CAGTTATCAGGAGGCGCTGG (SEQ ID NO: 18) | TTTGCCCCCTCGAATCTGC (SEQ ID NO: 39) |
| THY1 | Thy-1 Cell Surface Antigen | TGGATTAAGGATGAGGCCCG (SEQ ID NO: 19) | TGGGGAGGTGCAGTCTGTAT (SEQ ID NO: 40) |

TABLE 1-continued

| Gene Symbol | Gene Description | Forward Primer Sequence | Reverse Primer Sequence |
| --- | --- | --- | --- |
| IRBP | Interphotoreceptor Retinoid-Binding Protein | TATCTACAACCGCCCCTCCA (SEQ ID NO: 20) | CTGGTGAGGACCACCACATC (SEQ ID NO: 41) |
| CRX | Cone-Rod Homeobox | CCTTCTGACAGCTCGGTGTT (SEQ ID NO: 21) | TGGTGTACTTCAGCGGTCAC (SEQ ID NO: 42) |

Flow Cytometry

At day 17 of differentiation, cells were completely dissociated using Accutase and stained using the Transcription Factor Buffer Set, which includes a fixation/permeabilization (FP) and wash/permeabilization (WP) buffer (BD Biosciences, Franklin Lakes, N.J.). Dissociated samples were first fixed for 45 minutes at 4° C. in the FP buffer followed by a 20 minute block with WP buffer containing 5% normal donkey serum (NDS, Jackson Laboratories, Bay Harbor, Me.). Primary antibodies against Chx10, Lhx3, and the proper matching species isotype control were added at the concentration shown in Table 2 below into WP buffer containing 2% NDS and incubated at 4° C. for 45 minutes. After 2 washes with wash/perm buffer, secondary antibodies donkey anti-mouse IgG, Alexa Fluor 488 (Life Technologies), at a dilution of 1:200, were added to WP buffer and incubated at 4° C. for 45 minutes. After 2 washes with WP buffer, samples were passed through a 35 µm filter before assessing with a BD Accuri C6 (BD) cytometer (min. 20,000 events ea). Cytometry analysis was performed using FlowJo V10 (Flowjo, Ashland, Oreg.).

TABLE 2

| Marker | Cat. Number | Species | Dilution | Vendor |
| --- | --- | --- | --- | --- |
| Chx10 | sc-374151 | Mouse | 1:1000 | Santa Cruz Biotechnology |
| β-III-Tubulin | MRB-435P | Rabbit | 1:1000 | BioLegend |
| VGlut 2 | 135 403 | Rabbit | 1:500 | Synaptic Systems |
| Neurofilament | 2H3 | Mouse | 1:20 | Developmental hybridoma studies bank |
| Neurofilament 200 | N4142 | Rabbit | 1:200 | Sigma-Aldrich |
| Lhx3 (Lim3) | 67.4E12 | Mouse | 1:500 | Developmental hybridoma studies bank |
| Olig2 | AB9610 | Rabbit | 1:500 | Millipore (EMD) |
| Hb9 | 81.5C10 | Mouse | 1:20 | Developmental hybridoma studies bank |
| Stem 121 | Y40410 | Mouse | 1:500 | Clontech |
| Human Nuclear Antigen | MAB1281 | Mouse | 1:200 | Millipore (EMD) |
| GRP1 | ab25963 | Rabbit | 1:200 | Abcam |
| GABA | A2052 | Rabbit | 1:2000 | Sigma-Aldrich |
| NeuN | abN91 | Chicken | 1:500 | Millipore (EMD) |
| Chx10 | ab16141 | Sheep | 1:500 | Abcam |
| Oct-3/4 | sc-8629 | Goat | 1:100 | Santa Cruz Biotechnology |
| Ms isotype | MAB002 | Mouse | | R&D Systems |
| NeuN | ABN91 | Rabbit | 1:1000 | Millipore (EMD) |
| Synaptophasin | 101 002 | Rabbit | 1:200 | Synaptic Systems |

Immunocytochemistry and Imaging

Samples were fixed using 4% paraformaldehyde (VWR) for 30 minutes and permeabilized using 0.1% Triton™-X (octyl phenol ethoxylate) in phosphate buffer saline (PBS) for 15 minutes at 4° C. before blocking for 1 hour at 4° C. with PBS containing 5% NDS. Primary antibodies (Table 2) were diluted in PBS containing 2% NDS and incubated overnight. Samples were washed three times with PBS for 15 minutes at room temperature before incubating with secondary antibodies (Life Technologies) diluted in PBS containing 2% NDS. Hoechst was added to the samples for 10 min then washed and imaged using a Zeiss Axio Observer and processed using Photoshop.

Single Cell RNAseq

At Day 17 of culture, cells were dissociated with Accutase. Approximately 8,000 cells were prepared for single cell analysis through droplet encapsulation by the Chromium Controller and library preparation with the Chromium Single Cell 3' v1 Library and Gel Bead Kit (10× Genomics, San Francisco, Calif.). cDNA was sheared using a Covaris S2 sonicator and 12 PCR cycles were run during cDNA amplification. Libraries were sequenced on a NextSeq 500 (Illumina, San Diego, Calif.). Sequences were demultiplexed and aligned to human reference genome hg19 using the default settings of 10× Genomics Cellranger v 1.2. Genes were annotated using Ensembl version 70. After Cellranger filtering, >85 million valid reads remained with >70% mapping to the transcriptome. Downstream analysis was performed using Seurat (Macosko E Z, et al. (2015) *Cell* 161(5):1202-1214; Satija R, et al. (2015) *Nat Biotechnol* 33(5):495-502) and cells not expressing between 500 and 5000 unique genes were removed. A subset of high-variance genes was determined using Seurat's "MeanVarPlot" function (expression cutoff of ≥0.25; dispersion cutoff of ≥0.50) and used to group cells into clusters (principal components 1-12; cluster resolution parameter=0.5) (van der Maaten LJP HG (2008) *Journal of Machine Learning Research* 9:2579-2605). The top 20 differentially expressed genes for each cluster were plotted in the heatmap. Raw data is available at SRA under the accession number GSE97564. Gene Ontology analysis was performed on statistically significant differentially expressed genes (p≤0.05) using PANTHER (Ashburner M, et al. (2000) *Nat Genet* 25(1):25-29; Gene Ontology C (2015) *Nucleic Acids Res* 43(Database issue): D1049-1056) and GOrilla (Eden E., et al. (2007) *PLoS Comput Biol* 3(3):e39; Eden E., et al. (2009) *BMC Bioinformatics* 10:48).

Calcium Imaging and Analysis

Cultures were washed with PBS and the medium was replaced with Neurobasal plus Fluo4 AM (10 µM, Life Technologies) for 30 minutes at 37° C. The cultures were then washed with fresh Neurobasal and allowed to recover for an additional 30 minutes at 37° C. before recording on a Zeiss Axio Observer.

To analyze wide field calcium videos, soma were identified from phase images and selected as regions of interest (ROI) in the corresponding fluorescent green channel. Mean fluorescence intensity for each region of interest was measured over time at a sampling rate of 2.38 frames per second using MATLAB (MathWorks, Natick, M) to assess calcium fluctuations within the ROIs. To minimize noise, the average of each trace was calculated and subtracted from the whole. A minimum of 20 ROI's were identified for each field of view.

Electrophysiological Testing

Neurons (day 27, 41, 63) were recorded in the whole-cell configuration using glass pipette electrodes filled with the internal solution ((mM): 100 K-gluconate, 20 KCl, 10 HEPES, 4 Mg-ATP, 0.3 Na-GTP, 10 Na-phosphocreatine, and 0.2% biocytin; osmolality 300 mOsm), while being perfused with warm ACSF ((mM): 126 NaCl, 26 $NaHCO_3$, 3.0 KCl, 1.25 $NaH_2PO_4$, 2.0 $CaCl_2$, 2 $MgCl_2$, and 20 dextrose; osmolality 320 mOsm, T=33 deg C.; bubbled with 95% $O_2$+5% $CO_2$ mixture, pH=7.3-7.35). Resting membrane potential was measured immediately after achieving the whole cell configuration. Action potentials were elicited by injecting a 1.5 s long depolarizing current of 20 pA and measuring the voltage response in current clamp (baseline voltage was held between −60 and −70 mV by injecting a small, constant, negative current). Action potentials were analyzed using custom-written software in Igor Pro®, Wavemetrics.

Spinal Transplantation

All animal studies were performed in accordance with the IACUC at the University of San Francisco, Calif. Day 17 cultures were dissociated for 45 minutes using Accutase, washed with PBS, resuspended in ice-cold DMEM at ~5×10$^5$ cells/µL, and maintained on ice until transplantation. Female C57Bl/6j SCID mice age 12 weeks were anesthetized using isoflurane and a dorsal laminectomy was performed at T9 to expose the spinal cord. The vertebral column was stabilized and the dissociated cells were transplanted over 4 injection sites bilaterally in the ventral horns of the spinal cord at the rostral and caudal edges of the laminectomy site (~1.25×10$^5$ cells/site). The musculature over the exposed spinal cord was sutured closed and the skin was closed with surgical clips. Antibiotics (enrofloxacin) were delivery daily (I.P., 2.5 mg/kg) for 10 days. After two weeks, animals were euthanized and transcardially perfused with PBS followed by 4% paraformaldehyde. A 2 cm segment of spinal cord tissue centered over the transplantation site was harvested and post-fixed overnight.

Tissue Processing and Immunofluorescence

Spinal cords were embedded and 20 µm sections were obtained in the sagittal plane. Sections were permeabilized with 0.3% Triton-X in PBS for 15 minutes or ice-cold acetone for 10 minutes. All sections were then blocked with 10% NDS, 5% bovine serum albumin, and 0.1% triton-x in PBS. Sections were incubated with primary antibodies found in Table 2. Sections were washed 3 times and incubated with the appropriate secondary antibodies (1:500) in blocking solution for 1 hour, then counterstained and mounted with coverslips using Prolong Gold Antifade containing DAPI. Z-stack images (1 µm step size) were acquired using a Zeiss Axio Observer inverted wide-field microscope and an Apotome structured light attachment. Maximum intensity projection was performed on Z-stack images to create a single two-dimensional image spanning the entire thickness of the section.

Statistical Analysis

Statistical analysis was performed using Prism 6 software. The mean and ±standard deviation was calculated for all data from 3 biological replicates unless otherwise noted. Unpaired t-tests were performed when comparing 2 groups. One-way analysis of variance (ANOVA), and where appropriate, Tukey's multicomparison tests were used when 3 or more groups were specified. In all comparisons, significance was defined as $p<0.05$.

Freeze and Thaw

On day 17 of the V2a interneuron differentiation, cells were dissociated enzymatically with Accutase for 45 minutes with trituration every 15 minutes. Cells were then washed with PBS, centrifuged, and re-suspended in 10% DMSO, 40% FBS, and 50% neural induction media supplemented with BDNF, RA, AA, Pur, DAPT, and 10 µM Rock inhibitor (Y27632). Samples were put into cryovials and stored in a Mr. Frosty™ in the −80° C. freezer for at least 24 hours. Samples were then taken out of the Mr. Frosty™ and stored in the −80° C. freezer or liquid nitrogen for long-term storage. To thaw, samples were placed in a water bath, recovered in neural induction media containing 10 µM Rock inhibitor, and centrifuged. Cells were re-suspended in neural induction media containing BDNF, RA, AA, Pur, DAPT, and 10 µM Rock inhibitor, and plated onto a 24-well plate. Cultures were recovered in the incubator for 3 days prior to analysis.

Re-Plating

Day 17 V2a cultures were dissociated as stated above. One well of a 24-well was then re-plated back onto 1 well of a Matrigel-coated 24-well in media containing BDNF, RA, AA, Pur, DAPT, and 1 µM Rock inhibitor. Cultures were recovered in the incubator for 3 days before analysis.

Wnt Activation to Specify the Rostral/Caudal Identity

For the "D0 CHIR treated" group, the GSK3 inhibitor, 2 µM CHIR990201 was added into the V2a interneuron protocol from day 0 to day 7. For the "D-2 CHIR treated" group, pluripotent stem cells were initially seeded at a higher density (120 k cells/cm$^2$) in the presence of 2 µM CHIR990201 for two days. The cells were then dissociated and re-plated at 25 k/cm$^2$ to begin the V2a interneuron protocol. CHIR990201 was kept in the media composition from day 0 to day 7. Further culture and analysis proceeded as previously described.

Example 1

Figure 1C:
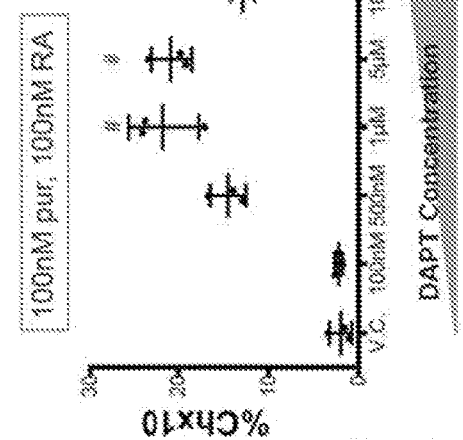
Figure 1D:
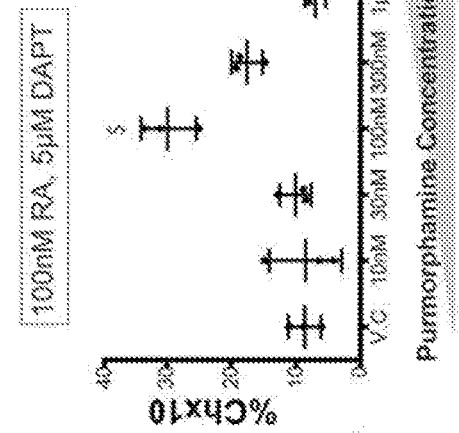
Figure 1E:
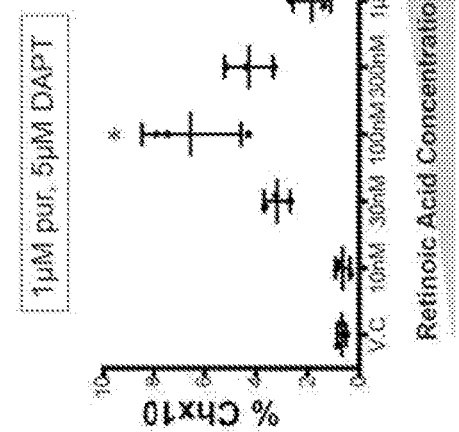
Figure 1F:
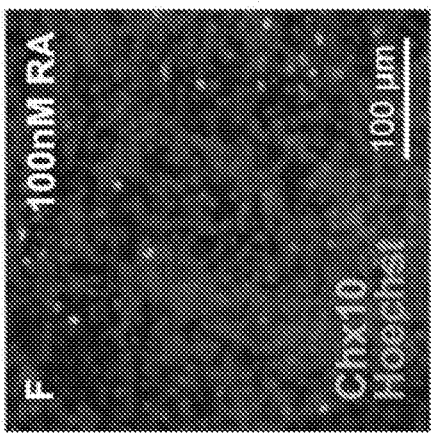
Figure 1G:
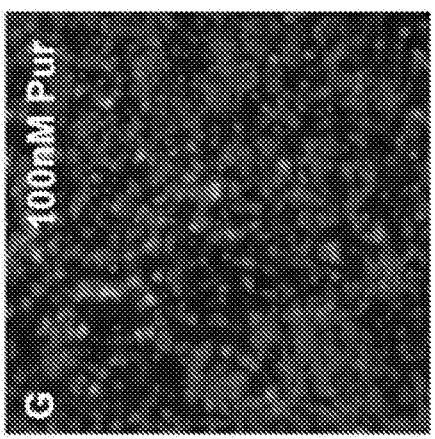

Human PSC-Derived V2a Interneuron Differentiation is Dependent on Retinoic Acid, Sonic Hedgehog and Inhibition of Notch Signaling To differentiate V2a interneurons from human PSCs (hPSCs), the concentrations of morphogens and signaling pathways implicated in V2a commitment (RA, Shh, and Notch inhibitor, DAPT) were sequentially varied and the percentages of CHX10+ differentiated from hPSCs at day 17 were examined. RA concentration of 100 nM starting at day 5 with fixed concentrations of the Shh agonist, purmorphamine, (pur, 1 µM) and DAPT (5 µM) (both beginning on day 7) resulted in a CHX10+ population at day 17 (~6%, FIG. 1C). Similarly, 100 nM of pur treatment beginning at day 7 with 100 nM RA and 5 µM DAPT concentrations resulted in ~30% Chx10+ cells after 17 days of differentiation (FIG. 1D). Furthermore, DAPT concentration was varied beginning on day 7 with fixed RA and pur concentrations (100 nM each) and 1 µm and 5 µM DAPT resulted in comparable CHX10+ populations (~15%; FIG. 1E). Regardless of the specific concentrations of the morphogenic cues, CHX10+ cells appeared to be relatively evenly distributed throughout the differentiating cultures (FIG. 1F-H).

Figure 1H:
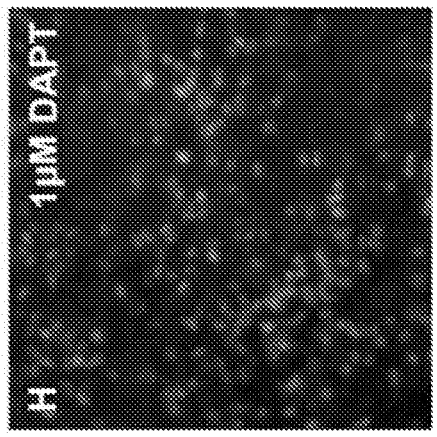

FIGS. 1A-1H: Morphogen concentrations modulate V2a interneuron population. (FIG. 1A) Schematic of the developing neural tube. Retinoic Acid (RA), released from the somites, and sonic hedgehog (Shh), released from the floorplate and notochord, pattern the different progenitor domains of the neural tube. (FIG. 1B) Timeline of V2a interneuron protocol. (FIG. 1C) Flow cytometry analysis of CHX10 expression as RA concentration was varied and Shh agonist, purmorphamine (pur), and DAPT were held constant. *=p<0.05 compared to V.C, 10 nM, 30 nM, and 1 µM groups. (FIG. 1D) Flow cytometry analysis of Chx10 expression as pur concentration was varied and RA and DAPT were held constant. $=p<0.05 compared to all groups. (FIG. 1E) Flow cytometry of CHX10 expression as DAPT concentration was varied and RA and pur were held constant. #=p<0.05 compared to V.C, 100 nM, and 500 nM. (FIGS. 1F-1H) Immunostaining for CHX10 and nuclei labeling of differentiations with 100 nM RA (FIG. 1F), 100 nM pur (FIG. 1G), or 1 µM DAPT (FIG. 1H). Scale bar=100 µm, n=2-3.

Since DAPT concentrations of 1 µM and 5 µM yielded similar efficiencies of V2a interneuron differentiation, the effects of both concentrations on the yield of CHX10+ cells were examined before proceeding further. Higher concentrations of small molecule inhibitors, such as DAPT, can often be more cytotoxic, therefore, the total number of cells and yield of Chx10+ cells per input pluripotent cells were examined. The lower DAPT concentration (1 µM) yielded a greater number of viable cells than cultures treated with 5 µM DAPT (4.40 million cells vs. 2.85 million cells, FIG. 2B). Moreover, the number of CHX10+ cells per input pluripotent cell increased ~50% using 1 µM DAPT (FIG. 2C). Varying the onset of Notch inhibition by starting DAPT treatment on day 5, 7, or 10 of differentiation (FIG. 2E) yielded similar percentages of CHX10+ cells, thus DAPT was added at day 7 for all future studies to coincide with Shh agonism. In addition, a seeding density of 25,000 cells per cm$^2$ resulted in a greater percentage of CHX10+ cells as compared to 5,000 and 100,000 cells per cm$^2$ (FIG. 2E). In addition, LHX3, a marker of progenitor and committed V2a interneurons, was expressed by nearly half of all cells at day 17 of V2a interneuron differentiation (46.3%). Overall, these results demonstrate the ability of hPSCs to robustly differentiate into putative V2a interneurons using RA and Shh agonism in combination with Notch inhibition.

FIGS. 2A-2E: DAPT concentration affects V2a interneuron yield. (FIG. 2A) Flow cytometry analysis of CHX10 expression at Day 17 with 1 µM and 5 µM of DAPT. (FIG. 2B) Total number of cells per 24-well culture at day 17 of V2a interneuron differentiation with 1 µM and 5 µM DAPT (using 100 nM RA and 100 nM pur). *=p<0.05 by unpaired t-test. (FIG. 2C) Total number of CHX10+ cells at day 17 per input pluripotent stem cell. (FIG. 2D) Flow cytometry analysis of CHX10 at day 17 when DAPT was added on day 5, day 7, day 10, day 13, or vehicle control (V.C., DMSO). #=p<0.05 compared to V.C. $=p<0.05 compared to V.C. and Day 13. (FIG. 2E) Flow cytometry analysis of CHX10 at day 17 using three different initial seeding densities. &=p<0.05 compared to 5 k and 100 k. ^=p<0.05 compared to 5 k. All data are reported as mean±standard deviation and statistical comparisons were made using a one-way ANOVA and Tukey's multicomparison test.

Example 2

Specificity of V2a Differentiation

Figure 3A:
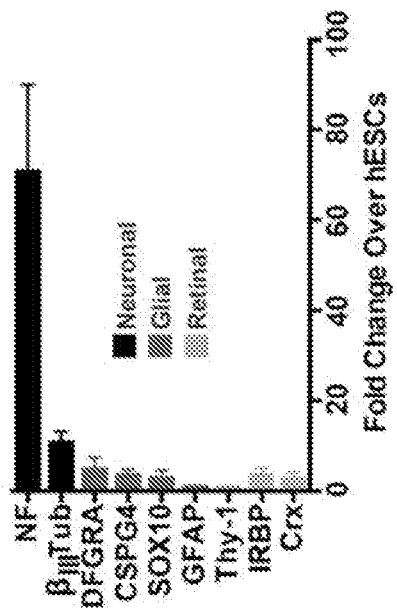
FIGS. 3A-3D are a collection of graphs showing in vitro neurogenesis and V2a interneuron differentiation from hPSCs by modulating morphogen signaling pathways, according to embodiments of the present disclosure. For FIG. 3D, each x-axis grouping includes from left to right, H7 ESCs, H1 ESCs, WTC iPSCs, and WTB iPSCs.
Figure 3B:
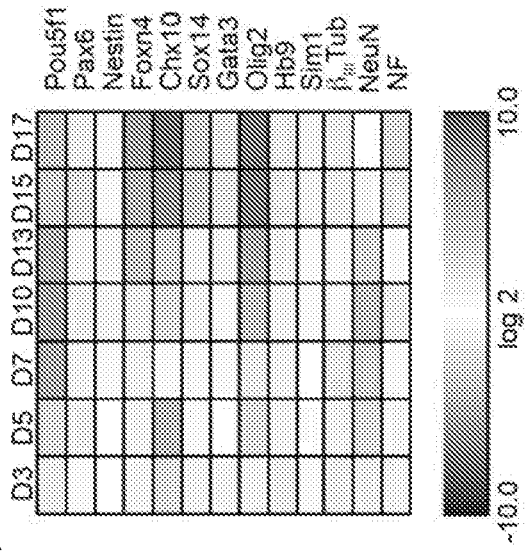
Figure 3D:
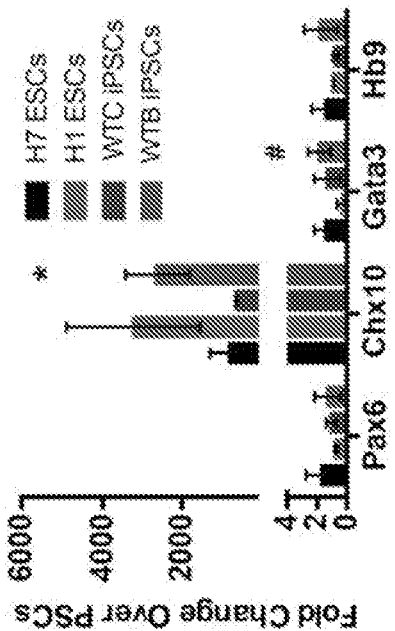
Figure 3C:
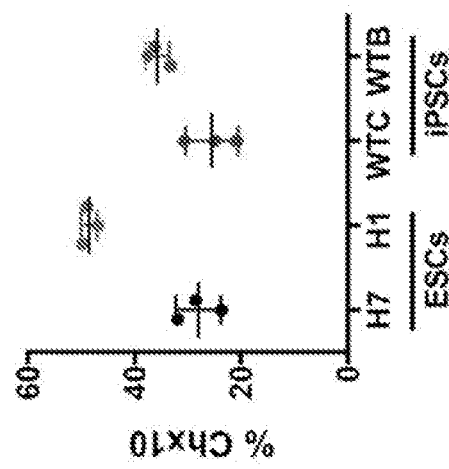
Figure 4A:
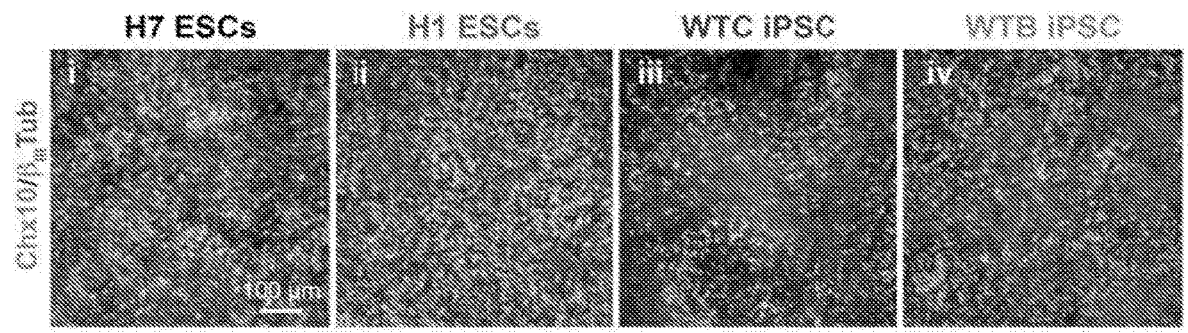
FIGS. 4A and 4B are a collection of graphs and images showing differentiation of different hPSCs into a V2a interneuron population by modulating morphogen signaling pathways, according to embodiments of the present disclosure.
Figure 4B:
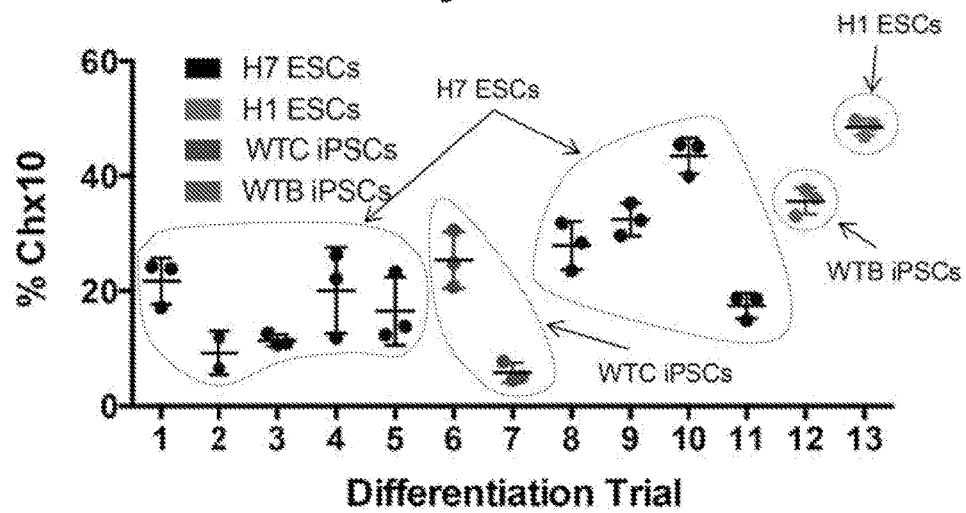

Gene expression analysis throughout the first 17 days of differentiation was performed to characterize the temporal changes of the V2a interneuron cell population (FIG. 3A). The expression of the pluripotency gene POU5F1 expression decreased by day 3 and remained down-regulated through day 17. Early neural markers expressed during neural tube development increased by day 7 (PAX6 and NES (Nestin)). Other markers of spinal cell types expressed in the ventral neural tube (GATA3, OLIG2, HB9, and SIM1) began as early as day 3 and continued to increase expression throughout the differentiation. Expression of markers for the p2 domain (FOXN4) and committed V2a interneurons (CHX10 and SOX14) began on day 10 and were highly upregulated by day 15. It appeared that neuronal genes (NEFL (NF), TUBB3 ($\beta_{III}$ tubulin)) were more highly expressed (~70 fold and ~10 fold respectively) than any glial (PDGFRA, CSPG4, SOX10, and GFAP) or retinal cell types (THY1, IRBP, and CRX) at day 17 (FIG. 3B). The resulting protocol for V2a interneuron differentiation (100 nM RA, 100 nM pur, and 1 µM DAPT) was tested on multiple hPSC lines (H7 ESCs, H1 ESCs, WTC iPSCs, and WTB iPSCs) to determine reproducibility. Chx10+ populations were robustly obtained in all of the lines examined, with efficiencies ranging from 25.4%-48.6% (FIG. 3C). Gene expression of spinal neuronal markers was examined at day 17 for each of the four hPSC cell lines and high CHX10 expression was consistently detected, whereas expression levels of other neuronal markers (PAX6, HB9, and GATA3) were similarly low between the different cell lines (FIG. 3D). No discernible spatial patterns were observed for CHX10+ cells in the differentiating cultures (FIG. 4A). The V2a interneuron protocol was reproduced more than a dozen independent times under the same conditions (100 nM RA, 100 nM pur, and 1 µM DAPT) across the 4 different cell lines and CHX10+ percentages above 20% were routinely achieved (FIG. 4B). These data demonstrate the establishment of a robust neuronal differentiation process that is capable of reproducibly yielding enriched cultures of V2a interneurons.

FIGS. 3A-3D: V2a interneuron protocol robustly increases hPSC neurogenesis. (FIG. 3A) Gene expression analysis throughout V2a interneuron differentiation compared to undifferentiated H7 hESCs. (FIG. 3B) Neuronal, glial, and retinal gene expression at day 17 compared to H7 hESCs. (FIG. 3C) CHX10 percentage of human ESCs (H7, H1) and iPSCs (WTB and WTC) differentiated with the V2a interneuron protocol. (FIG. 3D) Gene expression at day 17 compared to PSCs. For CHX10 expression, *=p<0.05 compared to H7 and WTC. For GATA3 expression, #=p<0.05 compared to H1. For all groups, n=3.

FIGS. 4A-4B: V2a interneuron differentiation is effective in multiple human PSC lines. (FIG. 4A, panels i-iv) Immuno staining for CHX10, $\beta_{III}$ Tubulin, and labeled nuclei of H7 ESCs (FIG. 6A, panel i), H1 ESCs (FIG. 4A, panel WTB iPSCs (FIG. 4A, panel iii), and WTC iPSCs (FIG. 4A, panel iv) differentiated using the V2a interneuron protocol. Scale bar is 100 µm. (FIG. 4B) Percentage of CHX10+ cells from multiple independent V2a interneuron differentiations in various PSC lines.

Figure 5A:
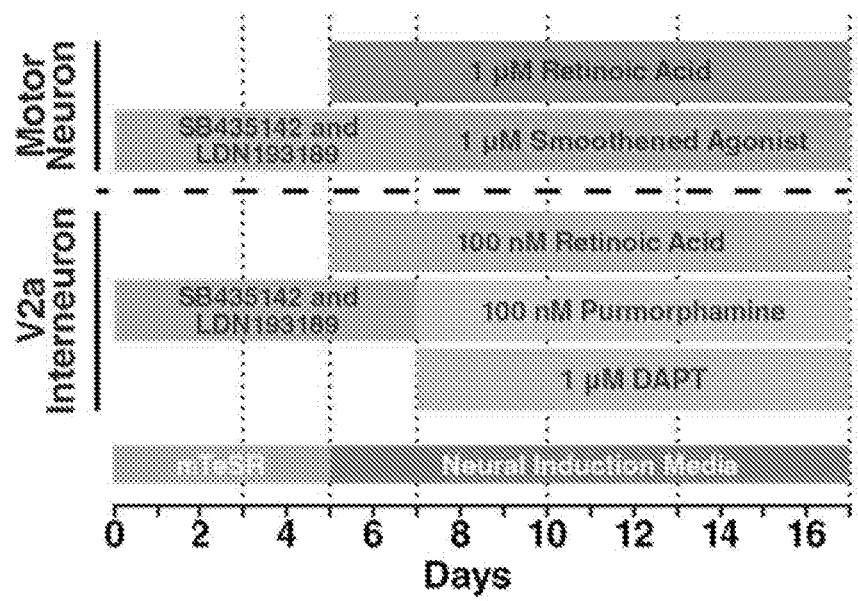
FIGS. 5A-5D are a collection of schematic diagrams, graphs and images showing specific differentiation of hPSCs into V2a interneurons over motor neurons in vitro by modulating morphogen signaling pathways, according to embodiments of the present disclosure.
Figure 5B:
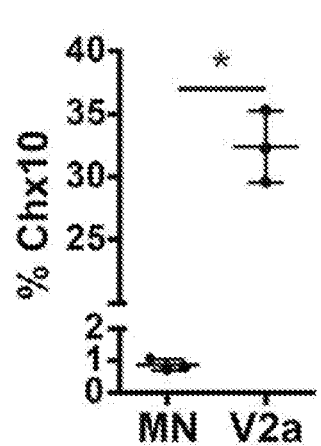
Figure 5C:
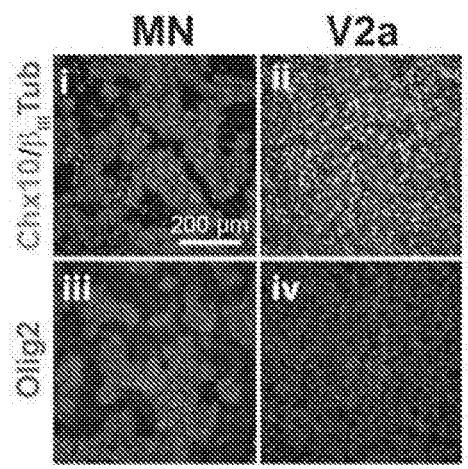
Figure 5D:
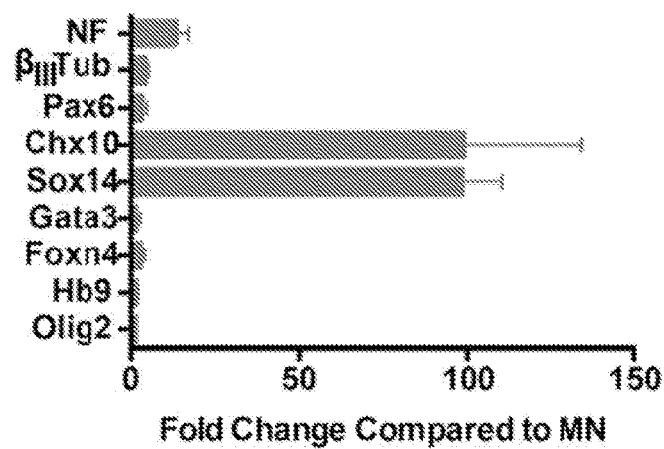

To examine the specificity of the V2a interneuron protocol, a direct comparison with a similar human motor neuron protocol was performed (FIG. 5A). The V2a interneuron differentiation yielded ~30% CHX10+ cells, whereas the motor neuron differentiation yielded very few CHX10+ cells (<1%, FIG. 5B). A greater number of CHX10+ nuclei and more abundant $\beta_{III}$ tubulin expression were observed using the V2a interneuron conditions compared to the motor neuron conditions (FIG. 5C, panels i-ii). In addition, many OLIG2+ (progenitor motor neuron marker) nuclei were yielded by the differentiation of motor neurons compared to very few observed in V2a interneuron differentiation cultures (FIG. 5C, panels iii-iv). Interestingly, expression of neuronal genes (NEFL (NF), TUBB3 ($\beta_{III}$ tubulin), and PAX6) was increased with the V2a interneuron differentiation compared to the motor neuron, but V2a interneurons transcription factors (CHX10 and SOX14) exhibited the highest expression (~100-fold) compared to the motor neuron differentiation, while motor neuron markers (OLIG2 and HB9) remained comparable between the two differentiation processes (FIG. 5D). Collectively, these results demonstrate that the V2a differentiation conditions specifically enrich for the interneuron population (CHX10+) relative to a similar human motor neuron protocol.

FIGS. 5A-5D: V2a interneuron protocol specifically increases V2a interneuron population compared to standard motor neuron differentiation. (FIG. 5A) Timeline contrasting the motor neuron (top) and V2a interneuron (bottom) differentiation protocols. (FIG. 5B) Flow cytometry analysis of CHX10 for motor neuron and V2a interneuron differentiation. *=p<0.005 by unpaired t-test, n=3. (FIG. 5C) Immunostaining for CHX10 and nuclei (FIG. 5C, panels i-ii) Immunostaining for β$_{III}$ Tubulin (red) in cultures differentiated with the motor neuron protocol (FIG. 5C, panel i) and V2a interneuron protocol (FIG. 5C, panel ii). (FIG. 5C, panels iii-iv) Immunostaining for OLIG2 in cultures differentiated with the motor neuron protocol (FIG. 5C, panel iii) and V2a interneuron protocol (FIG. 5C, panel iv). Scale bars=100 μm. (FIG. 5D) Gene expression of day 17 V2a interneuron cultures compared to day 17 motor neuron cultures, n=3.

Example 3

Single-Cell RNAseq Analysis

Figure 10D:
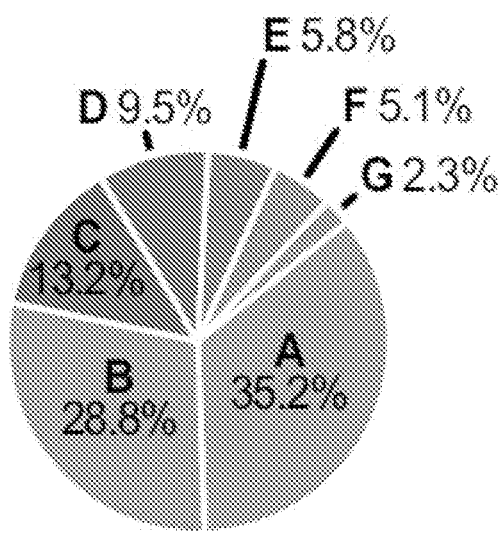
Figure 10E:
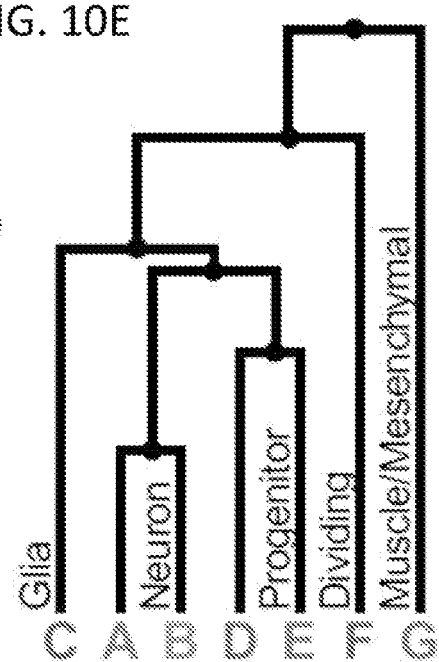
Figure 10F:
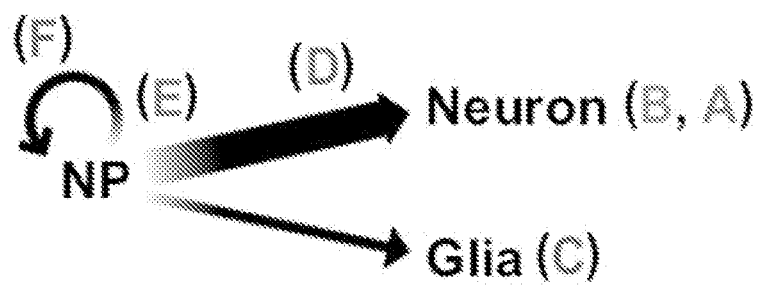
Figure 11:
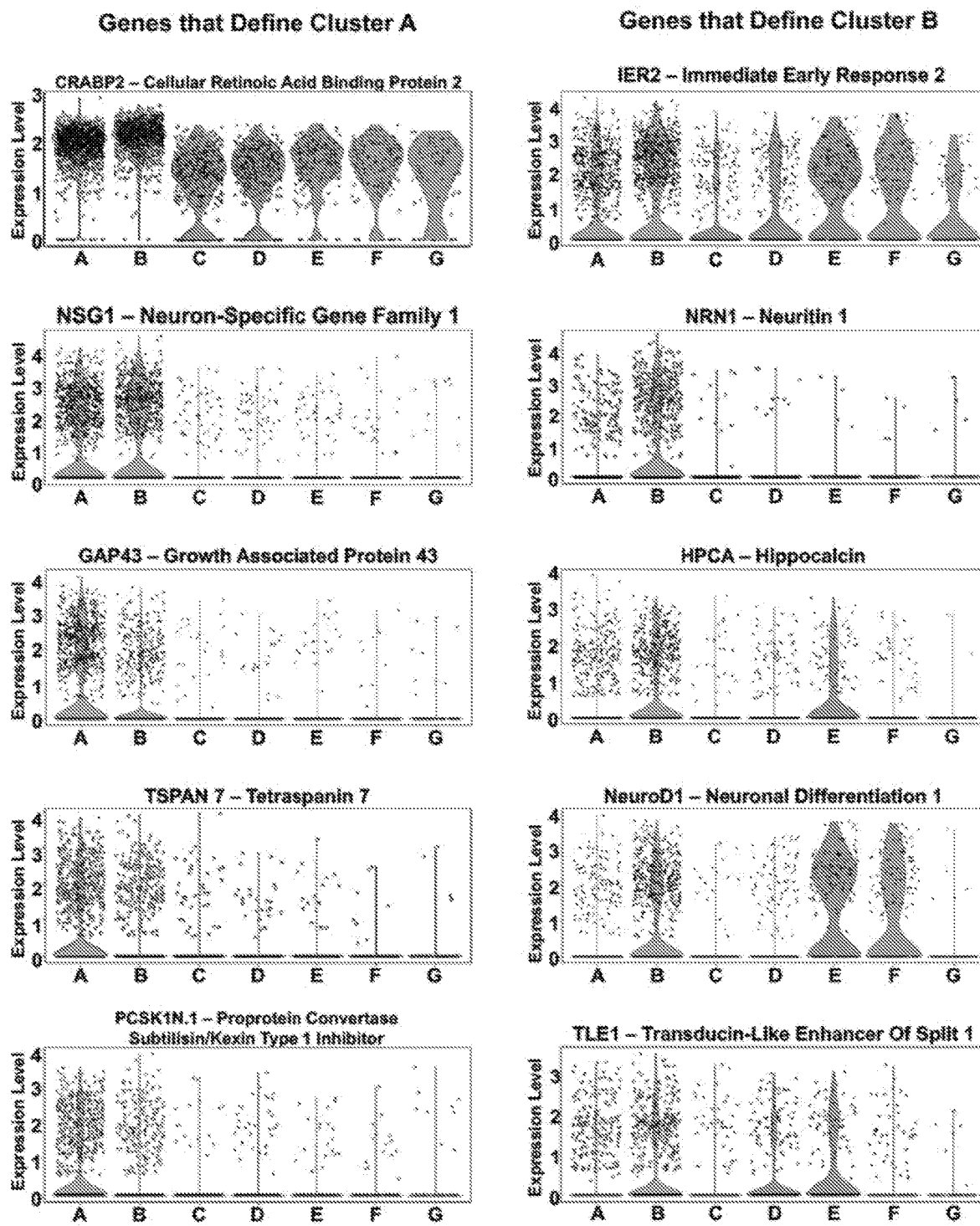
FIG. 11 provides select violin plots of genes that identify cluster A and cluster B. Representative genes for cluster A and B were chosen from the top 50 differentially expressed genes from the A:B pair-wise comparison.
Figure 12:
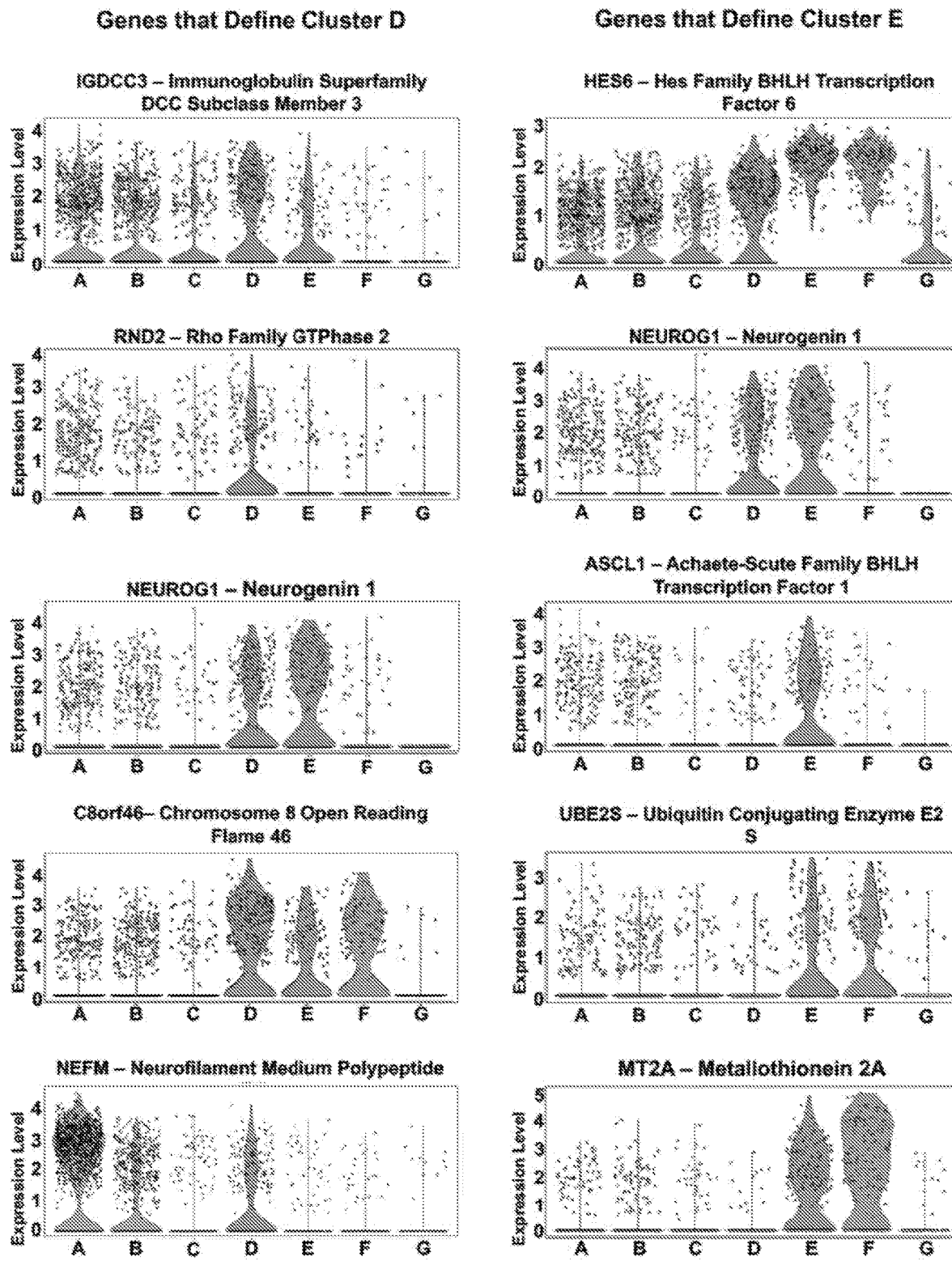
FIG. 12 provides select violin plots of genes that identify cluster D and cluster E. Representative genes for cluster D and E were chosen from the top 50 differentially expressed genes from the DB and E:B pair-wise comparison, respectively.
Figure 13:
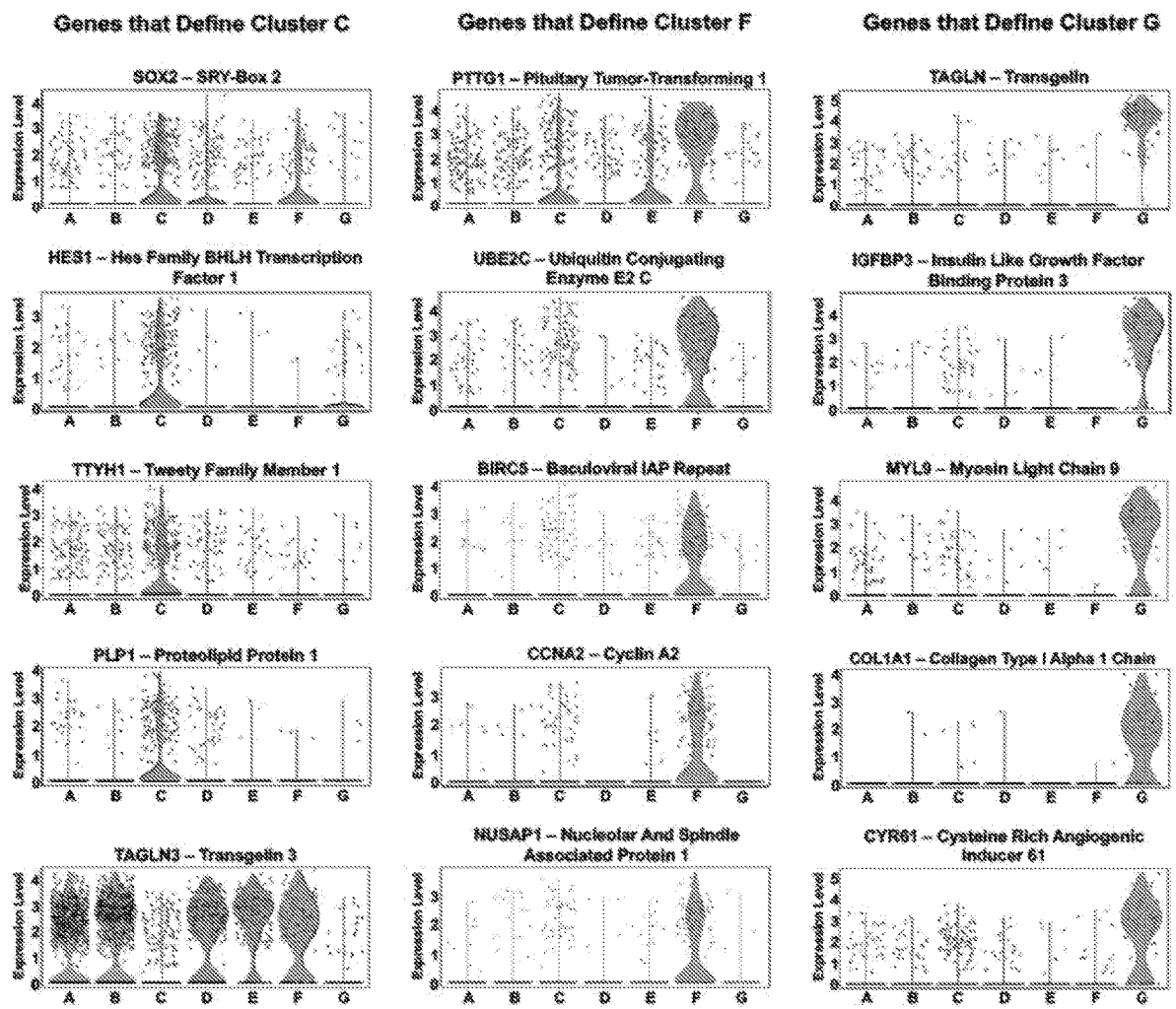
FIG. 13 provides select violin plots of genes that identify cluster C, cluster F and cluster G. Representative genes for cluster C, F, and G were chosen from the top 50 differentially expressed genes from the C:B, F:B, and G:B pair-wise comparison, respectively.
Figure 14:
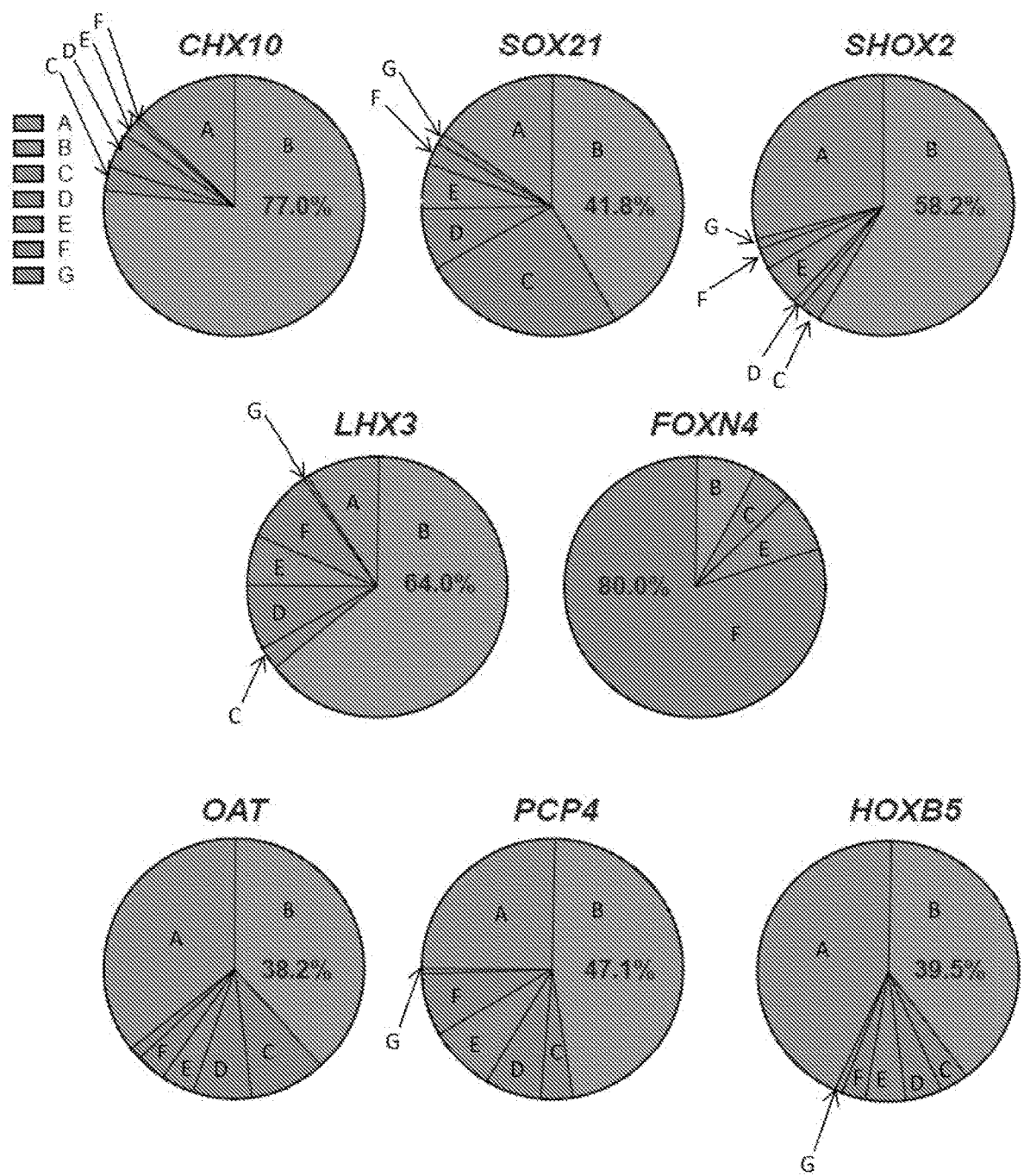
FIG. 14 provides charts showing additional V2a interneuron genes and their cluster identity. Each pie chart reports the number of cells with at least one read for the gene and its cluster identity. The percentage of cells found within cluster B is labeled on the chart for all genes except FOXN4, which labels the percentage of cells found in cluster F.

Single-cell RNAseq analysis was performed to define the cellular composition of the heterogeneous cultures obtained from the above experiments. Seven distinct clusters of cells (designated A-G) were identified by k-means clustering using 12 principal components (FIG. 10A) with 77% of CHX10+ cells contained within cluster B (FIG. 10B). The top globally differentially expressed genes were used to distinguish the general phenotypes of the seven clusters that defined the total population (FIG. 10C and Table 3 (below)). Gene ontology (GO) analysis and individual inspection of the top differentially expressed genes (FIGS. 11-13) suggested that clusters A and B were committed neurons [neuralfilament medium polypeptide (NEFM) and NSG1], cluster C was glial cells (PLP1 and TTHY1), clusters D and E were neuron progenitors (NEUROD1), cluster F contained mitotically active neuronal cells (FOXN4, PTTG1, and UBE2C), and cluster G consisted of mesenchymal/muscle cells (TAGLN and COL1A1) (FIGS. 11-13). Overall, the single-cell RNAseq data indicated that the vast majority of the culture was neuronal (~85%) at different stages of commitment (64% fully committed neurons, 15% neuronal progenitors, and 5% mitotic neuronal progenitors). Nonneuronal cells constituted the remaining fraction of differentiated cells (13% glial and 2% mesenchymal/muscle; FIG. 10D). Clusters A and B were the most closely related to one another (FIG. 10E), sharing many highly expressed genes (GAP43 and NEFM) and GO terms (growth cone and axon). Cluster B, containing the majority of the CHX10+ cells, included cells expressing a number of genes consistent with an excitatory V2a interneuron phenotype, such as SOX21, SHOX2, LHX3, and ornithine aminotransferase (OAT), as well as HOX genes consistent with a hindbrain/cervical identity [homeobox B5 (HOXB5)] (FIG. 14). Both clusters D and E were identified as early neurons (NEUROG1); however, cells in cluster D exhibited a more committed neuron phenotype (RND2 and IGDCC3) compared with cells in cluster E (UBE2S and MT2A) (FIG. 12). Furthermore, 80% of cells expressing the p2 marker FOXN4 were contained within the mitotically active cluster F (FIG. 14). Taken together, these data suggest that the V2a differentiation cultures (at day 17) yield primarily postmitotic excitatory neurons (clusters A and B) that arise from a pool of neuronal progenitors (clusters D and E) and mitotic cells (cluster F) (FIG. 10F) and contain an enriched population of cells expressing markers consistent with a V2a interneuron phenotype.

TABLE 3

|    | Cluster A   | Cluster B | Cluster C | Cluster D | Cluster E | Cluster F | Cluster G |
|----|-------------|-----------|-----------|-----------|-----------|-----------|-----------|
| 1  | NEFL        | CRABP2    | VIM       | C8orf46   | HES6      | UBE2C     | TAGLN     |
| 2  | NEFM        | NRN1      | FGFBP3    | RGS16     | MT1X      | HMGB2     | IGFBP3    |
| 3  | STMN4       | SNCG      | ZFP36L1   | GADD45G   | CKB       | MT2A      | ACTA2     |
| 4  | TUBB2B      | STMN2     | HES1      | ARL4D     | VSX1      | HES6      | ANXA1     |
| 5  | PMEL        | GNA5      | MGST1     | NEUROG1   | MT2A      | PTTG1     | CTGF      |
| 6  | GAP43       | HOXB5     | PLP1      | HES6      | GLRX      | MT1X      | NPPB      |
| 7  | RTN1        | PRR24     | DLK1      | TFDP2     | NEUROG1   | BIRC5     | MYL9      |
| 8  | MLLT11      | CRABP1    | TTYH1     | GADD45A   | CDHI3     | CCNA2     | S100A11   |
| 9  | TCEAL7      | NEUROD1   | SOX2      | DLL3      | PPP1R17   | CCNB2     | TPM1      |
| 10 | GNG3        | NSG1      | ID3       | PSTPIP1   | ASCL1     | NEK2      | IGFBP5    |
| 11 | RP11-834C11.4 | PCP4    | GPC3      | MFNG      | NEUROD1   | CDC20     | CALD1     |
| 12 | AP1S2       | HOTAIRM1  | GSN       | PHLDA1    | DOK5      | NUSAP1    | CYR61     |
| 13 | CLDN5       | ISG15     | GNG5      | PRDX1     | RASD1     | TUBB4B    | HSPB1     |
| 14 | TSPAN7      | COTL1     | ARL4A     | BTG1      | FAM162A   | PBK       | SPARC     |
| 15 | UCHL1       | GLRX      | NPC2      | ELAVL4    | B2M       | CDKN3     | ANXA2     |
| 16 | CPE         | DUSP1     | MAD2L1    | VIM       | STC1      | CCNB1     | TNFRSF12A |
| 17 | SCG5        | GNG3      | HMGB2     | RASD1     | DLL3      | CDK1      | MYL12A    |
| 18 | TM2D3       | DANCR     | SMS       | ARL4A     | PPP1R144  | CCNA1     | LGALS1    |
| 19 | HERPUD1     | FOS       | MEST      | SH3BGRL3  | GADD45G   | VSX1      | B2M       |
| 20 | KLHL35      |           | PTTG1     | SOX2      | BID       | GPC3      | C8orf4    |

Example 4

Long-Term Culture Increases the Maturation Profile of V2a Interneurons (A)

Figure 6A:
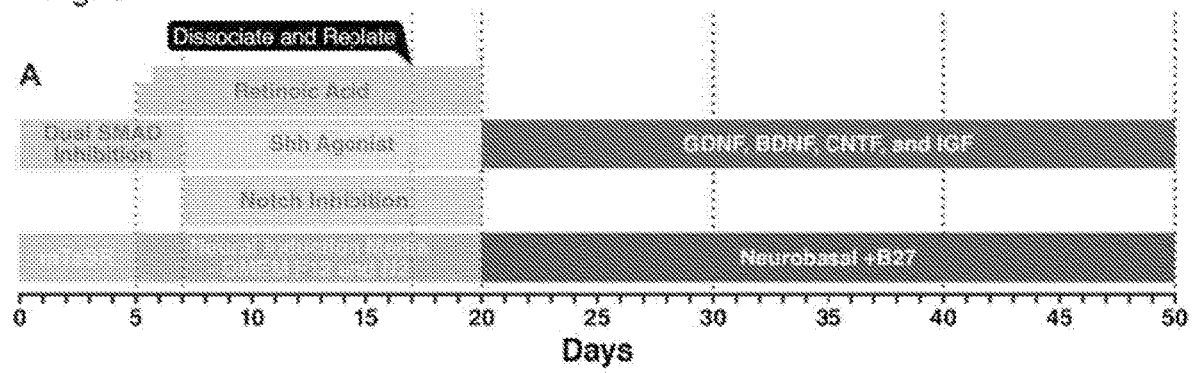

In order to examine the maturation of V2a interneurons, differentiated cultures were dissociated after 17 days, re-plated at subconfluence, and analyzed at days 20, 30, 40, and 50 of culture according to Neuronal Maturation (Protocol 1) (FIG. 6A). Although CHX10$^+$ cells expressed $\beta_{III}$ tubulin at day 20, $\beta_{III}$ tubulin expression was no longer observed by day 50 (FIG. 6E). Expression of neurofilament (NF), a marker of mature neurons, was observed in short neurite processes as early as day 20, however longer neurite extensions were observed beginning at day 30 and by day 50, large and elongated neural bundles were found throughout the cultures (FIGS. 6F-6I). Vesicular glutamate transporter 2 (VGlut2), a marker of glutamatergic neurons, was not detected early (Day 20, FIG. 6J), but its expression was observed in some cells in later stage cultures (FIGS. 6K-6M). VGlut2 was expressed by some of the CHX10 population at day 40 of culture, indicating that the differentiated putative V2a interneurons were adopting a glutamatergic fate and more mature phenotype (FIG. 6L). Altogether, the temporal phenotypic expression patterns support the progressive maturation in vitro, albeit limited, of the V2a interneuron cultures.

FIGS. 6A-6M: V2a interneurons exhibit limited maturation in vitro. (FIG. 6A) Timeline of V2a interneuron maturation cultures. (FIGS. 6B-6M) Immunostaining for CHX10 and nuclei labeling of V2a interneurons on day 20, 30, 40, and 50 of culture. (FIGS. 6B-6E) Immuno staining for $\beta_{III}$ Tubulin. (FIGS. 6F-6I) Immunostaining for neurofilament (NF). White arrowhead indicating neural bundles in I. (FIGS. 6J-6M) Immunostaining of vesicular glutamate transporter 2 (VGLUT2). Scale bar=50 µm.

Calcium imaging was performed to detect spontaneous neural electrical activity during extended culture as a functional indication of neuronal maturation. At different time points, the individual soma of cells loaded with Fluo4 were visually identified (white arrows, FIGS. 7A-7B) and the average change in pixel fluorescence intensity over time was measured. Although calcium fluctuations were not observed initially at day 20, they were observed more often in older cultures (day 40), with increasing amplitudes and frequency. (FIG. 7C). Whole cell patch clamp recordings of individual cells were performed to assess electrophysiological properties of the differentiating cells over time. The resting membrane potential did not significantly change throughout culture duration and remained at about −40 mV (FIG. 7D). However, the action potential frequency of V2a cultures increased over time in culture in response to constant current injection (20 pA; FIG. 7E). Consistent with the phenotypic expression patterns, the electrophysiological properties of the differentiated cells suggest some maturation of V2a interneuron cultures over time.

FIGS. 7A-7E: Electrophysiological properties show increased maturity with culture duration. (FIG. 7A, panels i-iv) Representative phase images of cultures on days 20, 30, 40, and 50. (B$_{i-iv}$) Representative fluorescent images of calcium. Red arrowheads indicate somas where the regions of interest were selected for calcium imaging. (FIG. 7C, panels i-iv) Representative traces of pixel intensity with time. (FIG. 7D) Resting membrane potential of current-clamp patched neurons at Day 27, 41, and 63. (FIG. 7E, panels i-ii) Representative action potential traces in response to 20 pA current injection at Day 27, 41, and 63 (FIG. 7E, panel i). Action potential frequency of current-clamp patched neurons at Day 27, 41, and 63. *=p<0.05 compared to Day 27 and 41 (FIG. 7E, panel ii). Comparisons were made using a one-way ANOVA and Tukey's multicomparison test. For Day 27, 41, and 63, n=5, 6, and 9 respectively.

Example 5

Long-Term Culture Increases the Maturation Profile of V2a Interneurons (B)

Figure 15:
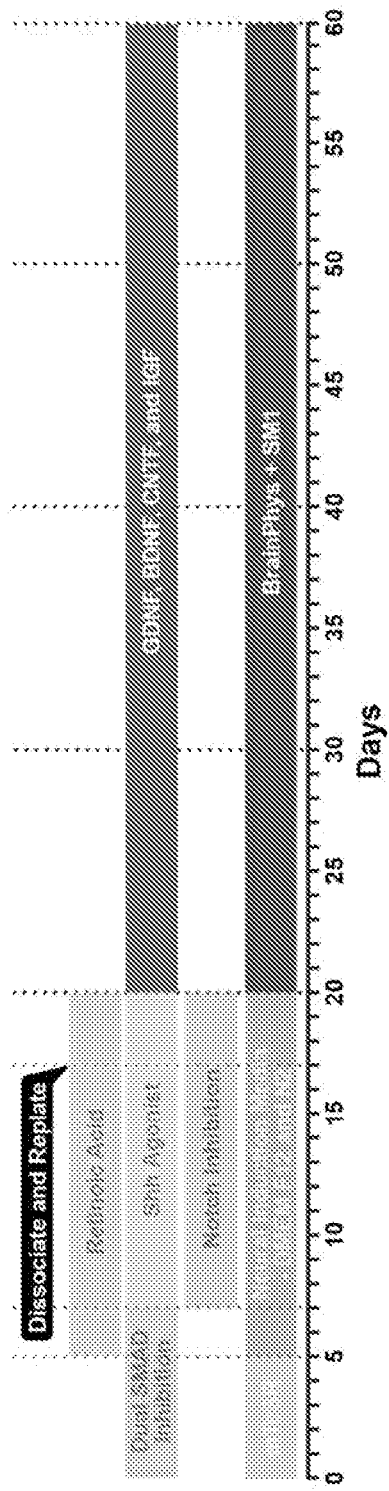
FIG. 15 provides a timeline of V2a interneuron maturation cultures.
Figure 16:
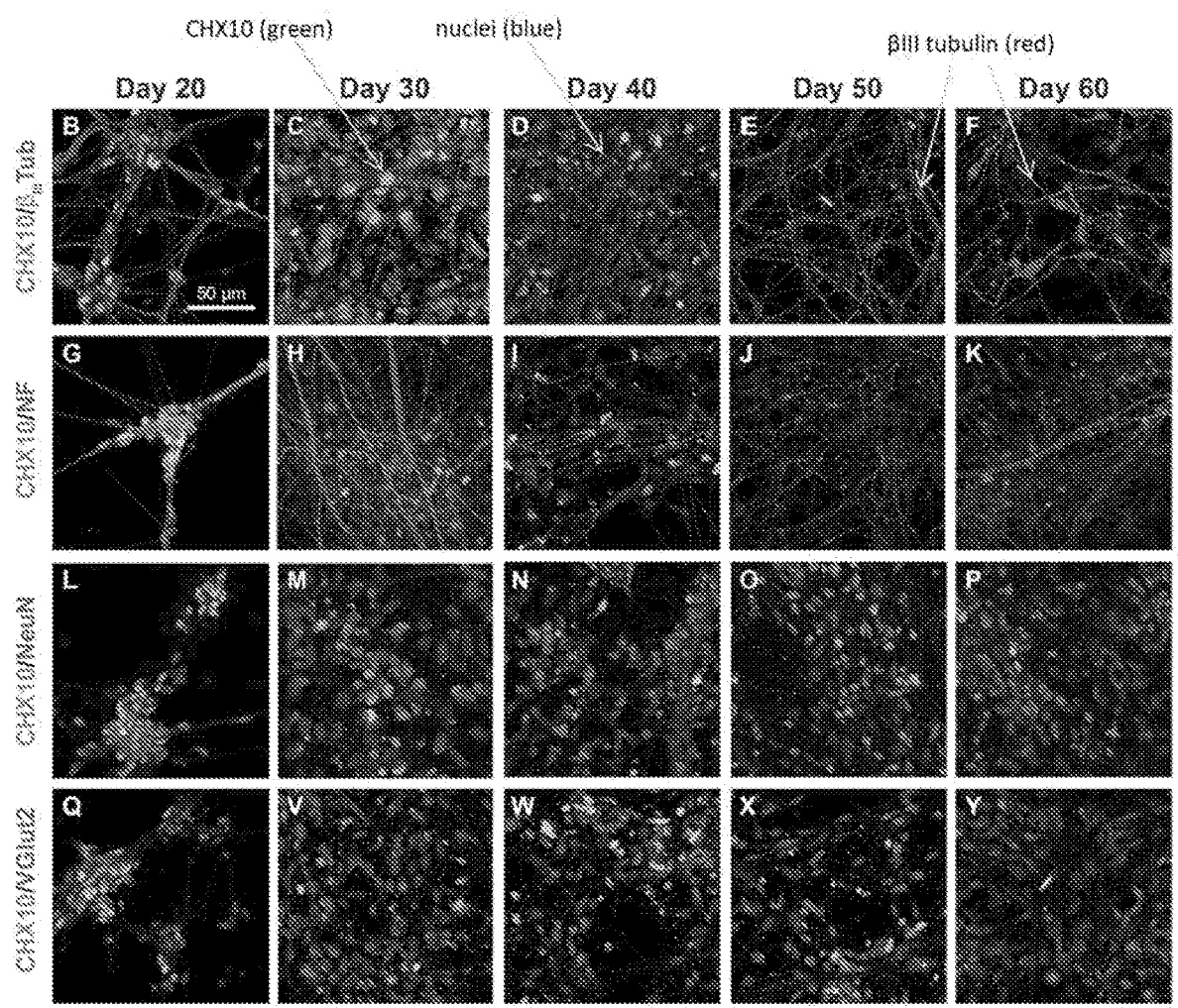
FIG. 16 provides immunostaining images for CHX10 (green) and nuclei labeling (blue) of V2a interneurons on day 20, 30, 40, 50 and 60 of culture. (Panels B-F) Immunostaining for βIII tubulin (red). (Panels G-K) Immunostaining for neurofilament (NF, red). (Panels L-P) Immunostaining for NeuN (red). (Panels Q-Y) Immunostaining of vesicular glutamate transporter 2 (VGLUT2, red). Scale bar=50 μm.
Figure 17:
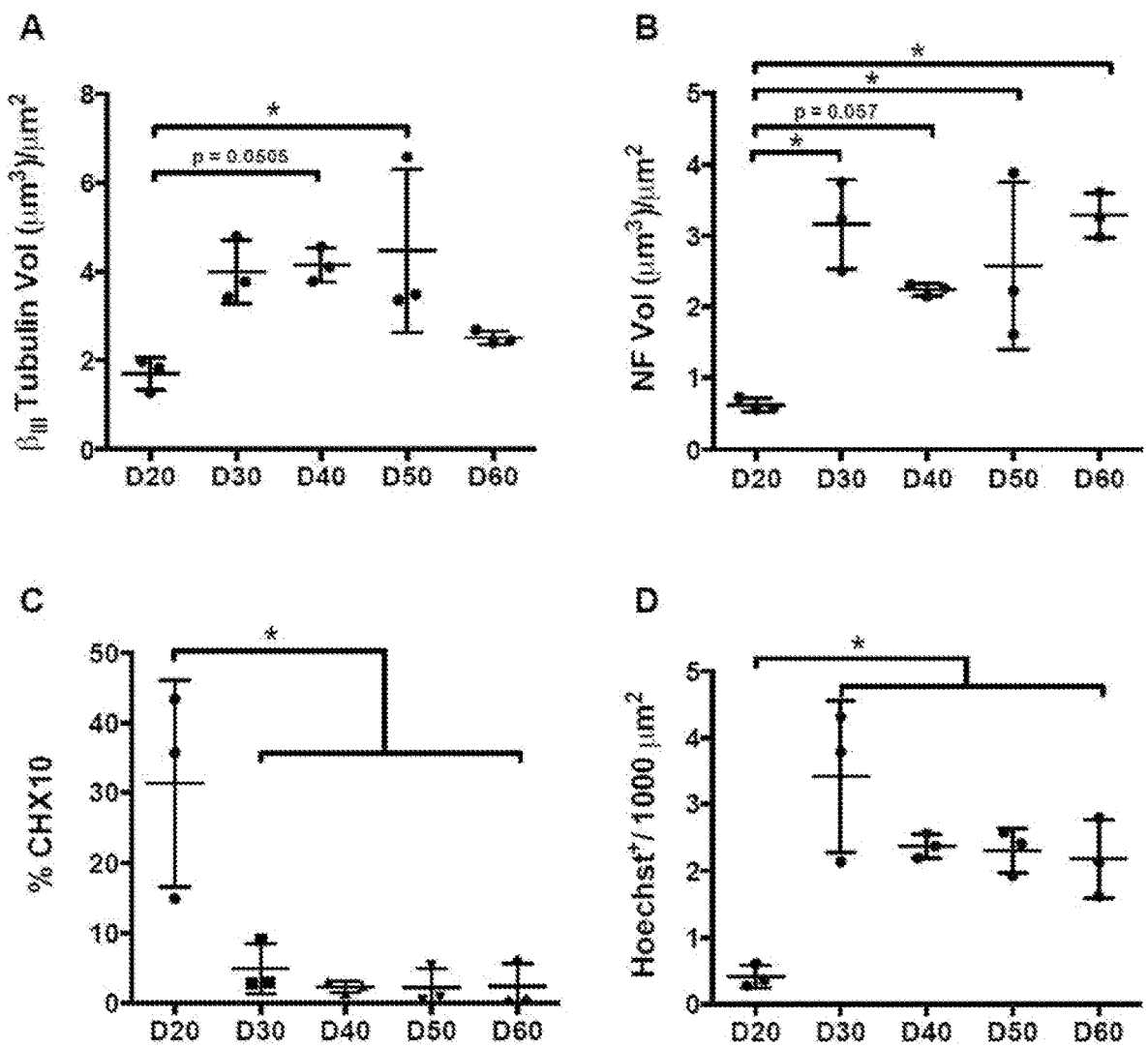
FIG. 17 provides graphs showing quantification of in vitro maturation cultures. (Panel A) Volume of βIII tubulin throughout culture duration normalized by observation view area. Day 50 volume was greater than day 20 volume ($p<0.05$, one-way ANOVA and Tukey post hoc comparison) (Panel B) Volume of neurofilament throughout culture duration normalized by observation view area. Day 60, day 50, and day 30 volume was greater than day 20 volume ($p<0.05$, one-way ANOVA and Tukey post hoc comparison) (Panel C) Percent CHX10$^+$ cells throughout culture duration. Day 20 percentage was greater than all other time points Day 50 volume was greater than day 20 volume (p<0.05, one-way ANOVA and Tukey post hoc comparison). (Panel D) Number of Hoechst+ cells throughout culture duration normalized by observation view area. Day 30 through day 60 were greater than day 20 Day 50 volume was greater than day 20 volume (p<0.05, one-way ANOVA and Tukey post hoc comparison).

To examine the maturation of V2a interneurons, differentiated cultures were dissociated after 17 d, re-plated, and analyzed on days 20, 30, 40, 50, and 60 of culture according to Neuronal Maturation (Protocol 2) (FIG. 15). By day 20, CHX10$^+$ cells expressed neuronal markers βIII tubulin and neurofilament, and expression persisted throughout 60 d of culture (FIG. 16, panels B-K and FIG. 17, panels A and B). Some neuronal nuclei (NeuN) colocalized with CHX10$^+$ cells, and NeuN expression continued through day 60 (FIG. 16, panels L-P). Vesicular glutamate transporter 2 (VGlut2), a marker of glutamatergic neurons, was not detected early (day 20; FIG. 16, panel Q), but was abundant in later-stage cultures (day 60), indicating the adoption of a mature glutamatergic fate (FIG. 16, panel Y). Although many CHX10$^+$ nuclei were readily apparent initially (day 20; FIG. 16, panel B), identification of CHX10$^+$ cells declined over time owing to reduced expression, as well as to an increase in the total number of cells in the cultures (FIG. 17, panels C and D). Overall, the temporal phenotypic expression patterns support the progressive, albeit limited, maturation in vitro of the V2a interneuron cultures.

Example 6

Figure 8A:
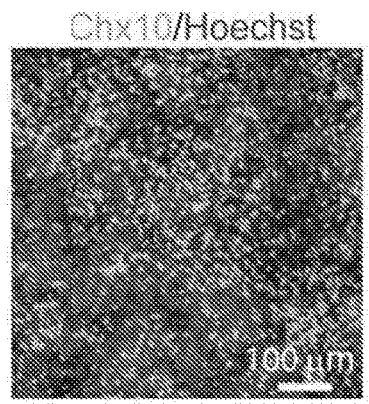
FIGS. 8A-8M are a collection of schematic diagrams, graphs and images showing in vivo maturation of in vitro hPSC-derived V2a interneurons, according to embodiments of the present disclosure.
Figure 8B:
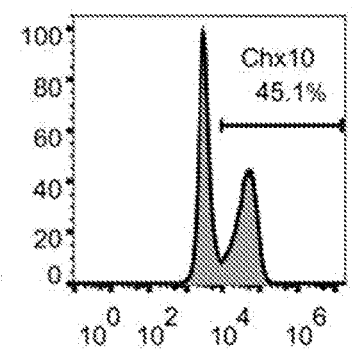
Figure 8C:
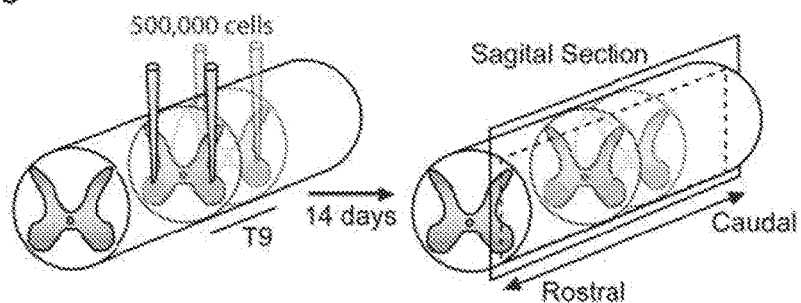
Figure 8D:
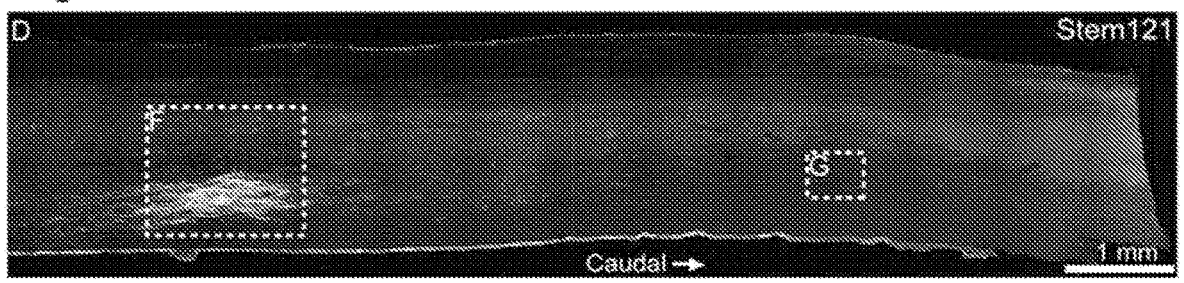
Figure 8E:
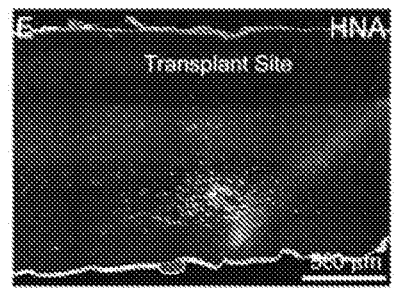
Figure 8F:
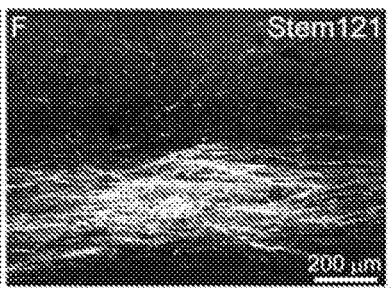
Figure 8G:
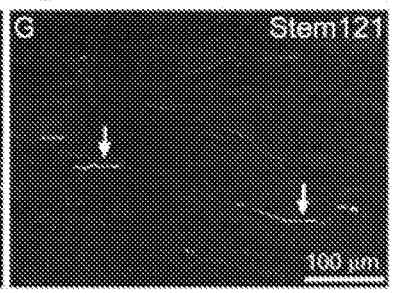
Figure 8H:
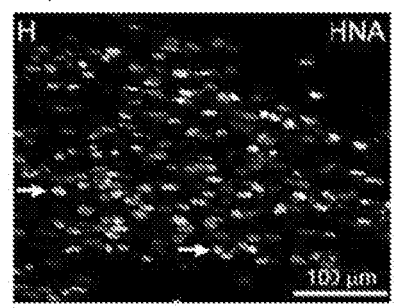
Figure 8I:
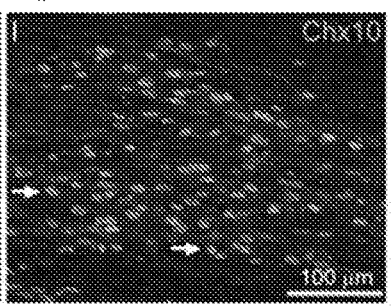
Figure 8J:
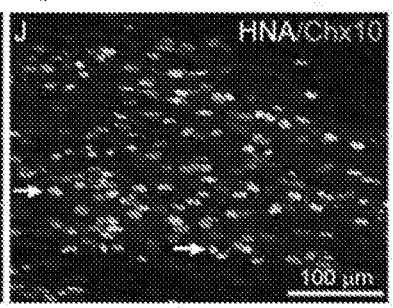
Figure 8K:
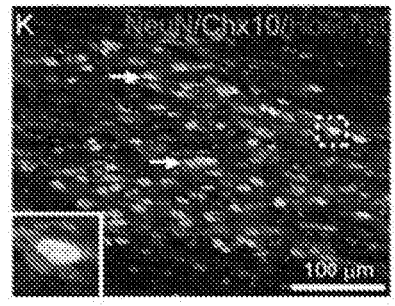
Figure 8L:
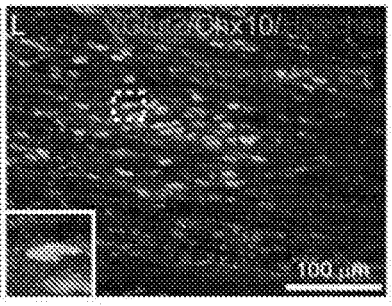
Figure 8M:
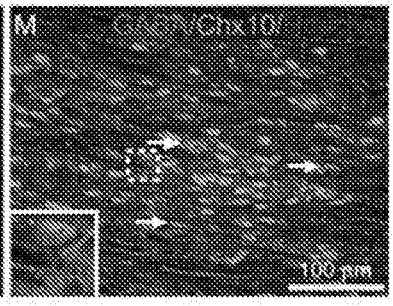
Figure 18:
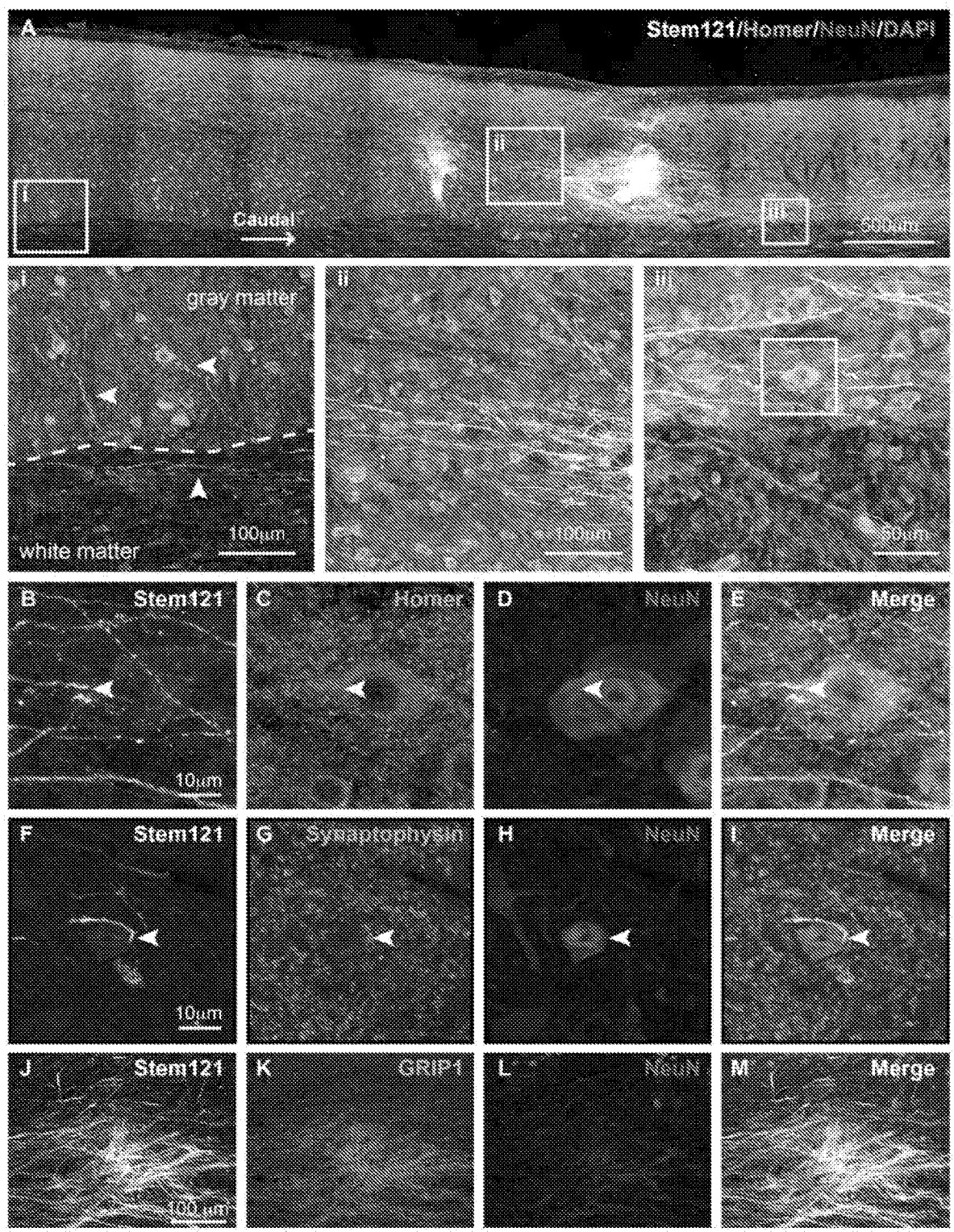
FIG. 18 provides immunostaining images showing that transplanted cells extend projections and form synapses with host neurons. (panel $A_{i-iii}$) Stem121 (white), Homer (green) and NeuN (red) immuno staining of transplanted V2a interneurons. (i) Inset of tissue rostral to the transplantation site. Horizontal arrows point to neurites that have extended into the gray matter. Vertical arrows point to neurites that have further extended into the white matter. (ii) Inset of tissue between the two transplantation sites. (iii) Inset of tissue caudal to the transplantation site. Box highlights the area shown in panels B-E. (Panels B-E) Stem121 (white), Homer (green) and NeuN (red) immunostaining of transplanted V2a interneurons. Arrows point to colocalization of Stem121, Homer, and NeuN. (Panels F-I) Stem121 (white), synaptophysin (green) and NeuN (red) immunostaining of transplanted V2a interneurons. Arrowheads point to colocalization of Stem121, synaptophysin, and NeuN. (J-M) Stem121 (white), NeuN (red), and GRIP1 (green) immunostaining of transplanted V2a interneurons.

Transplanted hPSC-Derived V2a Interneurons Survive and Mature in the Adult Murine Spinal Cord The physiological response of hPSC-derived V2a interneurons within the environment of the spinal cord was examined by transplanting differentiated cultures into naïve spinal cords of C57/SCID mice. V2a interneuron cultures (~45% CHX10$^+$ cells; FIGS. 8A-8B) were transplanted at thoracic vertebral level 9 (T9) and spinal cords were harvested two weeks later for histological analysis (FIG. 8C). Transplanted cells were observed in sagittal sections using markers for human cytoplasmic protein (Stem121, FIG. 8D) and human nuclear antigen (HNA, FIG. 8E). HNA$^+$ nuclei remained at the transplant site with limited migration along the rostral/caudal axis of the spinal cord. Stem121$^+$ cells were observed at the transplant site (FIG. 8F) with processes extending in both the rostral and caudal directions over 5 mm in distance (FIG. 8G). To assess the phenotype of the transplanted V2a interneurons, histological staining with a panel of different markers was performed in the adult murine spinal cord. Most of the HNA$^+$ cells co-expressed CHX10, thus confirming the survival of transplanted V2a interneurons (FIGS. 8H-8J). Additionally, many CHX10$^+$ cells also expressed NeuN (FIG. 8K, arrows and inset) and VGlut2 (FIG. 8L and inset), indicating neuronal maturation of V2a interneurons into a glutamatergic phenotype. Occasional GABA$^+$ cells were found in the vicinity of the transplant site, but CHX10$^+$/GABA$^+$ cells were not detected (FIG. 8M and inset) and no Oct4$^+$ cells were observed in any of the spinal cord sections that contained transplanted cells (FIGS. 9A-9D). Stem121$^+$ cells expressed the postsynaptic marker GRIP1 (FIGS. 9E-9H) and Stem121+ processes co-labeled with the pre-synaptic marker synaptophysin directly adjacent to host neurons (FIGS. 9I-9L and insets), indicating synapse formation and integration of transplanted cells with the host tissue. Transplanted hPSC-derived V2a interneurons projected to multiple locations in the murine spinal cord (FIG. 18, panel A). Stem121+ processes projected within the white matter, and many branched into the adjacent gray matter as well (FIG. 18, panel A, i). Transplanted neurons also projected axons between distinct transplantation sites (FIG. 18, panel A, ii). Putative synapse formations of the transplanted cell population with host cells were observed adjacent to the transplantation sites (FIG. 18, panel A, iii). The postsynaptic marker HOMER was found on host neurons (NeuN+) in direct proximity to abutting human cell neurites (Stem121+), suggesting synapse formation of transplanted cells with the host tissue (FIG. 18, panels B-E). In addition, human cell neurite endings expressing the presynaptic marker synaptophysin were observed directly adjacent to host neurons (FIG. 18, panels F-I). Stem121+ cells also expressed the postsynaptic marker GRIP1 (FIG. 18, panels J-M). These results demonstrate that transplanted hPSC-derived V2a interneurons survive, mature and extend long processes that appear to synapse onto host cells in the adult murine spinal cord.

FIGS. 8A-8M: Human PSC-derived V2a interneurons survive and mature in the adult murine spinal cord. (FIG. 8A) Immunostaining of CHX10 and DAPI nuclei labeling in V2a interneuron cultures on day 17. (FIG. 8B) Flow cytometry analysis of CHX10 in V2a interneuron cultures used for transplantation. (FIG. 8C) Schematic of cell transplantation into the adult murine spinal cord and sectioning of harvested spinal cord tissue at 2 weeks post-transplantation. (FIG. 8D) Stem 121 (human cytoplasmic protein, white) immunostaining in a sagittal tissue section caudal to T9. (FIG. 8E) HNA (human nuclear antigen, white) immuno staining near the transplantation site. (FIG. 8F) Stem121 (white) immunostaining at the transplant site (FIG. 8G) and at 5 mm away from the center of the transplantation site. (FIG. 8H-J) HNA (white) and CHX10 (green) immunostaining of V2a interneurons at the transplantation site. (FIG. 8K) NeuN and CHX10 (green) immuno staining and nuclei labeling of transplanted V2a interneurons. Inset in (FIG. 8K) contains a higher magnification image of a NeuN+/CHX10+ nuclei. (FIG. 8L) VGLUT2 and CHX10 immunostaining and nuclei labeling (blue) of transplanted V2a interneurons. Inset in (FIG. 8L) contains a higher magnification image of VGlut2 labeling adjacent to the CHX10+ nuclei of a transplanted V2a interneuron. (FIG. 8M) GABA and CHX10 immunostaining and nuclei labeling of transplanted V2a interneurons. Inset in (FIG. 8M) contains a higher magnification image of a GABA+/CHX10− cell adjacent to a GABA−/CHX10+ cell.

FIGS. 9A-9L: Transplanted cells express mature neuronal markers. (FIGS. 9A-9D) Stem121, Oct4, and DAPI nuclei labeling immunostaining of transplanted V2a interneurons. (FIGS. 9E-9H) Stem121, NeuN, and GRIP1 immunostaining of transplanted V2a interneurons. (FIGS. 9I-9L) Stem121, NeuN and synaptophysin immunostaining of transplanted V2a interneurons. Inset contains a higher magnification image of co-localized synaptophysin and Stem121 expression (arrows) adjacent to a host Stem121−/NeuN+ neuron.

Example 7

Figure 19:
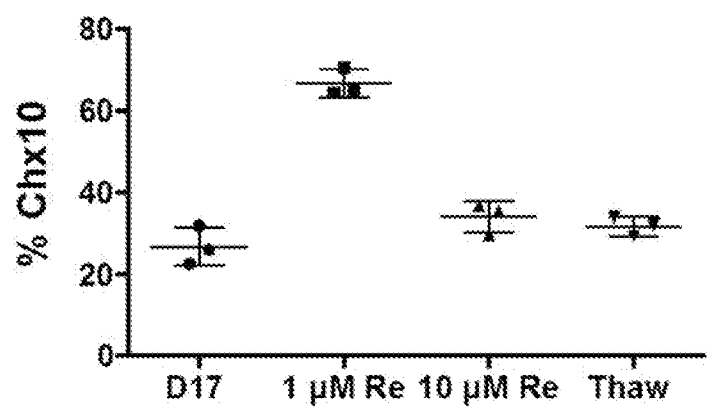
FIG. 19 provides a graph showing the % of CHX10+ cells following freeze-thaw and under different re-plating conditions.

Cultured V2a Interneurons Maintain CHX10 Percentage through Freeze-Thaw Procedure V2a interneuron cultures were frozen and thawed as described in the Materials and Methods above. As shown in FIG. 19, CHX10+ percentage of the thawed samples was approximately the same as day 17 samples as well as samples that have been dissociated, re-plated in 10 µM Rock inhibitor, and recovered for 3 days (10 µM Re). The ability to freeze and thaw the cells enables pre-screening of efficiencies, batching of differentiations, and scale-up for large animal studies.

Example 8

Re-Plating to Increase % of CHX10+ Cells in Culture

V2a interneuron cultures were re-plated using varying concentrations of Rock inhibitor as described in the Materials and Methods above. As shown in FIG. 19, the % of CHX10+ cells more than doubled after re-plating with 1 µM Rock inhibitor compared to day 17 samples (D17) and samples that had been re-plated with 10 µM rock inhibitor (10 µM Re). This method may be utilized for phenotypic characterization, maturation, and/or animal studies, where it would be beneficial to have a highly pure culture of V2a interneurons.

Example 9

Wnt Activation to Specify the Rostral/Caudal Identity

Figure 20A:
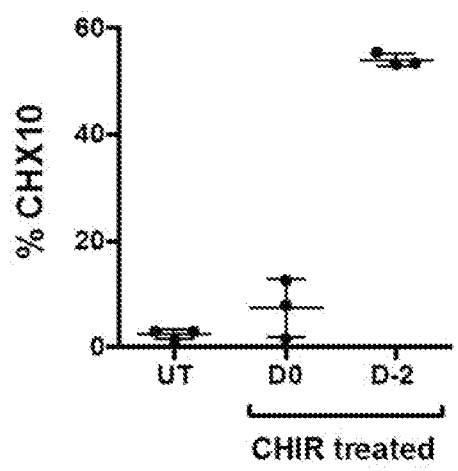
FIG. 20A provides a graph showing the % of CHX10+ cells following treatment with CHIR, a GSK3 inhibitor.
Figure 20B:
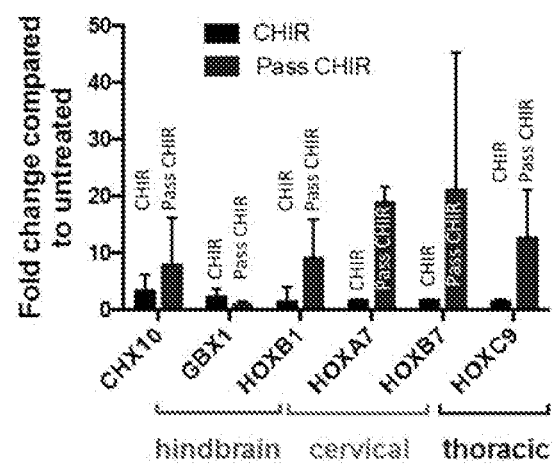
FIG. 20B provides a graph showing the fold change in gene expression for CHX10 and various hindbrain, cervical, and thoracic markers (Panel B).

Addition of the small molecule CHIR99021 ("CHIR") (a GSK3 inhibitor and therefore WNT activator) to the V2a interneuron protocol was tested as described in the Materials and Methods above. As shown in FIGS. 20A and 20B, addition of CHIR at D0 did not decrease the % of CHX10+ cells and slightly increased cervical and thoracic gene expression. Addition of CHIR at D-2 and passage with CHIR greatly increased the % of CHX10+ cells and also increased cervical and thoracic gene expression. These results support the idea that Wnt activation results in an increase in CHX10+ cells, and increases cervical and thoracic HOX expression, which is indicative of a more caudal phenotype. The duration of CHIR treatment modulates the % of CHX10+ cells and the HOX gene expression profile. These results are important since specification of the rostral-caudal identity is important for phenotypic characterization as well as specification for transplantation studies.

REFERENCES

1. Shi, Y., P. Kirwan, and F. J. Livesey, *Directed differentiation of human pluripotent stem cells to cerebral cortex neurons and neural networks.* Nat Protoc, 2012. 7(10): p. 1836-46.
2. Perrier, A. L., et al., *Derivation of midbrain dopamine neurons from human embryonic stem cells.* Proc Natl Acad Sci USA, 2004. 101(34): p. 12543-8.
3. Maroof, A. M., et al., *Directed differentiation and functional maturation of cortical interneurons from human embryonic stem cells.* Cell Stem Cell, 2013. 12(5): p. 559-72.
4. Nicholas, C. R., et al., *Functional maturation of hPSC-derived forebrain interneurons requires an extended timeline and mimics human neural development.* Cell Stem Cell, 2013. 12(5): p. 573-86.
5. Li, X. J., et al., *Specification of motoneurons from human embryonic stem cells.* Nat Biotechnol, 2005. 23(2): p. 215-21.

6. Amoroso, M. W., et al., *Accelerated high yield generation of limb-innervating motor neurons from human stem cells*. J Neurosci, 2013. 33(2): p. 574-86.
7. Butt, S. J., R. M. Harris-Warrick, and O. Kiehn, *Firing properties of identified interneuron populations in the mammalian hindlimb central pattern generator*. J Neurosci, 2002. 22(22): p. 9961-71.
8. Butt, S. J. and O. Kiehn, *Functional identification of interneurons responsible for left-right coordination of hindlimbs in mammals*. Neuron, 2003. 38(6): p. 953-63.
9. Ericson, J., et al., *Pax6 controls progenitor cell identity and neuronal fate in response to graded Shh signaling*. Cell, 1997. 90(1): p. 169-80.
10. Bretzner, F. and R. M. Brownstone, *Lhx3-Chx10 reticulospinal neurons in locomotor circuits*. J Neurosci, 2013. 33(37): p. 14681-92.
11. Ni, Y., et al., *Characterization of long descending premotor propriospinal neurons in the spinal cord*. J Neurosci, 2014. 34(28): p. 9404-17.
12. Azim, E., et al., *Skilled reaching relies on a V2a propriospinal internal copy circuit*. Nature, 2014. 508 (7496): p. 357-63.
13. Zhong, G., et al., *Electrophysiological characterization of V2a interneurons and their locomotor-related activity in the neonatal mouse spinal cord*. J Neurosci, 2010. 30(1): p. 170-82.
14. Crone, S. A., et al., *Genetic ablation of V2a ipsilateral interneurons disrupts left-right locomotor coordination in mammalian spinal cord*. Neuron, 2008. 60(1): p. 70-83.
15. Crone, S. A., et al., *Irregular Breathing in Mice following Genetic Ablation of V2a Neurons*. J Neurosci, 2012. 32(23): p. 7895-906.
16. Okada, Y., et al., *Retinoic-acid-concentration-dependent acquisition of neural cell identity during in vitro differentiation of mouse embryonic stem cells*. Dev Biol, 2004. 275(1): p. 124-42.
17. Marklund, U., et al., *Detailed expression analysis of regulatory genes in the early developing human neural tube*. Stem Cells Dev, 2014. 23(1): p. 5-15.
18. Del Barrio, M. G., et al., *A regulatory network involving Foxn4, Mash1 and delta-like 4/Notch1 generates V2a and V2b spinal interneurons from a common progenitor pool*. Development, 2007. 134(19): p. 3427-36.
19. Brown, C. R., et al., *Generation of v2a interneurons from mouse embryonic stem cells*. Stem Cells Dev, 2014. 23(15): p. 1765-76.
20. Iyer, N. R., et al., *Generation of highly enriched V2a interneurons from mouse embryonic stem cells*. Exp Neurol, 2016. 277: p. 305-16.
21. Lian, X., et al., *Directed cardiomyocyte differentiation from human pluripotent stem cells by modulating Wnt/beta-catenin signaling under fully defined conditions*. Nat Protoc, 2013. 8(1): p. 162-75.
22. Yoon, K. and N. Gaiano, *Notch signaling in the mammalian central nervous system: insights from mouse mutants*. Nat Neurosci, 2005. 8(6): p. 709-15.
23. Louvi, A. and S. Artavanis-Tsakonas, *Notch signalling in vertebrate neural development*. Nat Rev Neurosci, 2006. 7(2): p. 93-102.
24. Borghese, L., et al., *Inhibition of notch signaling in human embryonic stem cell-derived neural stem cells delays G1/S phase transition and accelerates neuronal differentiation in vitro and in vivo*. Stem Cells, 2010. 28(5): p. 955-64.
25. Batista, M. F., J. Jacobstein, and K. E. Lewis, *Zebrafish V2 cells develop into excitatory CiD and Notch signalling dependent inhibitory VeLD interneurons*. Dev Biol, 2008. 322(2): p. 263-75.
26. Skaggs, K., D. M. Martin, and B. G. Novitch, *Regulation of spinal interneuron development by the Olig-related protein Bhlhb5 and Notch signaling*. Development, 2011. 138(15): p. 3199-211.
27. Cornacchia, D. and L. Studer, *Back and forth in time: Directing age in iPSC-derived lineages*. Brain Res, 2015.
28. Roskams, A. J., X. Cai, and G. V. Ronnett, *Expression of neuron-specific beta-III tubulin during olfactory neurogenesis in the embryonic and adult rat*. Neuroscience, 1998. 83(1): p. 191-200.
29. Dougherty, K. J. and O. Kiehn, *Firing and cellular properties of V2a interneurons in the rodent spinal cord*. J Neurosci, 2010. 30(1): p. 24-37.
30. Al-Mosawie, A., J. M. Wilson, and R. M. Brownstone, *Heterogeneity of V2-derived interneurons in the adult mouse spinal cord*. Eur J Neurosci, 2007. 26(11): p. 3003-15.
31. Lundfald, L., et al., *Phenotype of V2-derived interneurons and their relationship to the axon guidance molecule EphA4 in the developing mouse spinal cord*. Eur J Neurosci, 2007. 26(11): p. 2989-3002.
32. Livak, K. J. and T. D. Schmittgen, *Analysis of relative gene expression data using real-time quantitative PCR and the 2(-Delta Delta C(T)) Method*. Methods, 2001. 25(4): p. 402-8.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A method to generate spinal cord glutamatergic interneurons from a population of human pluripotent stem cells (hPSCs) comprising,
   a) culturing hPSCs in vitro in a neural induction medium comprising a retinoic acid signaling pathway activator, and
   b) culturing the cells from a) in a neural induction medium comprising a retinoic acid signaling pathway activator, a Shh signaling pathway activator, and a Notch signaling pathway inhibitor,
   so as to generate CHX10$^+$ V2a interneurons.

2. The method of claim 1, wherein the retinoic acid signaling pathway activator comprises a retinoic acid receptor agonist.

3. The method of claim 1, wherein the Shh signaling pathway activator comprises a Smoothened agonist.

4. The method of claim 1, wherein the Notch signaling pathway inhibitor comprises an inhibitor of Notch receptor activation.

5. The method of claim 1, wherein the retinoic acid signaling pathway activator is present in the neural induction medium at a concentration of about 20 nM to about 500 nM.

6. The method of claim 1, wherein the Shh signaling pathway activator is present in the neural induction medium at a concentration in the range of about 50 nM to about 500 nM.

7. The method of claim 1, wherein the Notch signaling pathway inhibitor is present in the neural induction medium of b) at a concentration in the range of about 250 nM to about 10 µM.

8. The method of claim 1, wherein b) is performed about two days after a).

9. The method of claim 1, wherein culturing with the neural induction medium of a) is for a period of 7 to 13 days after contacting the hPSCs with the neural induction medium of a).

10. The method of claim 1, wherein the neural induction medium of a) further comprises one or more SMAD signaling pathway inhibitors.

11. The method of claim 1, wherein the neural induction medium of b) does not comprise one or more SMAD signaling pathway inhibitors.

12. The method of claim 1, wherein the hPSCs of a) are cultured on a cell culture substrate comprising a coating of extracellular matrix components.

13. The method of claim 1, wherein the culturing comprises seeding the of hPSCs of a) on a cell culture substrate at a density of about 5,000 to about 120,000 cells/cm$^2$.

14. The method of claim 1, wherein the hPSCs of a) comprise embryonic stem cells (ESCs) or induced pluripotent stem cells (iPSCs).

15. The method of claim 1, wherein gene expression of the cells of b) are enriched, compared to the hPSCs of a), for one or more genes selected from: FOXN4, CHX10, SOX14, NF Light Chain, and $\beta_{III}$ tubulin.

16. The method of claim 1, further comprising:
   c) reseeding at least some of the cells of b) onto a neural maturation substrate; and
   d) culturing the seeded cells of c) in a neural maturation medium, thereby generating a mature population of CHX10$^+$ V2a interneurons.

17. A method to generate spinal cord glutamatergic interneurons from a population of human pluripotent stem cells (hPSCs) comprising,
   a) culturing hPSCs in vitro in a neural induction medium comprising a retinoic acid signaling pathway activator,
   b) culturing the cells from a) in a neural induction medium comprising a retinoic acid signaling pathway activator and a Shh signaling pathway activator, and
   c) culturing the cells from b) in a neural induction medium comprising a retinoic acid signaling pathway activator, a Shh signaling pathway activator and a Notch signaling pathway inhibitor,
   so as to generate CHX10$^+$ V2a interneurons.

18. The method of claim 17, wherein b) is performed about two days after a).

19. The method of claim 17, wherein culturing with the neural induction medium of a) is for a period of 7 to 13 days after contacting the hPSCs with the neural induction medium of a).

20. The method of claim 17, wherein the neural induction medium of a) further comprises one or more SMAD signaling pathway inhibitors.

21. The method of claim 17, wherein the neural induction medium of b) and c) do not comprise one or more SMAD signaling pathway inhibitors.

22. The method of claim 17, further comprising:
   d) reseeding at least some of the cells of c) onto a neural maturation substrate; and
   e) culturing the seeded cells of d) in a neural maturation medium, thereby generating a mature population of CHX10$^+$ V2a interneurons.

* * * * *

UNITED STATES PATENT AND TRADEMARK OFFICE
CERTIFICATE OF CORRECTION

PATENT NO. : 11,702,630 B2
APPLICATION NO. : 16/303580
DATED : July 18, 2023
INVENTOR(S) : Butts et al.

It is certified that error appears in the above-identified patent and that said Letters Patent is hereby corrected as shown below:

On the Title Page

On page 2, in Column 2, under item (56) "Other Publications", Line 21, delete "invertebrate" and insert --in vertebrate-- therefor In the Claims In Column 54, Line 21, in Claim 13, after "the", delete "of"

Signed and Sealed this
Twenty-ninth Day of October, 2024

Katherine Kelly Vidal
*Director of the United States Patent and Trademark Office*